United States Patent
Bernate et al.

(10) Patent No.: US 10,822,621 B2
(45) Date of Patent: *Nov. 3, 2020

(54) AUTOMATED NUCLEIC ACID ASSEMBLY AND INTRODUCTION OF NUCLEIC ACIDS INTO CELLS

(71) Applicant: Inscripta, Inc., Boulder, CO (US)

(72) Inventors: Jorge Bernate, Boulder, CO (US); Don Masquelier, Boulder, CO (US); Phillip Belgrader, Pleasanton, CA (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/548,208

(22) Filed: Aug. 22, 2019

(65) Prior Publication Data

US 2019/0382795 A1 Dec. 19, 2019

Related U.S. Application Data

(63) Continuation of application No. 16/147,871, filed on Sep. 30, 2018, now Pat. No. 10,415,058.

(60) Provisional application No. 62/566,374, filed on Sep. 30, 2017, provisional application No. 62/566,375, filed on Sep. 30, 2017, provisional application No. 62/566,688, filed on Oct. 2, 2017, provisional application No. 62/567,697, filed on Oct. 3, 2017, provisional application No. 62/620,370, filed on Jan. 22, 2018, provisional application No. 62/649,731, (Continued)

(51) Int. Cl.
| | | |
|---|---|---|
| C12M 3/00 | (2006.01) | |
| C12M 1/00 | (2006.01) | |
| C12N 15/87 | (2006.01) | |
| C12M 1/42 | (2006.01) | |
| C12N 15/70 | (2006.01) | |
| C12N 15/81 | (2006.01) | |
| C12M 1/36 | (2006.01) | |

(52) U.S. Cl.
CPC .............. *C12N 15/87* (2013.01); *C12M 23/44* (2013.01); *C12M 35/02* (2013.01); *C12M 41/48* (2013.01); *C12N 15/70* (2013.01); *C12N 15/81* (2013.01)

(58) Field of Classification Search
CPC ....... C12M 35/00; C12M 35/02; C12M 35/04
See application file for complete search history.

(56) References Cited

U.S. PATENT DOCUMENTS

| 5,710,381 A | 1/1998 | Atwood et al. |
| 6,074,605 A | 6/2000 | Meserol et al. |

(Continued)

FOREIGN PATENT DOCUMENTS

| EP | 2135626 | 1/2011 |
| EP | 1766004 | 8/2016 |

(Continued)

OTHER PUBLICATIONS

Bao, et al., "Genome-scale engineering of Saccharomyces cerevisiae with single-nucleotide precision", Nature Biotechnology, doi:10.1038/nbt.4132, pp. 1-6 (May 7, 2018).

(Continued)

*Primary Examiner* — Nathan A Bowers
(74) *Attorney, Agent, or Firm* — Sarah Brashears; Dianna L. DeVore

(57) ABSTRACT

In an illustrative embodiment, automated instruments comprising one or more flow-through electroporation devices or modules are provided to automate transformation of nucleic acids in live cells.

40 Claims, 50 Drawing Sheets

Related U.S. Application Data filed on Mar. 29, 2018, provisional application No. 62/671,385, filed on May 14, 2018, provisional application No. 62/648,130, filed on Mar. 26, 2018, provisional application No. 62/657,651, filed on Apr. 13, 2018, provisional application No. 62/657,654, filed on Apr. 13, 2018, provisional application No. 62/689,068, filed on Jun. 23, 2018.

(56) References Cited

U.S. PATENT DOCUMENTS

| | | | |
|---|---|---|---|
| 6,150,148 | A | 11/2000 | Nanda et al. |
| 6,482,619 | B1 | 11/2002 | Rubinsky et al. |
| 6,654,636 | B1 | 11/2003 | Dev et al. |
| 6,746,441 | B1 | 6/2004 | Hofmann et al. |
| 6,837,995 | B1 | 1/2005 | Vassarotti et al. |
| 7,029,916 | B2 | 4/2006 | Dzekunov et al. |
| 7,141,425 | B2 | 11/2006 | Dzekunov et al. |
| 7,166,443 | B2 | 1/2007 | Walker et al. |
| 7,422,889 | B2 | 9/2008 | Sauer et al. |
| 8,110,112 | B2 | 2/2012 | Alburty et al. |
| 8,153,432 | B2 | 4/2012 | Church et al. |
| 8,569,041 | B2 | 10/2013 | Church et al. |
| 8,584,535 | B2 | 11/2013 | Page et al. |
| 8,584,536 | B2 | 11/2013 | Page et al. |
| 8,667,839 | B2 | 3/2014 | Kimura |
| 8,667,840 | B2 | 3/2014 | Lee et al. |
| 8,677,839 | B2 | 3/2014 | Page et al. |
| 8,677,840 | B2 | 3/2014 | Page et al. |
| 8,697,359 | B1 | 4/2014 | Zhang et al. |
| 8,726,744 | B2 | 5/2014 | Alburty et al. |
| 8,758,623 | B1 | 6/2014 | Alburty et al. |
| 8,932,850 | B2 | 1/2015 | Chang et al. |
| 9,029,109 | B2 | 5/2015 | Hur et al. |
| 9,063,136 | B2 | 6/2015 | Talebpour et al. |
| 9,534,989 | B2 | 1/2017 | Page et al. |
| 9,546,350 | B2 | 1/2017 | Dzekunov et al. |
| 9,593,359 | B2 | 3/2017 | Page et al. |
| 9,738,918 | B2 | 8/2017 | Alburty et al. |
| 9,776,138 | B2 | 10/2017 | Innings et al. |
| 9,790,490 | B2 | 10/2017 | Zhang et al. |
| 9,896,696 | B2 | 2/2018 | Begemann et al. |
| 9,982,279 | B1 | 5/2018 | Gill et al. |
| 10,017,760 | B2 | 7/2018 | Gill et al. |
| 2002/0139741 | A1 | 10/2002 | Kopf |
| 2003/0059945 | A1 | 3/2003 | Dzekunov et al. |
| 2003/0073238 | A1 | 4/2003 | Dzekunov et al. |
| 2003/0104588 | A1 | 6/2003 | Orwar et al. |
| 2004/0115784 | A1 | 6/2004 | Dzekunov et al. |
| 2004/0171156 | A1 | 9/2004 | Hartley et al. |
| 2005/0064584 | A1 | 3/2005 | Bargh |
| 2005/0118705 | A1 | 6/2005 | Rabbitt et al. |
| 2006/0001865 | A1 | 1/2006 | Bellalou et al. |
| 2006/0224192 | A1 | 10/2006 | Dimmer et al. |
| 2007/0105206 | A1 | 5/2007 | Lu et al. |
| 2007/0231873 | A1 | 10/2007 | Ragsdale |
| 2007/0249036 | A1 | 10/2007 | Ragsdale et al. |
| 2008/0138877 | A1 | 6/2008 | Dzekunov et al. |
| 2010/0055790 | A1 | 3/2010 | Simon |
| 2010/0076057 | A1 | 3/2010 | Sontheimer et al. |
| 2011/0009807 | A1 | 1/2011 | Kjeken et al. |
| 2011/0065171 | A1 | 3/2011 | Dzekunov et al. |
| 2011/0213288 | A1 | 9/2011 | Choi et al. |
| 2011/0236962 | A1 | 9/2011 | Loebbert et al. |
| 2012/0156786 | A1 | 6/2012 | Bebee |
| 2013/0005025 | A1 | 1/2013 | Church et al. |
| 2013/0015119 | A1 | 1/2013 | Pugh et al. |
| 2013/0196441 | A1 | 8/2013 | Rubinsky et al. |
| 2014/0068797 | A1 | 3/2014 | Doudna et al. |
| 2014/0121728 | A1 | 5/2014 | Dhillon et al. |
| 2014/0199767 | A1 | 7/2014 | Barrangou et al. |
| 2014/0273226 | A1 | 9/2014 | Wu et al. |
| 2014/0350456 | A1 | 11/2014 | Caccia |
| 2015/0098954 | A1 | 4/2015 | Hyde et al. |
| 2015/0159174 | A1 | 6/2015 | Frendewey et al. |
| 2015/0176013 | A1 | 6/2015 | Musunuru et al. |
| 2015/0297887 | A1 | 10/2015 | Dhillon et al. |
| 2016/0024529 | A1 | 1/2016 | Carstens et al. |
| 2016/0053272 | A1 | 2/2016 | Wurzel et al. |
| 2016/0053304 | A1 | 2/2016 | Wurzel et al. |
| 2016/0076093 | A1 | 3/2016 | Shendure et al. |
| 2016/0102322 | A1 | 4/2016 | Ravinder et al. |
| 2016/0168592 | A1 | 6/2016 | Church et al. |
| 2016/0272961 | A1 | 9/2016 | Lee |
| 2016/0281047 | A1 | 9/2016 | Chen et al. |
| 2016/0289673 | A1 | 10/2016 | Huang et al. |
| 2016/0298074 | A1 | 10/2016 | Dai |
| 2016/0298134 | A1 | 10/2016 | Chen et al. |
| 2016/0310943 | A1 | 10/2016 | Woizenko et al. |
| 2016/0367991 | A1 | 12/2016 | Cepheid |
| 2017/0002339 | A1 | 1/2017 | Barrangou et al. |
| 2017/0029805 | A1 | 2/2017 | Li et al. |
| 2017/0051310 | A1 | 2/2017 | Doudna et al. |
| 2017/0073705 | A1 | 3/2017 | Chen et al. |
| 2017/0159045 | A1 | 6/2017 | Serber et al. |
| 2017/0191123 | A1 | 7/2017 | Kim et al. |
| 2017/0218355 | A1 | 8/2017 | Buie et al. |
| 2017/0240922 | A1 | 8/2017 | Gill et al. |
| 2017/0283761 | A1 | 10/2017 | Corso |
| 2017/0307606 | A1 | 10/2017 | Hallock |
| 2017/0349874 | A1 | 12/2017 | Jaques et al. |
| 2018/0023045 | A1 | 1/2018 | Hallock et al. |
| 2018/0051327 | A1 | 2/2018 | Blainey et al. |
| 2018/0169148 | A1 | 6/2018 | Adair et al. |
| 2018/0179485 | A1 | 6/2018 | Borenstein et al. |
| 2019/0136224 | A1 | 5/2019 | Garcia Dominguez et al. |

FOREIGN PATENT DOCUMENTS

| | | |
|---|---|---|
| EP | 2459696 | 11/2017 |
| WO | WO 2003/057819 | 7/2001 |
| WO | WO 2009/091578 | 7/2009 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2015/021270 | 2/2015 |
| WO | WO 2016/003485 | 1/2016 |
| WO | WO 2016/054939 | 4/2016 |
| WO | WO 2016/145290 | 9/2016 |
| WO | WO 2018/015544 | 1/2018 |
| WO | WO 2018/191715 | 10/2018 |
| WO | WO 2012/012779 | 1/2019 |

OTHER PUBLICATIONS

Dicarlo, et al., "Genome engineering in *Saccharomyces cervisiae* using CRISPR-Case systems", Nucleic Acids Research, 41(7):4336-43 (2013).

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Verwaal, et al., "CRISPR/Cpf1 enables fast and simple genome editing of *Saccharamyces cerevisiae*", Yeast, 35:201-11 (2018).

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

Roy, et cl., "Multiplexed precision genome editing with trackable genomic barcodes in yeast", Nature Biotechnolgy, doi:10.1038/nbt.4137, pp. 1-16 (2018).

Dong, "Establishment of a highly efficient virus-inducible CRISPR/Cas9 system in insect cells," Antiviral Res., 130:50-7(2016).

Epinat et al., "A novel engineered meganuclease induces homologous recombination in eukaryotic cells, e.g., yeast and mammalian cells", Nucleic Acids Research, 31(11): 2952-2962.

(56) References Cited

OTHER PUBLICATIONS

Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Adamo, et al., "Flow-through comb electroporation device for delivery of macromolecules", Analytical Chemistry, 85(3):1637-41 (2015).
International Search Report and Written Opinion for International Application No. PCT/US2018/040519, dated Sep. 26, 2018, p. 1-8.
International Search Report and Written Opinion for International Application No. PCT/US2018/053670, dated Jan. 3, 2019, p. 1-13.
International Search Report and Written Opinion for International Application No. PCT/US2018/053671, dated Nov. 23, 2018, p. 1-12.
International Search Report and Written Opinion for International Application No. PCT/US2019/023342, dated Jun. 6, 2019, p. 1-12.
International Search Report and Written Opinion for International Application No. PCT/US2019/026836, dated Jul. 2, 2019, p. 1-10.
International Search Report and Written Opinion for International Application No. PCT/US2019/030085, dated Jul. 23, 2019, p. 1-14.
NonFinal Office Action for U.S. Appl. No. 16/024,816 dated Sep. 4, 2018, p. 1-10.
Final Office Action for U.S. Appl. No. 16/024,816 dated Nov. 26, 2012.
First Office Action Interview Pilot Program Pre-Interview Communication for U.S. Appl. No. 16/024,831, dated Feb. 12, 2019, p. 1-37.
NonFinal Office Action for U.S. Appl. No. 16/399,998, dated Jul. 31, 2019, p. 1-20.
First Office Action Interview Pilot Program Pre-Interview Communication for U.S. Appl. No. 16/454,865 dated Aug. 16, 2019, p. 1-36.

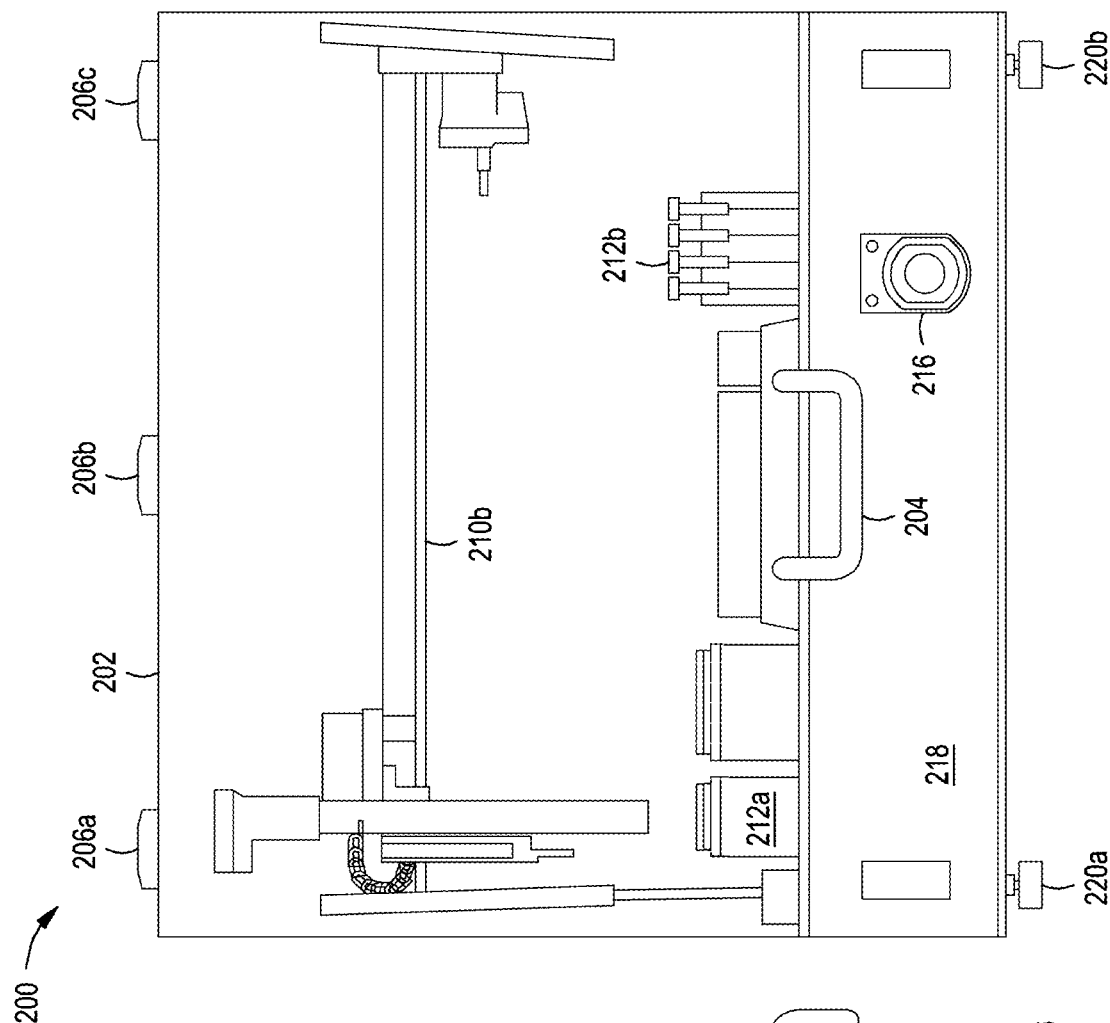
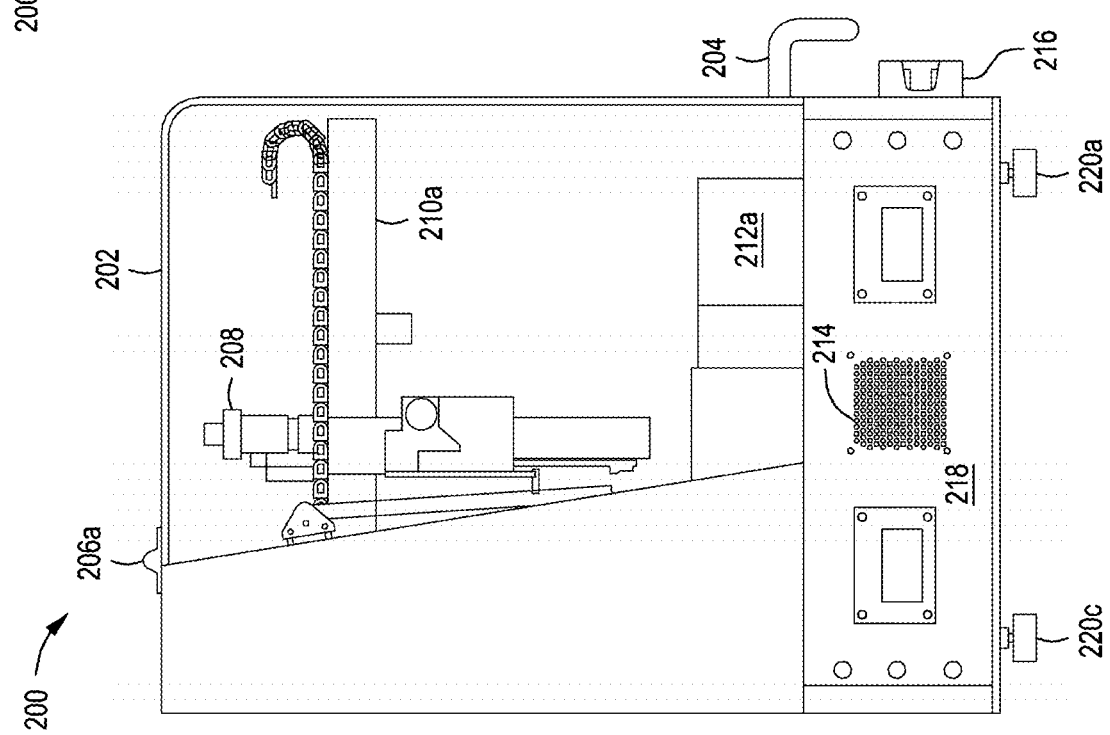

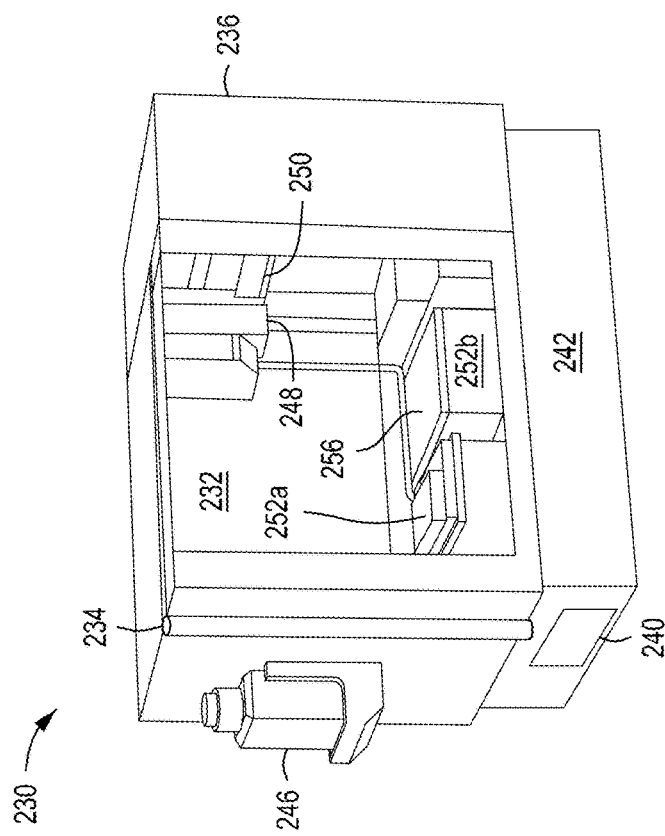
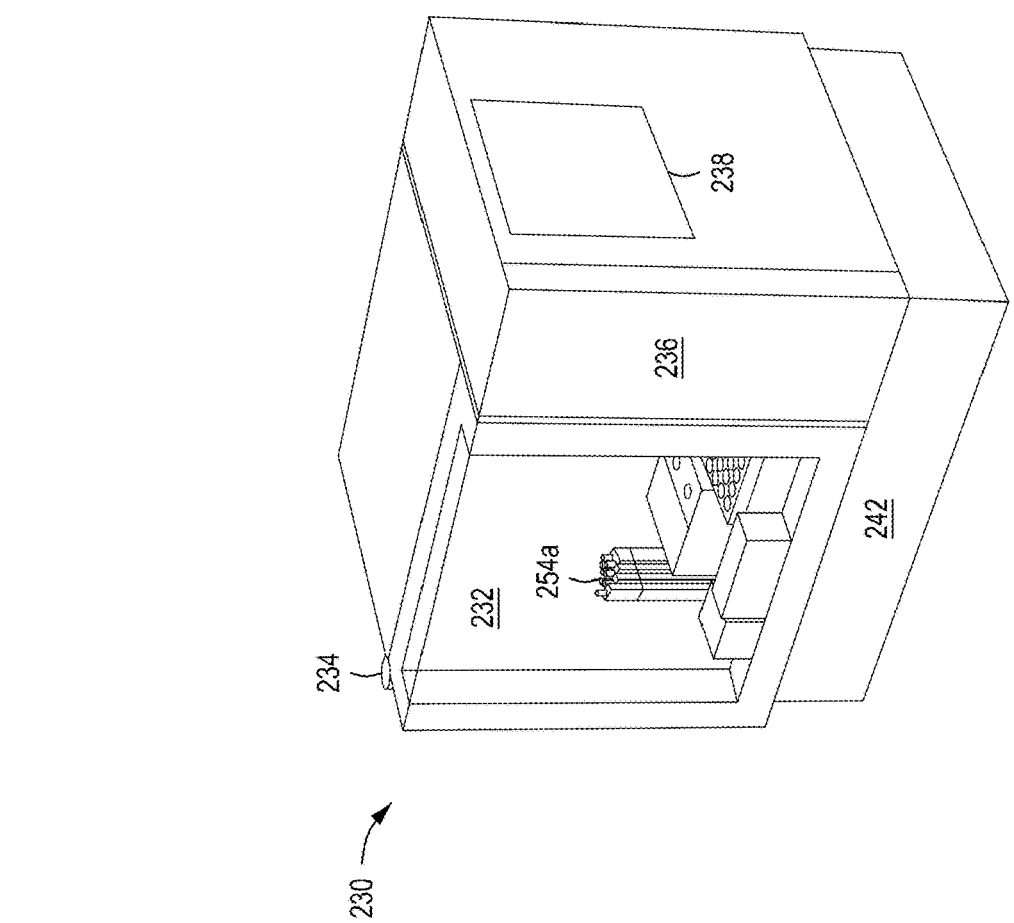
FIG. 2D
FIG. 2C

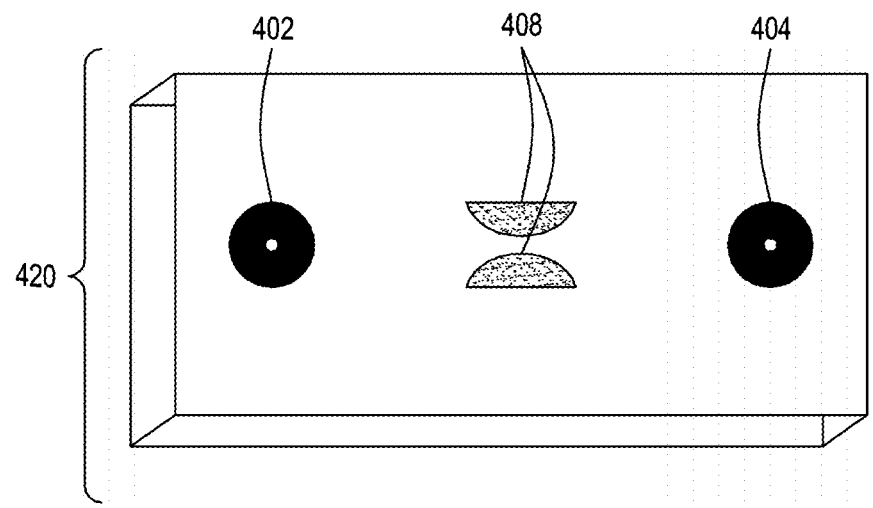
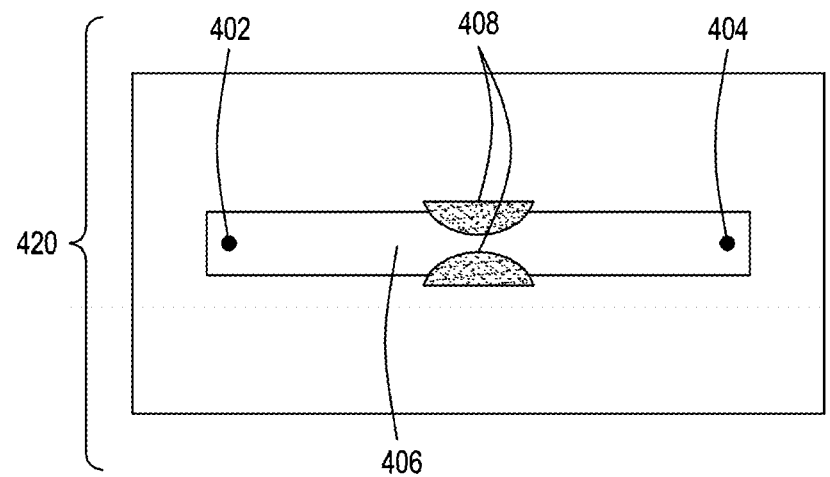
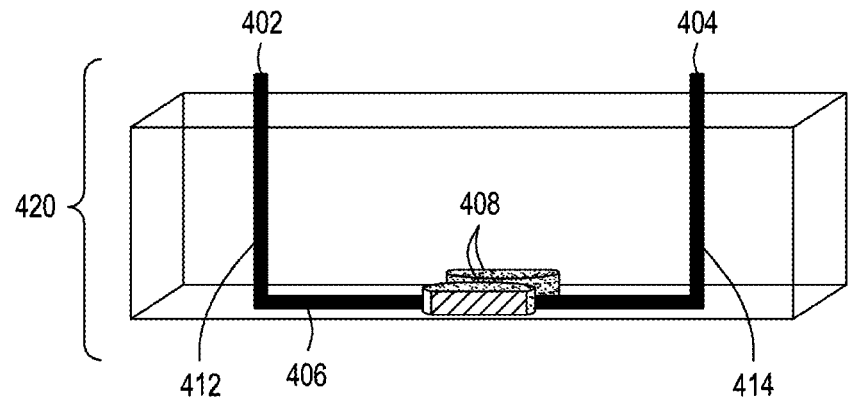

AUTOMATED NUCLEIC ACID ASSEMBLY AND INTRODUCTION OF NUCLEIC ACIDS INTO CELLS

RELATED APPLICATIONS

This application is a continuation of U.S. patent application Ser. No. 16/147,871, now U.S. Pat. No. 10,415,058, entitled "Automated Nucleic Acid Assembly and Introduction of Nucleic Acids into Cells: filed Sep. 30, 2018, which claims priority to U.S. Patent Application Ser. No. 62/566,374, entitled "Electroporation Device," filed Sep. 30, 2017; U.S. Patent Application Ser. No. 62/566,375, entitled "Electroporation Device," filed Sep. 30, 2017; U.S. Patent Application Ser. No. 62/566,688, entitled "Introduction of Nucleic acids into Cells," filed Oct. 2, 2017; U.S. Patent Application Ser. No. 62/567,697, entitled "Automated Nucleic Acid Assembly and Introduction of Nucleic Acids into Cells," filed Oct. 3, 2017; U.S. Patent Application Ser. No. 62/620,370, entitled "Automated Filtration and Manipulation of Viable Cells," filed Jan. 22, 2018; U.S. Patent Application Ser. No. 62/649,731, entitled "Automated Control of Cell Growth Rates for Induction and Transformation," filed Mar. 29, 2018; U.S. Patent Application Ser. No. 62/671,385, entitled "Automated Control of Cell Growth Rates for Induction and Transformation," filed May 14, 2018; U.S. Patent Application Ser. No. 62/648,130, entitled "Genomic Editing in Automated Systems," filed Mar. 26, 2018; U.S. Patent Application Ser. No. 62/657,651, entitled "Combination Reagent Cartridge and Electroporation Device," filed Apr. 13, 2018; U.S. Patent Application Ser. No. 62/657,654, entitled "Automated Cell Processing Systems Comprising Cartridges," filed Apr. 13, 2018; and U.S. Patent Application Ser. No. 62/689,068, entitled "Nucleic Acid Purification Protocol for Use in Automated Cell Processing Systems," filed Jun. 26, 2018. All above identified applications are hereby incorporated by reference in their entireties for all purposes.

BACKGROUND

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

A cell membrane constitutes the primary barrier for the transport of molecules and ions between the interior and the exterior of a cell. Electroporation, also known as electropermeabilization, substantially increases the membrane permeability in the presence of a pulsed electric field. The technique is more reproducible, universally applicable, and efficient than other physical methods and alternative biological and chemical techniques.

Conventional electroporation is typically conducted by exerting short electric pulses of defined intensity and duration to a cuvette equipped with embedded electrodes inside. Potter H., *Anal. Biochem.*, 1988, 174, 361-373 The electrodes are commonly fabricated out of aluminum (Al), stainless-steel, platinum (Pt) or graphite, and arranged in a plate-to-plate manner. A pulse generator such as special capacitor discharge equipment is required to generate the high voltage pulses. By tuning the electric parameters, electroporation efficiency and cell viability (for delivery) can be optimized. Canatella P J et al., *Biophys. J.*, 2001, 80, 755-764.

Although the traditional electroporation systems have been widely used, they require a high voltage input and suffer from adverse environmental conditions such as electric field distortion, local pH variation, metal ion dissolution and excess heat generation, resulting in low electroporation efficiency and/or cell viability.

In addition, the materials such as nucleic acids that are transformed into cells need to exhibit the appropriate activity following transformation. This often requires the assembly of the materials to be transformed into a form that allows, e.g., recovery, expression, transcription, translation, etc. of the RNA and/or proteins encoded by the nucleic acid. There is thus a need for automated methods of introducing assembled nucleic acids into cells in an automated fashion. The present invention addresses this need.

SUMMARY OF ILLUSTRATIVE EMBODIMENTS

The present disclosure is based on the development of automated instruments and systems for carrying out automated methods of transformation of nucleic acids into cells. These methods can be used to generate libraries of living cells of interest having the nucleic acids introduced therein. The novel, automated methods carried out using the instruments and system of the disclosure can be used with a variety of materials and techniques, and can be used with or without use of one or more selectable markers. Optionally, the automated instrument also comprises a module for the automated assembly of the nucleic acids to be transformed into the cells.

In some aspects, the disclosure provides an instrument for automated live cell electroporation, the instrument having a receptacle configured to receive nucleic acids to be delivered to the cells; a receptacle configured to receive live cells; an electroporation device for introduction of the assembled nucleic acids into the cells, and a processor-based system configured to operate the instrument based on user input. The automated introduction of the nucleic acids into the cells is preferably performed using one or more flow through electroporation (FTEP) devices, as described in more detail herein.

In some aspects, the disclosure provides an instrument for nucleic acid assembly and automated live cell electroporation, the instrument having a receptacle configured to receive nucleic acids to be assembled and delivered to the cells; an assembly module for the assembly of nucleic acids to be transformed into the cells; a receptacle configured to receive live cells; an electroporation device for introduction of the assembled nucleic acids into the cells, and a processor-based system configured to operate the instrument based on user input.

In specific embodiments, the instrument comprises two or more flow-through electroporation devices that can introduce different nucleic acids into populations of different cells in a single operation of the instrument.

In certain aspects, the instrument further provides a purification module into which the assembled nucleic acids are transferred prior to transformation. The purification can remove unwanted components of the nucleic acid assembly mixture (e.g., salts, minerals) and optionally concentrate the assembled nucleic acids.

In specific aspects, the disclosure provides an instrument for automated live cell electroporation, the instrument having a receptacle configured to receive live cells and nucleic acids to be delivered to the cells, an electroporation device for introduction of the nucleic acids into the cells, and a processor-based system configured to operate the instrument based on user input.

In other specific aspects, the disclosure provides an instrument for automated live cell electroporation, the instrument having a receptacle configured to receive live cells, a receptacle configured to receive nucleic acids to be delivered to the cells, an electroporation device for introduction of the nucleic acids into the cells, and a processor-based system configured to operate the instrument based on user input.

In some aspects, the instruments of the disclosure further comprise a cell growth unit. In other aspects, the instruments of the disclosure further comprise a cell selection unit. In yet other aspects, the instruments of the disclosure further comprise a cell concentration unit. In still other aspects, the instruments of the disclosure further comprise both a cell growth and a cell concentration unit. In specific aspects, the instruments of the disclosure further comprise a cell growth unit, a cell selection module and a cell concentration unit. Each of the instruments may also optionally contain a cell wash function and an optional storage module for storage of the cells following transformation.

Accordingly, in one specific embodiment, the disclosure provides an instrument for automated live cell electroporation, comprising: a receptacle configured to receive nucleic acids to be assembled and delivered to the cells, an assembly module for the assembly of nucleic acids to be transformed into the cells; a purification module to remove unwanted components of the nucleic acid assembly; a receptacle configured to receive live cells; an electroporation device for introduction of the assembled nucleic acids into the cells, and a processor-based system configured to operate the instrument based on user input.

In other specific aspects, the disclosure provides an instrument for automated live cell electroporation, comprising a receptacle configured to receive live cells; a receptacle configured to receive nucleic acids; an assembly module for assembly of the nucleic acids prior to transformation; an electroporation device for introduction of the nucleic acids into the cells; and a processor-based system configured to operate the instrument based on user input.

In some aspects, the instruments of the disclosure further comprise a cell growth unit. In other aspects, the instruments of the disclosure further comprise a cell selection unit. In yet other aspects, the instruments of the disclosure further comprise a cell concentration unit. In still other aspects, the instruments of the disclosure further comprise both a cell growth and a cell concentration unit. In specific aspects, the instruments of the disclosure further comprise a cell growth unit, a cell selection module and a cell concentration unit. Each of the instruments may also optionally contain a cell wash function and an optional storage module for storage of the cells following transformation. a combination reagent cartridge and electroporation device configured for use in an automated multi-module cell processing environment. The reagent cartridges include an electroporation device, as well as sample receptacles, reagent receptacles, waste receptacles and the like, and a script for controlling a processor to dispense samples and reagents contained in the receptacles, and to porate cells in the electroporation device. Also described are kits including the cartridges, automated instruments including the reagent cartridges and methods of using the reagent cartridges.

Thus, presented herein is an exemplary embodiment of an automated instrument comprising a reagent cartridge comprising a plurality of reagent reservoirs, a flow-through electroporation device, and a script readable by a processor for dispensing reagents located in the plurality of reagent reservoirs and controlling the electroporation device, wherein the script comprises commands for retrieving reagents in the reagent cartridge and commands for electroporating cells in the flow-through electroporation device.

In some aspects of this embodiment, the flow-through electroporation device comprises an inlet and inlet channel for introduction of a cell sample to the flow-through electroporation (FTEP) device; an outlet and outlet channel for exit of the cell sample from the FTEP device; a constricted flow channel intersecting and positioned between the inlet channel and outlet channel; and two or more electrodes, wherein the two or more electrodes are (a) positioned in the flow channel between the intersection of the flow channel with the first inlet channel and the intersection of the flow channel with the outlet channel and on either side of the constriction in the flow channel, (b) in fluid communication with the cell sample in the flow channel but are not in the flow path of the cell sample in the flow channel, and (c) configured to apply an electric pulse or electric pulses to a cell sample.

Also in some aspects the script readable by a processor comprises commands for performing one or more additional processes in the automated instrument, and in some aspects, the script readable by a processor comprises commands for performing all processes in the automated instrument.

In some aspects of this embodiment, the automated instrument further comprises a cell growth module, and in some aspects, the cell growth module comprises a rotating growth vial.

In some aspects the automated instrument further comprises a filtration module, and in some aspects, the filtration module comprises a hollow fiber filter.

The automated instrument may also further comprise a recovery module, and in some aspects the recovery module comprises a cell growth module comprising a rotating growth vial.

In some aspects, the automated instrument further comprises a storage module, and/or a nucleic acid assembly module, where in some aspects the nucleic acid assembly module is a Gibson assembly module or a Gap Repair module.

In some aspects the automated instrument further comprises a processor to read the script.

Another embodiment of an automated instrument presented herein comprises a reagent cartridge comprising a plurality of reagent reservoirs, a flow-through electroporation device, wherein the flow-through electroporation device comprises an inlet and inlet channel for introduction of a cell sample to the flow-through electroporation device; an outlet and outlet channel for exit of the cell sample from the flow-through electroporation device; a flow channel intersecting and positioned between the inlet channel and outlet channel; and two or more electrodes, wherein the two or more electrodes are (a) positioned in the flow channel between the intersection of the flow channel with the first inlet channel and the intersection of the flow channel with the outlet channel, (b) in fluid communication with the cell sample in the flow channel but are not in the flow path of the cell sample in the flow channel, and (c) configured to apply an electric pulse or electric pulses to a cell sample.

In some aspects the automated instrument further comprises a script readable by a processor wherein the script comprises commands for retrieving reagents in the reagent cartridge and commands for electroporating cells in the electroporation device. In some aspects, the script readable by a processor comprises commands for performing one or more additional processes in the automated instrument, and in some aspects, the script readable by a processor comprises commands for performing all processes in the automated instrument.

In some aspects, the automated instrument further comprises a cell growth module, and in some aspects, the cell growth module comprises a rotating growth vial. The automated instrument may also comprise a filtration module, where the filtration module comprises a hollow fiber filter.

The automated instrument may also comprise a recovery module, where the recovery module comprises a cell growth module comprising a rotating growth vial.

In some aspects the automated instrument further comprises a storage module, and/or a nucleic acid assembly module, where the nucleic acid assembly module is a Gibson assembly module or a Gap Repair module.

In many aspects, the automated instrument further comprises a processor to read the script.

Yet another embodiment of an automated instrument presented herein comprises a reagent cartridge comprising a plurality of reagent reservoirs; a flow-through electroporation device, wherein the flow-through electroporation device comprises an inlet and inlet channel for introduction of a cell sample to the flow-through electroporation device; an outlet and outlet channel for exit of the cell sample from the flow-through electroporation device; a constricted flow channel intersecting and positioned between the inlet channel and outlet channel; and two or more electrodes, wherein the two or more electrodes are (a) positioned in the flow channel between the intersection of the flow channel with the first inlet channel and the intersection of the flow channel with the outlet channel and on either side of the constriction in the flow channel, (b) in fluid communication with the cell sample in the flow channel but are not in the flow path of the cell sample in the flow channel, and (c) configured to apply an electric pulse or electric pulses to a cell sample; and a script readable by a processor wherein the script comprises commands for retrieving reagents in the reagent cartridge and commands for electroporating cells in the electroporation device.

And yet another embodiment provides a kit for use in the automated instruments comprising a reagent cartridge, where the reagent cartridge further comprises reagents dispensed in one or more of the reagent reservoirs. In some aspects, the one or more reagent reservoirs with reagents dispensed therein is sealed. Also in some aspects, the reagent cartridge comprises a cover for the reagent cartridge.

In some aspects, the reagent cartridge of the kit comprises cells dispensed in one or more reagent reservoirs, and in some aspects, the kit comprises an enzyme mix for a Gibson assembly reaction or a Gap Repair reaction dispensed in one or more reagent reservoirs, and/or nucleic acid vectors and/or oligonucleotides dispensed in one or more reagent reservoirs. The kit may also comprise a rotating growth vial with media and cells dispensed therein.

In addition, provided herein is an automated instrument comprising a reagent cartridge comprising a plurality of reagent reservoirs; an (FTEP) device for introducing an nucleic acid into cells in a fluid, where the FTEP device comprises: at least one inlet and at least one inlet channel for introducing a fluid comprising cells and nucleic acid to the FTEP device; an outlet and an outlet channel for removing transformed cells and nucleic acid from the FTEP device; a flow channel positioned between a first inlet channel and the outlet channel, wherein the flow channel intersects with the first inlet channel and the outlet channel and wherein a portion of the flow channel narrows between the inlet channel intersection and the outlet channel intersection; and an electrode positioned on either side of the flow channel and in direct contact with the fluid in the flow channel, the electrodes defining the narrowed portion of the flow channel, and wherein the electrodes apply one or more electric pulses to the cells in the fluid as they pass through the flow channel, thereby introducing the nucleic acid into the cells in the fluid.

In some aspects of this embodiment, the electrodes are positioned on either side of the flow channel, are in direct contact with the fluid in the flow channel and define the decrease in width of the flow channel. In some configurations of this aspect, the electrodes are between 10 µm to 5 mm apart, or between 25 µm to 2 mm apart.

In some aspects of these embodiments, the FTEP device is between 3 cm to 15 cm in length, or between 4 cm to 12 cm in length, or from 4.5 cm to 10 cm in length, or from 5 cm to 8 cm in length. In some aspects of these embodiments, this embodiment of the FTEP device is between 0.5 cm to 5 cm in width, or from 0.75 cm to 3 cm in width, or from 1 cm to 2.5 cm in width, or from 1 cm to 1.5 cm in width. In some aspects of these embodiments, the narrowest part of the channel width in the FTEP device is from 10 µM to 5 mm such that whatever cell type is being transformed will not be physically contorted or "squeezed" by features of the FTEP device.

Also in some aspects of these embodiments, the flow rate in the FTEP ranges from 0.1 ml to 5 ml per minute, or from 0.5 ml to 3 ml per minute, or from 1 ml to 2.5 ml per minute. In some aspects of these embodiments the electrodes are configured to deliver 1-25 Kv/cm, or 10-20 Kv/cm.

In some aspects of these embodiments, the FTEP device further comprises one or more filters between the one or more inlet channels and the outlet channel. In some aspects, there are two filters, one between the inlet channel and the narrowed portion of the flow channel, and one between the narrowed portion of the flow channel and the outlet channel. In some aspects of these embodiments, the filters are graduated in pore size with the larger pores proximal to the inlet chamber or outlet chamber, and the small pores proximal to the narrowed portion of the flow channel. In some aspects, the small pores are the same size or larger than the size of the narrowed portion of the flow channel. In some aspects of these embodiments, the filter is formed separately from the body of the FTEP device and placed into the FTEP device as it is being assembled. Alternatively, in some aspects of these embodiments, the filter may be formed as part of and integral to the body of the FTEP device.

In some aspects of these embodiments, the FTEP device further comprises a reservoir connected to the inlet for introducing the cells in fluid into the FTEP device and a reservoir connected to the outlet for removing transformed cells from the FTEP device, and in some aspects, the FTEP device comprises two inlets and two inlet channels and further comprises a reservoir connected to a second inlet for introducing the nucleic acid into the FTEP device. In some aspects the FTEP device comprises a reservoir connected to the inlet for introducing both the cells in fluid and the nucleic acid into the FTEP device and a reservoir connected to the outlet for removing transformed cells from the FTEP device In some aspects of these embodiments, the reservoirs coupled to the inlet(s) and outlet range in volume from 100 µL to 10 ml, or from 0.5 ml to 7 ml, or from 1 ml to 5 ml.

In some aspects of these embodiments, the FTEP devices can provide a cell transformation rate of $10^3$ to $10^{12}$ cells per minute, or $10^4$ to $10^{10}$ per minute, or $10^5$ to $10^9$ per minute, or $10^6$ to $10^8$ per minute. Typically, $10^8$ yeast cells may be transformed per minute, and $10^{10}$-$10^{11}$ bacterial cells may be transformed per minute. In some aspects of these embodiments, the transformation of cells results in at least 90% viable cells, or 95% viable cells, and up to 99% viable cells.

In some aspects of these embodiments, the FTEP device is manufactured by injection molding from crystal styrene, cyclo-olefin polymer, or cyclo-olefin co-polymer, and in some aspects of this embodiment the electrodes are fabricated from stainless steel. In some aspects of these embodiments, the FTEP devices are fabricated as multiple FTEP devices in parallel on a single substrate where the FTEP devices are then separated for use.

In some embodiments of the automated multi-module cell processing system of which the FTEP is a part, the nucleic acids in the one or more receptacles comprise a vector backbone and an oligonucleotide, and the automated instrument further comprises a nucleic acid assembly module. In some aspects, the nucleic acid assembly module comprises a magnet, and in some aspects, the nucleic acid assembly module is configured to perform nucleic acid assembly using a single, isothermal reaction. In other aspects, the nucleic acid assembly module is configured to perform an amplification and/or ligation method. In some aspects, the nucleic acid assembly module also comprises means for isolating, washing, concentrating, diluting and/or resuspending the assembled nucleic acids.

In some embodiments, the automated instrument comprising the FTEP may further comprise a growth module configured to grow the cells, and in some implementations, the growth module measures optical density of the growing cells, either continuously or at intervals. In some implementations, a processor controlling the instrument is configured to adjust growth conditions in the growth module such that the cells reach a target optical density at a time requested by a user. Further, in some embodiments, the user may be updated regarding growth process, e.g. through a user interface of the automated instrument or through a portable computing device application in communication with the automated instrument.

In some embodiments, the automated instrument comprising the FTEP also comprises a reagent cartridge with one or more receptacles configured to receive cells and one or more receptacles configured to receive nucleic acids. In some embodiments, the automated instrument comprising the FTEP also comprises a reagent cartridge with one or more receptacles configured to receive both cells and nucleic acids. Further, the reagent cartridge may also contain some or all reagents required for cell manipulation following transformation, e.g., an antibiotic for selection of transformed cell or an inducer for protein expression. In some implementations, the reagents contained within the reagent cartridge are locatable by a script read by the processor, and in some implementations, the reagent cartridge includes reagents and is provided in a kit. In some embodiments, the FTEP device (e.g., transformation module) is contained within the reagent cartridge.

Some embodiments of the automated instrument further comprise a filtration module configured to exchange the liquid medium in which the cells are suspended and/or concentrate the cells. In specific aspects, the script comprises commands to alert a user that a target OD has been reached by the cell growth module, and/or the script comprises commands to adjust the growth temperature of cells to reach a target OD at a target time.

In certain aspects, the nucleic acids are nucleic acids, and the instrument further comprises a cell expression module, e.g., for the expression of proteins encoded on the nucleic acids introduced to the transformed cell populations.

In other aspects, the instrument may contain two or more electroporation devices for performing two or more transformation events in a single instrument operation.

Other features, advantages, and aspects will be described below in more detail.

BRIEF DESCRIPTION OF THE DRAWINGS

The accompanying drawings, which are incorporated into and constitute a part of the specification, illustrate one or more embodiments and, together with the description, explain these embodiments. The accompanying drawings have not necessarily been drawn to scale. Any dimensions illustrated in the accompanying graphs and figures are for illustration purposes only and may or may not represent actual or preferred values or dimensions. Where applicable, some or all features may not be illustrated to assist in the description of underlying features. In the drawings:

FIGS. 2A and 2B depict side and front views of the automated instrument for introducing nucleic acids into cells. FIGS. 2C and 2D depict a second example chassis of an automated instrument for introducing nucleic acids into cells.

FIG. 4G is an illustration of a top view of yet another embodiment of the FTEP devices of the disclosure. FIG. 4H is an illustration of the top view of a cross section of the embodiment of the device shown in FIG. 4G. FIG. 4I is an illustration of a side view of a cross section of the embodiment of the device shown in FIGS. 4G and 4H.

DETAILED DESCRIPTION OF ILLUSTRATIVE EMBODIMENTS

Figure 1:
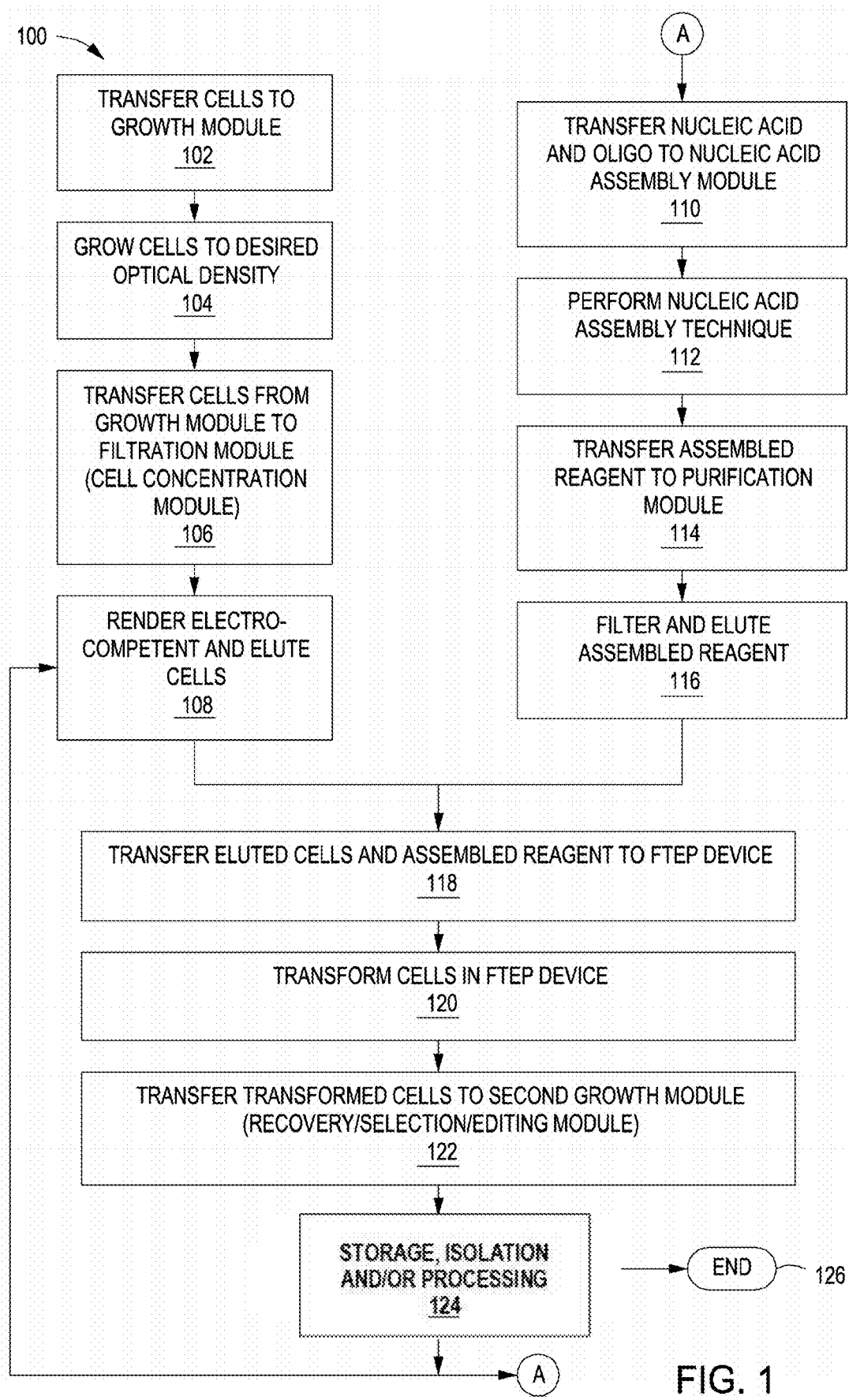
FIG. 1 is a flow chart for an example method for automated introduction of nucleic acids.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include synthesis, assembly, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, *"Oligonucleotide Synthesis: A Practical Approach"* 1984, IRL Press, London; Nelson and Cox (2000), *Lehninger, Principles of Biochemistry* $3^{rd}$ Ed., W.H. Freeman Pub., New York, N.Y.; Berg et al. (2002) *Biochemistry*, $5^{th}$ Ed., W.H. Freeman Pub., New York, N.Y.; *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011), all of which are herein incorporated in their entirety by reference for all purposes. CRISPR-specific techniques can be found in, e.g., *Genome Editing and Engineering From TALENs and CRISPRs to Molecular Surgery*, Appasani and Church, 2018; and *CRISPR: Methods and Protocols*, Lindgren and Charpentier, 2015; both of which are herein incorporated in their entirety by reference for all purposes.

Note that as used herein and in the appended claims, the singular forms "a," "an," and "the" include plural referents unless the context clearly dictates otherwise. Thus, for example, reference to "an oligo" refers to one or more oligos that serve the same function, to "the methods" includes reference to equivalent steps and methods known to those skilled in the art, and so forth. That is, unless expressly specified otherwise, as used herein the words "a," "an," "the" carry the meaning of "one or more." Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration.

Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "proximate," "minor," and similar terms generally refer to ranges that include the identified value within a margin of 20%, 10% or preferably 5% in certain embodiments, and any values therebetween.

Unless defined otherwise, all technical and scientific terms used herein have the same meaning as commonly understood by one of ordinary skill in the art to which this disclosure belongs.

All publications (including patents, published applications, and non-patent literature) mentioned herein are incorporated by reference for all purposes, including but not limited to the purpose of describing and disclosing devices, systems, and methods that may be used or modified in connection with the presently described methods, modules, instruments, and systems.

Where a range of values is provided, it is understood that each intervening value, between the upper and lower limit of that range and any other stated or intervening value in that stated range is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either both of those included limits are also included in the disclosure.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment.

Further, the particular features, structures or characteristics may be combined in any suitable manner in one or more embodiments. Further, it is intended that embodiments of the disclosed subject matter cover modifications and variations thereof.

Introduction and Overview

The present disclosure provides automated instruments comprising FTEP devices for the automated introduction of nucleic acids into living cells. In some embodiments, the automated instruments include both an FTEP module and a nucleic acid assembly modules to introduction of an oligonucleotide or nucleic acid of interest into a vector backbone that controls expression or other control of the oligonucleotide or nucleic acid. Each system described herein has advantages and challenges, and the particular system that can be used in the inventions of the disclosure can be selected for the particular application, as will be apparent to one of ordinary skill in the art upon reading the present disclosure.

The cells that can be transformed or transfected using the automated instrument comprising the FTEP devices include any prokaryotic, archaeal or eukaryotic cell. For example, prokaryotic cells for use with the present illustrative embodiments can be gram positive bacterial cells, e.g., *Bacillus subtilis*, or gram negative bacterial cells, e.g., *E. coli* cells. Eukaryotic cells for use with the automated instruments of the illustrative embodiments include any plant cells and any animal cells, e.g. fungal cells, insect cells, amphibian cells, nematode cells, or mammalian cells.

FIG. 1 is a flow chart for an example method 100 for automated introduction of nucleic acids. In a first step 102, cells of interest are transferred to a growth module (as described in detail below), where the cells are grown to a desired optical density 104. The cells are then transferred from the growth module to a filtration module 106, wherein the cells are concentrated, and in certain embodiments, concurrently the cells are rendered electrocompetent 108. Optionally in a parallel process A, nucleic acids (such as, e.g., a vector backbone and an expression cassette) are transferred 110 to a nucleic acid assembly module (also as described in detail below) where assembly of the, e.g., expression cassette into the vector backbone is performed 112. Once the nucleic acid assembly has been accomplished, the assembled nucleic acids are transferred 114 to a purification module, where the nucleic acids are, e.g., de-salted, washed, and/or sorted (e.g., where assembled nucleic acids are separated from unassembled vectors and expression cassettes). After purification, the assembled nucleic acids are filtered and eluted 116. At this point, the concentrated and electrocompetent cells and the assembled nucleic acids are transferred 118 to the FTEP device, where the cells are transformed or transfected 120 with the assembled nucleic acids. Following transformation, the cells may be transferred 122 to a second growth module where the cells are allowed to recover. In the second growth module, there may be selective medium to select for transformed cells, or the cells may be subjected to, e.g., cell editing or protein expression. Next, the cells may be moved 124 to a storage, isolation, and/or processing module. In some aspects, the cells may go through another cycle of processing (e.g., repeating steps 108, 118, 120, 122, 124 with another set of assembled nucleic acids via process A), or the cells may be removed and used in further experiments or analysis 126.

Instrument Architecture

FIGS. 2A through 2D illustrate example chassis 200 and 230 for use in desktop versions of an automated multi-module cell processing instrument. For example, the chassis 200 and 230 may have a width of about 24-48 inches, a height of about 24-48 inches and a depth of about 24-48 inches. Each of the chassis 200 and 230 may be designed to hold multiple modules and disposable supplies used in automated cell processing. Further, each chassis 200 and 230 may mount a robotic handling system for moving materials between modules.

FIGS. 2A and 2B depict a first example chassis 200 of an automated multi-module cell processing instrument. As illustrated, the chassis 200 includes a cover 202 having a handle 204 and hinges 206a-206c for lifting the cover 202 and accessing an interior of the chassis 200. A cooling grate 214 may allow for air flow via an internal fan (not shown). Further, the chassis 200 is lifted by adjustable feet 220. The feet 220a-220c, for example, may provide additional air flow beneath the chassis 200. A control button 216, in some embodiments, allows for single-button automated start and/or stop of cell processing within the chassis 200.

Inside the chassis 200, in some implementations, a robotic handling system 208 is disposed along a gantry 210s or 210b above materials cartridges 212a, 212b. Control circuitry, liquid handling tubes, air pump controls, valves, thermal units (e.g., heating and cooling units) and other control mechanisms, in some embodiments, are disposed below a deck of the chassis 200, in a control box region 218.

Although not illustrated, in some embodiments a display screen may be positioned upon a front face of the chassis 200, for example covering a portion of the cover 202. The display screen may provide information to the user regarding a processing status of the automated multi-module cell processing instrument. In another example, the display screen may accept inputs from the user for conducting the cell processing.

FIGS. 2C and 2D depict a second example chassis 230 of an automated multi-module cell processing instrument. The chassis 230, as illustrated, includes a transparent door 232 with a hinge 234. For example, the door may swing to the left of the page to provide access to a work area of the chassis. The user, for example, may open the transparent door 232 to load supplies, such as reagent cartridges and wash cartridges, into the chassis 230.

In some embodiments, a front face of the chassis 230 further includes a display (e.g., touch screen display device) 236 illustrated to the right of the door 232. The display 236 may provide information to the user regarding a processing status of the automated multi-module cell processing instrument. In another example, the display 236 may accept inputs from the user, e.g., for pausing or conducting the cell processing.

An air grate 238 on a right face of the chassis 230 may provide for air flow within a work area (e.g., above the deck) of the chassis 230 (e.g., above a deck). A second air grate 240 on a left of the chassis 230 may provide for air flow within a control box region 242 (e.g., below the deck) of the chassis 230. Although not illustrated, in some embodiments, feet such as the feet 220a-220c of the chassis 200 may raise the chassis 230 above a work surface, providing for further air flow.

Inside the chassis 230, in some implementations, a robotic handling system 248 is disposed along a gantry 250 above cartridges 252a, 252b, material supplies 254a, 254b (e.g., pipette tips and filters), and modules (e.g., dual growth vials, FTEP device, nucleic acid assembly module (not shown)). Control circuitry, liquid handling tubes, air pump controls, valves, and other control mechanisms, in some embodiments, are disposed below a deck of the chassis 230, in the control box region 242.

In some embodiments, a liquid waste unit 246 is mounted to the left exterior wall of the chassis 230. The liquid waste unit 246, for example, may be mounted externally to the chassis 230 to avoid potential contamination and to ensure prompt emptying and replacement of the liquid waste unit 246.

Nucleic Acid Assembly Module

Certain embodiments of the automated instruments of the present disclosure include a nucleic acid assembly module instrument. The nucleic acid assembly module is configured to accept and assemble the nucleic acids necessary to facilitate the desired genome manipulations. The nucleic acid assembly module may also be configured to accept the appropriate vector backbone for vector assembly and subsequent electroporation into the cells of interest.

In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that include one or more free ends, no free ends (e.g. circular); nucleic acid molecules that include DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, where virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids. Additional vectors include fosmids, phagemids, and synthetic chromosomes.

Recombinant expression vectors can include a nucleic acid in a form suitable for transformation, and for some nucleic acid sequences, translation and expression of the nucleic acid in a host cell, which means that the recombinant expression vectors include one or more regulatory elements—which may be selected on the basis of the host cells to be used for expression—that are operatively-linked to the nucleic acid sequence to be expressed. Within a recombinant expression vector, "operably linked" is intended to mean that the nucleotide sequence of interest is linked to the regulatory element(s) in a manner that allows for transcription, and for some nucleic acid sequences, translation and expression of the nucleotide sequence (e.g. in an in vitro transcription/translation system or in a host cell when the vector is introduced into the host cell). Appropriate recombination and cloning methods are disclosed in U.S. patent application Ser. No. 10/815,730, entitled "Recombinational Cloning Using Nucleic Acids Having Recombination Sites" published Sep. 2, 2004 as US 2004-0171156 A1, the contents of which are herein incorporated by reference in their entirety for all purposes.

In some embodiments, a regulatory element is operably linked to one or more elements of a targetable nuclease system so as to drive transcription, and for some nucleic acid sequences, translation and expression of the one or more components of the targetable nuclease system.

In addition, the polynucleotide sequence encoding the nucleic acid-guided nuclease can be codon optimized for expression in particular cells, such as prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammal including non-human primate. In addition or alternatively, a vector may include a regulatory element operably liked to a polynucleotide sequence, which, when transcribed, forms a guide RNA.

The nucleic acid assembly module can be configured to perform a wide variety of different nucleic acid assembly techniques in an automated fashion. Nucleic acid assembly techniques that can be performed in the nucleic acid assembly module of the disclosed automated instruments include, but are not limited to, those assembly methods that use restriction endonucleases, including PCR, BioBrick assembly (U.S. Pat. No. 9,361,427 to Hillson entitled "Scar-less Multi-part DNA Assembly Design," issued Jun. 7, 2016), Type IIS cloning (e.g., GoldenGate assembly; European Patent Application Publication EP 2 395 087 A1 to Weber et al. entitled "System and Method of Modular Cloning," filed Jul. 6, 2010), and Ligase Cycling Reaction (de Kok S, ACS Synth Biol., 3(2):97-106 (2014); Engler, et al., PLoS One, 3(11):e3647 (2008); U.S. Pat. No. 6,143,527 to Pachuk et al. entitled "Chain Reaction Cloning Using a Bridging Oligonucleotide and DNA Ligase," issued Nov. 7, 2000). In other embodiments, the nucleic acid assembly techniques performed by the disclosed automated instruments are based on overlaps between adjacent parts of the nucleic acids, such as Gibson Assembly®, CPEC, SLIC, Ligase Cycling etc. Additional assembly methods include gap repair in yeast (Bessa, Yeast, 29(10):419-23 (2012)), gateway cloning (Ohtsuka, Curr Pharm Biotechnol, 10(2):244-51(2009); U.S. Pat. No. 5,888,732 to Hartley et al., entitled "Recombinational Cloning Using Engineered Recombination Sites," issued Mar. 30, 1999; U.S. Pat. No. 6,277,608 to Hartley et al. entitled "Recominational Cloning Using Nucleic Acids Having Recombination Sites," issued Aug. 21, 2001), and topoisomerase-mediated cloning (Udo, PLoS One, 10(9): e0139349 (2015); U.S. Pat. No. 6,916,632 B2 to Chestnut et al. entitled "Methods and Reagents for Molecular Cloning," issued Jul. 12, 2005). These and other nucleic acid assembly techniques are described, e.g., in Sands and Brent, Curr Protoc Mol Biol., 113:3.26.1-3.26.20 (2016); Casini et al., Nat Rev Mol Cell Biol., (9):568-76 (2015); Patron, Curr Opinion Plant Biol., 19:14-9 (2014)).

The nucleic acid assembly module is temperature controlled depending upon the type of nucleic acid assembly used in the automated instrument. For example, when PCR is utilized in the nucleic acid assembly module, the module will have a thermocycling capability allowing the temperatures to cycle between denaturation, annealing and extension. When single temperature assembly methods are utilized in the nucleic acid assembly module, the module will have the ability to reach and hold at the temperature that optimizes the specific assembly process being performed. These temperatures and the duration for maintaining these temperatures can be determined by a preprogrammed set of parameters executed by a script, or manually controlled by the user using the processing system of the automated instrument.

Figure 3:
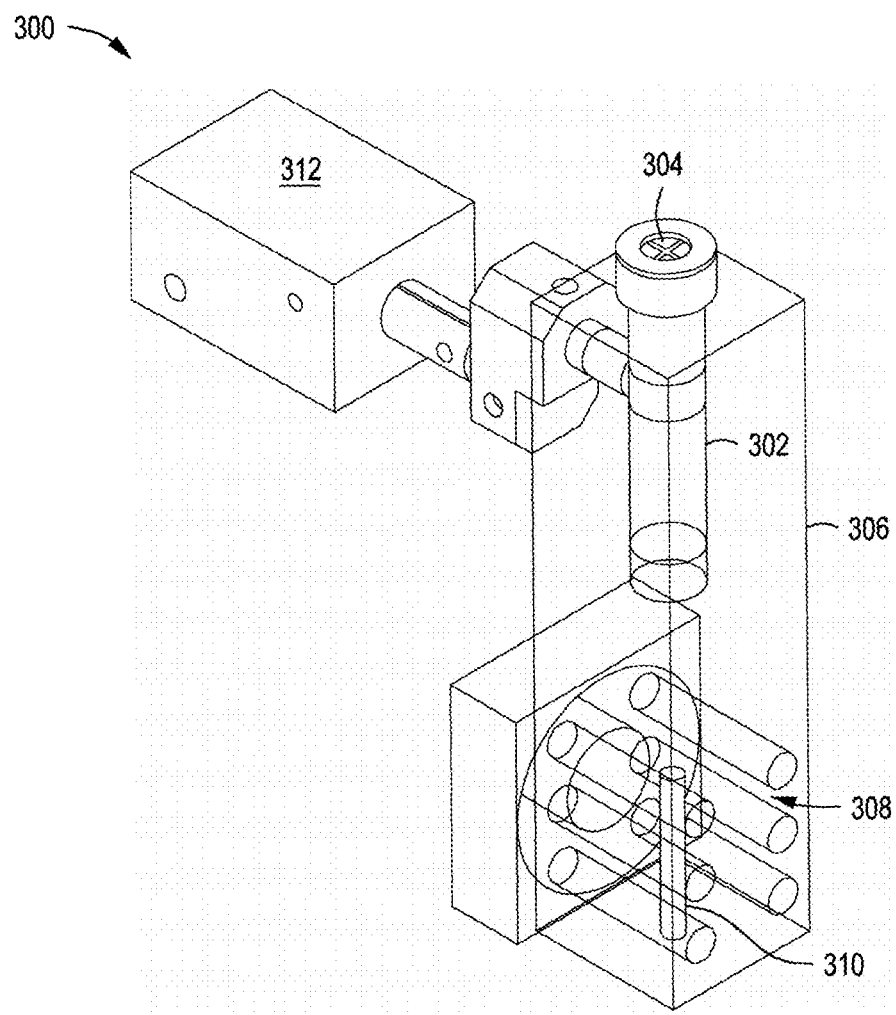
FIG. 3 depicts an example combination nucleic acid assembly module and purification module for use in an automated instrument.

In one embodiment, the nucleic acid assembly module is a module to perform assembly using a single, isothermal reaction, such as that illustrated in FIG. 3. The isothermal assembly module is configured to perform the molecular cloning method using the single, isothermal reaction. Certain isothermal assembly methods can combine simultaneously up to 15 nucleic acid fragments based on sequence identity. The assembly method provides, in some embodiments, nucleic acids to be assembled which include an approximate 20-40 base overlap with adjacent nucleic acid fragments. The fragments are mixed with a cocktail of three enzymes—an exonuclease, a polymerase, and a ligase-along with buffer components. Because the process is isothermal and can be performed in a 1-step or 2-step method using a single reaction vessel, isothermal assembly reactions are ideal for use in an automated instrument. The 1-step method allows for the assembly of up to five different fragments using a single step isothermal process. The fragments and the master mix of enzymes are combined and incubated at 50° C. for up to one hour. For the creation of more complex constructs with up to fifteen fragments or for incorporating fragments from 100 bp up to 10 kb, typically the 2-step is used, where the 2-step reaction requires two separate additions of master mix; one for the exonuclease and annealing step and a second for the polymerase and ligation steps.

FIG. 3 illustrates an example nucleic acid assembly module 300 with integrated purification. The nucleic acid assembly module 300 includes a chamber 302 having an access gasket 304 for transferring liquids to and from the nucleic acid assembly module 300 (e.g., via a pipette or sipper). In some embodiments, the access gasket 304 is connected to a replaceable vial which is positioned within the chamber 302. For example, a user or robotic manipulation system may place the vial within the nucleic acid assembly module 300 for processing.

The chamber 302 shares a housing 306 with a resistive heater 308. Once a sample has been introduced to the chamber 302 of the nucleic acid assembly module 300, the resistive heater 308 may be used to heat the contents of the chamber 302 to a desired temperature. Thermal ramping may be set based upon the contents of the chamber 302 (e.g., the materials supplied through the access gasket 304 via pipettor or sipper unit of the robotic manipulation system). The processing system of the automated instrument may determine the target temperature and thermal ramping plan. The thermal ramping and target temperature may be controlled through monitoring a thermal sensor such as a thermistor 310 included within the housing 306. In a particular embodiment, the resistive heater 308 is designed to maintain a temperature within the housing 306 of between 20° and 80° C., between 25° and 75° C., between 37° and 65° C., between 40° and 60° C., between 45° and 55° C. or preferably about 50° C.

Purification Module

In some embodiments, when a nucleic acid assembly module is included in the automated instrument, the instrument also can include a purification module to remove unwanted components of the nucleic acid assembly mixture (e.g., salts, minerals) and, in certain embodiments, concentrate the assembled nucleic acids. Examples of methods for exchanging the liquid following nucleic acid assembly include magnetic beads (e.g., SPRI or Dynal (Dynabeads) by Invitrogen Corp. of Carlsbad, Calif.), silica beads, silica spin columns, glass beads, precipitation (e.g., using ethanol or isopropanol), alkaline lysis, osmotic purification, extraction with butanol, membrane-based separation techniques, filtration etc.

In one aspect, the purification module provides filtration, e.g., ultrafiltration. For example, a range of microconcentrators fitted with anisotropic, hydrophilic-generated cellulose membranes of varying porosities is available. In another example, the purification and concentration involves contacting a liquid sample including the assembled nucleic acids and an ionic salt with an ion exchanger including an insoluble phosphate salt, removing the liquid, and eluting the nucleic acid from the ion exchanger.

In a specific aspect of the purification module, SPRI beads can be used where 0.6-2.0× volumes of SPRI beads can be added to the nucleic acid assembly. The nucleic acid assembly product becomes bound to the SPRI beads, and the SPRI beads are pelleted by automatically positioning a magnet close to the tube, vessel, or chamber harboring the pellet. For example, 0.6-2.0× volumes of SPRI beads can be added to the nucleic acid assembly. The SPRI beads, for example, may be washed with ethanol, and the bound nucleic acid assembly product is eluted, e.g., in water, Tris buffer, or 10% glycerol.

In a specific aspect, a magnet is coupled to a linear actuator that positions the magnet. In some implementations, the nucleic acid assembly module is a combination assembly and purification module designed for integrated assembly and purification. For example, as discussed above in relation to the nucleic acid assembly module depicted in FIG. 3, once sufficient time has elapsed for the nucleic acid assembly reaction to take place, the contents of the chamber 302 (e.g., the nucleic acid assembly reagents and nucleic acids), in some embodiments, are combined with magnetic beads (not shown) to activate the purification process. The SPRI beads in buffer are delivered to the contents of the nucleic acid assembly module, for example, by a robotic handling system. Thereafter, a solenoid 312, in some embodiments, is actuated by a magnet to excite the magnetic beads contained within the chamber 302. The solenoid, in a particular example, may impart between a 2 pound magnetic pull force and a 5 pound pull force, or approximately a 4 pound magnetic pull force to the magnetic beads within the chamber 302. The contents of the chamber 302 may be incubated for sufficient time for the assembled vector and oligonucleotides to bind to the magnetic beads.

After binding, in some implementations, the bound nucleic acid assembly mix (e.g., isothermal nucleic acid assembly reagents+assembled vector and oligonucleotides) is removed from the nucleic acid assembly module and the nucleic acids attached to the beads are washed one to several times with 80% ethanol. Once washed, the nucleic acids attached to the beads are eluted into buffer and are transferred to the transformation module. That is, in some embodiments, the nucleic acid assembly module and purification module are combined.

In some implementations, a vial is locked in position in the chamber 302 for processing. For example, a user may press the vial beyond a detent in the chamber 302 designed to retain the vial upon engagement with a pipettor or sipper. In another example, the user may twist the vial into position, thus engaging a protrusion to a corresponding channel and barring upward movement. A position sensor (not illustrated) may ensure retraction of the vial. The position sensor, in a particular embodiment, is a magnetic sensor detecting engagement between a portion of the chamber 302 and the vial. In other embodiments, the position sensor is an optical sensor detecting presence of the vial at a retracted position. In embodiments using a channel and protrusion, a mechanic switch pressed down by the protrusion may detect engagement of the vial.

Growth Module

As the nucleic acids are being assembled, the cells may be grown in preparation for transformation/transfection. Cell growth can be monitored by optical density (e.g., at OD 600 nm) that is measured in a growth module, and a feedback loop is used to adjust the cell growth so as to reach a target OD at a target time. Other measures of cell density and physiological state that can be measured include but are not limited to, pH, dissolved oxygen, released enzymes, acoustic properties, and electrical properties.

In some aspects, the growth module includes a culture tube in a shaker or vortexer that is interrogated by a spectrophotometer or fluorimeter. The shaker or vortexer can heat or cool the cells and cell growth is monitored by real-time absorbance or fluorescence measurements. In one aspect, the cells are grown at 25° C.-40° C. to an OD600 absorbance of 1-10 ODs. The cells may also be grown at temperature ranges from 25° C.-35° C., 25° C.-30° C., 30° C.-40° C., 30° C.-35° C., 35° C.-40° C., 40° C.-50° C., 40° C.-45° C. or 44° C.-50° C. In another aspect, the cells are induced by heating at 42° C.-50° C. or by adding an inducing agent. The cells may also be induced by heating at ranges from 42° C.-46° C., 42° C.-44° C., 44° C.-46° C., 44° C.-48° C., 46° C.-48° C., 46° C.-50° C., or 48° C.-50° C. In some aspects, the cells are cooled to 0° C.-10° C. after induction. The cells may also be cooled to temperature ranges of 0° C.-5° C., 0° C.-2° C., 2° C.-4° C., 4° C.-6° C., 6° C.-8° C., 8° C.-10° C., or 5° C.-10° C. after induction.

Figure 13A:
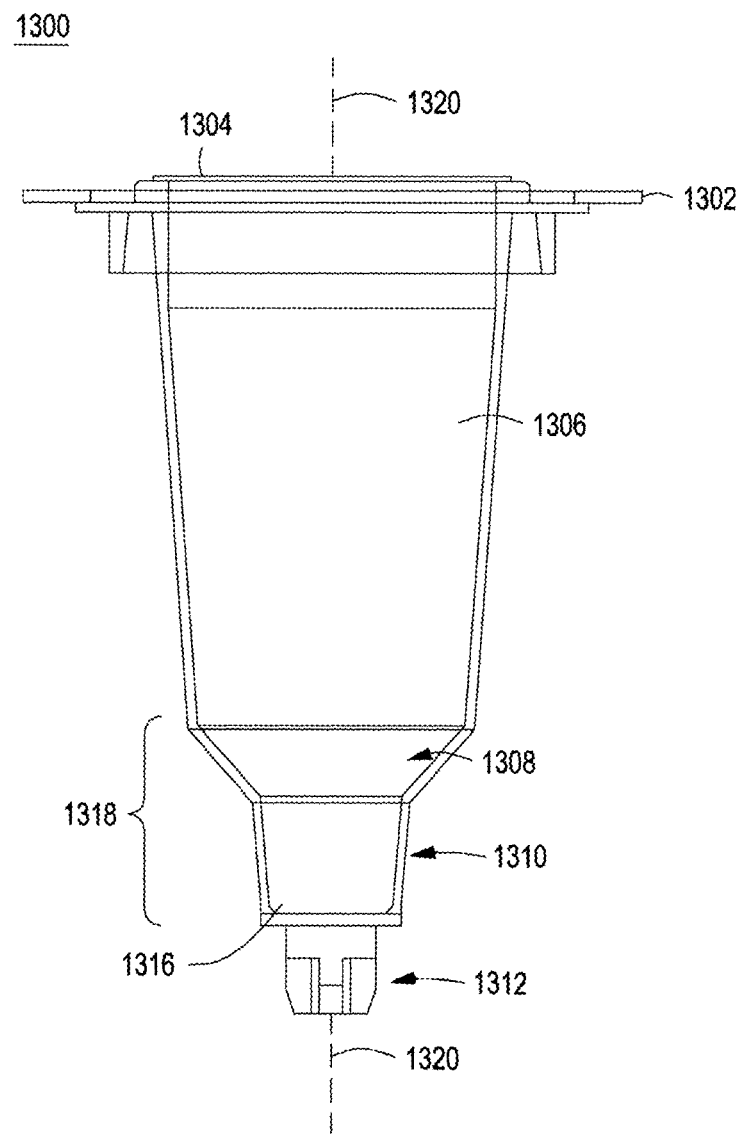
FIGS. 13A-13C depict example cell growth module components for use in an automated instrument for introduction of nucleic acids.
Figure 13B:
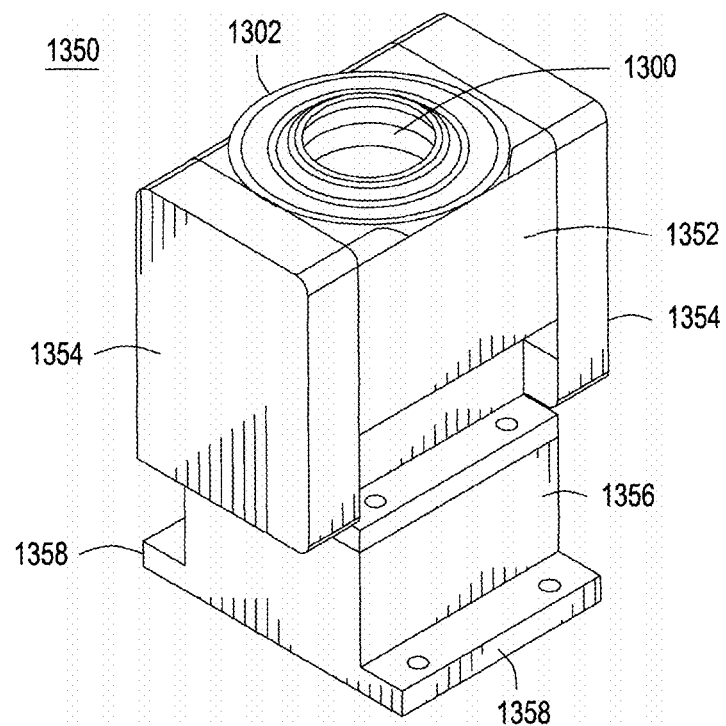
Figure 13C:
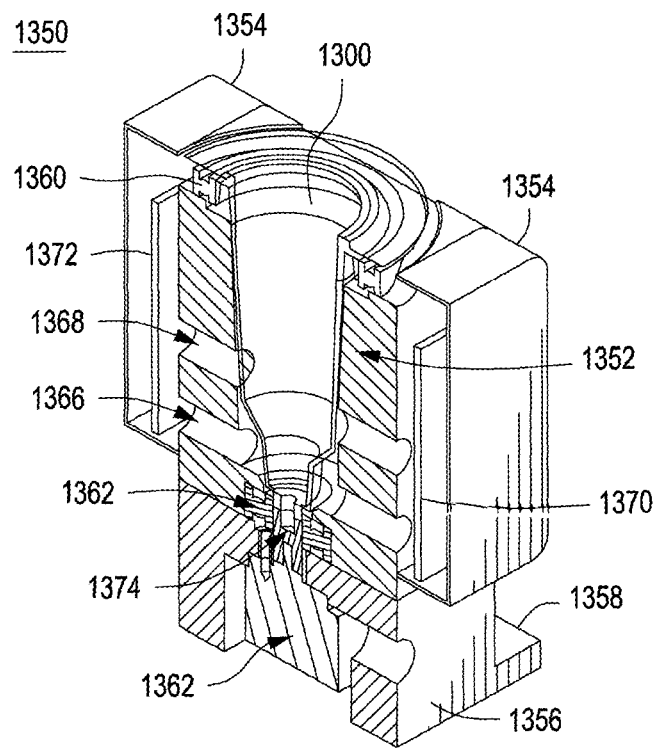

FIG. 13A shows one embodiment of a rotating growth vial 1300 for use with a cell growth device, such as cell growth device 1350 illustrated in FIGS. 13B-C. The rotating growth vial 1300, in some implementations, is a transparent container having an open end 1304 for receiving liquid media and cells, a central vial region 1306 that defines the primary container for growing cells, a tapered-to-narrowed region 1318 defining at least one light path 1308, 1310, a closed end 1316, and a drive engagement mechanism 1312. The rotating growth vial 1300 may have a central longitudinal axis 1320 around which the vial 1300 rotates, and the light paths 1308, 1310 may be generally perpendicular to the longitudinal axis of the vial. In some examples, first light path 1310 may be positioned in the lower narrowed portion of the tapered-to-narrowed region 1318. The drive engagement mechanism 1312, in some implementations, engages with a drive mechanism (e.g., actuator, motor (not shown)) to rotate the vial 1300. The actuator may include a drive shaft 1374 for a drive motor (not shown).

In some embodiments, the rotating growth vial 1300 includes a second light path 1308, for example, in the upper tapered region of the tapered-to-narrowed region 1318. In some examples, the walls defining the upper tapered region of the tapered-to-narrowed region 1318 for the second light path 1308 may be disposed at a wider angle relative to the longitudinal axis 1320 than the walls defining the lower narrowed portion of the tapered-to-narrowed region 1310 for the first light path 1310. Both light paths 1308, 1310, for example, may be positioned in a region of the rotating growth vial 1300 that is constantly filled with the cell culture (cells+growth media), and is not affected by the rotational speed of the growth vial 1300. As illustrated, the second light path 1308 is shorter than the first light path 1310 allowing for sensitive measurement of optical density (OD) values when the OD values of the cell culture in the vial are at a high level (e.g., later in the cell growth process), whereas the first light path 1310 allows for sensitive measurement of OD values when the OD values of the cell culture in the vial are at a lower level (e.g., earlier in the cell growth process).

Figure 14:
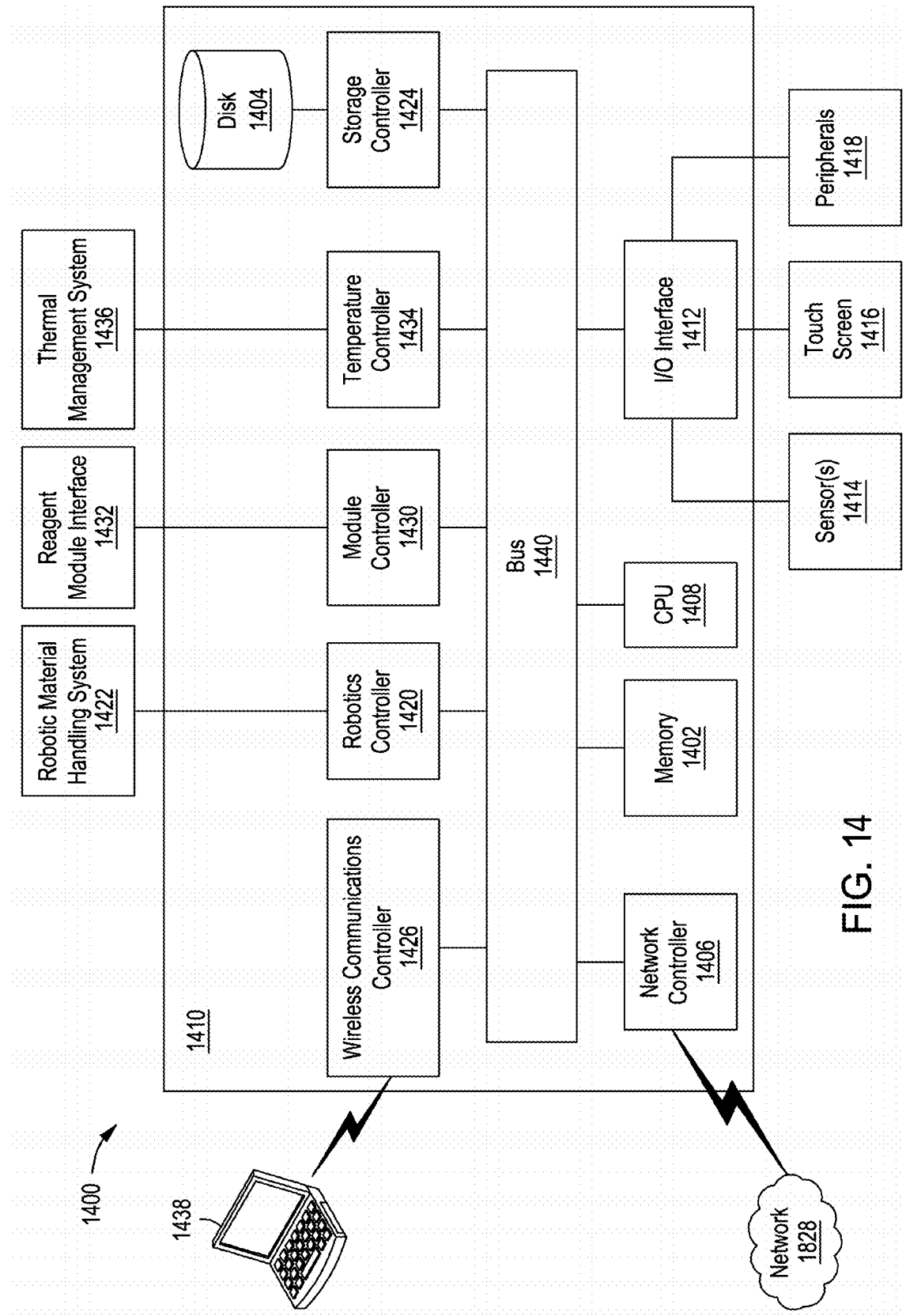
FIG. 14 is an example control system for use in an automated instrument.

The rotating growth vial 1300 may be reusable, or preferably, the rotating growth vial is consumable. In some embodiments, the rotating growth vial 1300 is consumable and can be presented to the user pre-filled with growth medium, where the vial 1300 is sealed at the open end 1304 with a foil seal. A medium-filled rotating growth vial packaged in such a manner may be part of a kit for use with a stand-alone cell growth device or with a cell growth module that is part of an automated instrument. To introduce cells into the vial, a user need only pipette up a desired volume of cells and use the pipette tip to punch through the foil seal of the vial 1300. Alternatively, of course, an automated instrument may transfer cells from, e.g., a reagent cartridge, to the growth vial. The growth medium may be provided in the growth vial or may also be transferred from a reagent cartridge to the growth vial before the addition of cells. Open end 1304 may include an extended lip 1302 to overlap and engage with the cell growth device 1350 (FIG. 13B). In automated instruments, the rotating growth vial 1300 may be tagged with a barcode or other identifying means that can be read by a scanner or camera that is part of the processing system 1410 as illustrated in FIG. 14.

In some implementations, the volume of the rotating growth vial 1300 and the volume of the cell culture (including growth medium) may vary greatly, but the volume of the rotating growth vial 1300 should be large enough for the cell culture in the growth vial 1300 to get proper aeration while the vial 1300 is rotating. In practice, the volume of the rotating growth vial 1300 may range from 1-250 ml, 2-100 ml, from 5-80 ml, 10-50 ml, or from 12-35 ml. Likewise, the volume of the cell culture (cells+growth media) should be appropriate to allow proper aeration in the rotating growth vial 1300. Thus, the volume of the cell culture should be approximately 10-85% of the volume of the growth vial 800, or 15-80% of the volume of the growth vial, or 20-70%, 30-60%, or 40-50% of the volume of the growth vial. In one example, for a 35 ml growth vial 1300, the volume of the cell culture would be from about 4 ml to about 27 ml.

The rotating growth vial 1300, in some embodiments, is fabricated from a bio-compatible transparent material- or at least the portion of the vial 1300 including the light path(s) is transparent. Additionally, material from which the rotating growth vial 1300 is fabricated should be able to be cooled to about 0° C. or lower and heated to about 75° C. or higher, such as about 2° C. or to about 70° C., about 4° C. or to about 60° C., or about 4° C. or to about 55° C. to accommodate both temperature-based cell assays and long-term storage at low temperatures. Further, the material that is used to fabricate the vial is preferably able to withstand temperatures up to 55° C. without deformation while spinning. Suitable materials include glass, polyvinyl chloride, polyethylene, polyamide, polyethylene, polypropylene, polycarbonate, poly(methyl methacrylate) (PMMA), polysulfone, polyurethane, and co-polymers of these and other polymers. Preferred materials include polypropylene, polycarbonate, or polystyrene. In some embodiments, the rotating growth vial 800 is inexpensively fabricated by, e.g., injection molding or extrusion.

FIGS. 13 B-C illustrate views of an example cell growth device 1350 that receives the rotating growth vial 1300. In some embodiments, the cell growth device 1350 rotates to heat or cool the cells or cell growth within the vial 1300 to a predetermined temperature range. In some implementations, the rotating growth vial 1300 can be positioned inside a main housing 1352 with the extended lip 1302 of the vial 1300 extending past an upper surface of the main housing 1352. In some aspects, the extended lip 1302 provides a grasping surface for a user inserting or withdrawing the vial 1300 from the main housing 1352 of the device 1350. Additionally, when fully inserted into the main housing 1352, a lower surface of the extended lip 1302 abuts an upper surface of the main housing 1352. In some examples, the main housing 1352 of the cell growth device 1350 is sized such that outer surfaces of the rotating growth vial 1300 abut inner surfaces of the main housing 1352 thereby securing the vial 1300 within the main housing 1352. In some implementations, the cell growth device 1350 can include end housings 1354 disposed on each side of the main housing 1354 and a lower housing 1356 disposed at a lower end of the main housing 1352. In some examples, the lower housing 1356 may include flanges 1358 that can be used to attach the cell growth device 1350 to a temperature control (e.g., heating/cooling) mechanism or other structure such as a chassis of an automated cell processing system.

As shown in FIG. 13C, the cell growth device 1350, in some implementations, can include an upper bearing 1360 and lower bearing 1362 positioned in main housing 1352 that support the vertical load of a rotating growth vial 1300 that has been inserted into the main housing 1352. In some examples, the cell growth device 1350 may also include a primary optical port 1366 and a secondary optical port 1368 that are aligned with the first light path 1310 and second light path 1308 of the vial 1300 when inserted into the main housing 1352. In some examples, the primary and secondary optical ports 1366, 1368 are gaps, openings, or portions of the main housing constructed from transparent materials that allow light to pass through the vial 1300 to perform cell growth OD measurements. In addition to the optical ports 1366, 1368, the cell growth device 1350 may include an emission board 1370 that provides one or more illumination sources for the light path(s), and detector board 1372 to detect the light after the light travels through the cell culture liquid in the rotating growth vial 1300. In one example, the illumination sources disposed on the emission board 1370 may include light emission diodes (LEDs) or photodiodes that provide illumination at one or more target wavelengths commensurate with the growth media typically used in cell culture (whether, e.g., mammalian cells, bacterial cells, animal cells, yeast cells).

In some implementations, the emission board 1370 and/or detector board 1372 are communicatively coupled through a wired or wireless connection to a processing system (e.g., processing system 126, 1720, 1810) that controls the wavelength of light output by the emission board 1370 and receives and processes the illumination sensed at the detector board 1372. The remotely controllable emission board 1370 and detector board 1372, in some aspects, provide for conducting automated OD measurements during the course of cell growth. For example, the processing system 126, 1720 may control the periodicity with which OD measurements are performed, which may be at predetermined intervals or in response to a user request Further, the processing system 126, 1720 can use the sensor data received from the detector board 1372 to perform real-time OD measurements and adjust cell growth conditions (e.g., temperature, speed/direction of rotation).

In some embodiments, the lower housing 1356 may contain a drive motor (not shown) that generates rotational motion that causes the rotating growth vial 1300 to spin within the cell growth device 1350. In some implementations, the drive motor may include a drive shaft 1374 that engages a lower end of the rotating growth vial 1300. The drive motor that generates rotational motion for the rotating growth vial 1300, in some embodiments, is a brushless DC type drive motor with built-in drive controls that can be configured to maintain a constant revolution per minute (RPM) between 0 and about 3000 RPM. Alternatively, other motor types such as a stepper, servo, or brushed DC motors can be used. Optionally, the drive motor may also have direction control to allow reversing of the rotational direction, and a tachometer to sense and report actual RPM. In other examples, the drive motor can generate oscillating motion by reversing the direction of rotation at a predetermined frequency. In one example, the vial 1300 is rotated in each direction for one second at a speed of 350 RPM. The drive motor, in some implementations, is communicatively coupled through a wired or wireless communication network to a processing system (e.g., processing system 126, 1720) that is configured to control the operation of the drive motor, which can include executing protocols programmed into the processor and/or provided by user input, for example as described in relation to module controller 1430 of FIG. 14. For example, and the drive motor can be configured to vary the speed and/or rotational direction of the vial 1300 to cause axial precession of the cell culture thereby enhancing mixing in order to prevent cell aggregation and increase aeration. In some examples, the speed or direction of rotation of the drive motor may be varied based on optical density sensor data received from the detector board 1372.

In some embodiments, main housing 1352, end housings 1354 and lower housing 1356 of the cell growth device 1350 may be fabricated from a robust material including aluminum, stainless steel, and other thermally conductive materials, including plastics. These structures or portions thereof can be created through various techniques, e.g., metal fabrication, injection molding, creation of structural layers that are fused, etc. While in some examples the rotating growth vial 1300 is reusable, in other embodiments, the vial 1300 is preferably is consumable. The other components of the cell growth device 1350, in some aspects, are preferably reusable and can function as a stand-alone benchtop device or as a module in an automated instrument.

In some implementations, the processing system that is communicatively coupled to the cell growth module may be programmed with information to be used as a "blank" or control for the growing cell culture. A "blank" or control, in some examples, is a vessel containing cell growth medium only, which yields 100% transmittance and 0 OD, while the cell samples deflect light rays and will have a lower percentage transmittance and higher OD. As the cells grow in the media and become denser, transmittance decreases and OD increases. The processor of the cell growth module, in some implementations, may be programmed to use wavelength values for blanks commensurate with the growth media typically used in cell culture (whether, e.g., mammalian cells, bacterial cells, animal cells, yeast cells). Alternatively, a second spectrophotometer and vessel may be included in the cell growth module, where the second spectrophotometer is used to read a blank at designated intervals.

Cell Enrichment Module

To reduce background of cells that have not received a nucleic acid of interest, the instrument may comprise a cell enrichment module may also allow a selection process to increase the overall number of transformed cells in a cell populations created using the transformation/transfection systems of the invention. In certain aspects, the cell enrichment module may be integrated with the cell growth module.

In some embodiments, enriching the sample includes one or more of increasing the overall percentage of cells of interest in the sample and depleting cells not of interest in the sample.

For example, the introduced nucleic acid can include a gene, which confers antibiotic resistance or another selectable marker. Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, and chloramphenicol-resistance gene. In some embodiments, removing dead cell background is aided using lytic enhancers such as detergents, osmotic stress, temperature, enzymes, proteases, bacteriophage, reducing agents, or chaotropes. In other embodiments, cell removal and/or media exchange is used to reduce dead cell background.

Cell Wash and/or Concentration Module

The cell wash and/or concentration module can utilize any method for exchanging the liquids in the cell environment, and may concentrate the cells or allow them to remain in essentially the same or greater volume of liquid as used in the nucleic acid assembly module. Further, in some aspects, the processes performed in the cell wash module also render the cells electrocompetent, by, e.g., use of glycerol in the wash.

Numerous different methods can be used to wash the cells, including density gradient purification, dialysis, ion exchange columns, filtration, centrifugation, dilution, and the use of beads for purification.

In some aspects, the cell wash and/or concentration module utilizes a centrifugation device. In other aspects, the cell wash and/or concentration module utilizes a filtration module. In yet other aspects, beads are coupled to moieties that bind to the cell surface. These moieties include but are not limited to antibodies, lectins, wheat germ agglutinin, mutated lysozymes, and ligands.

In other aspects, the cells are engineered to be magnetized, allowing magnets to pellet the cells after wash steps. The mechanism of cell magnetization can include but is not limited to ferritin protein expression.

Figure 12A:
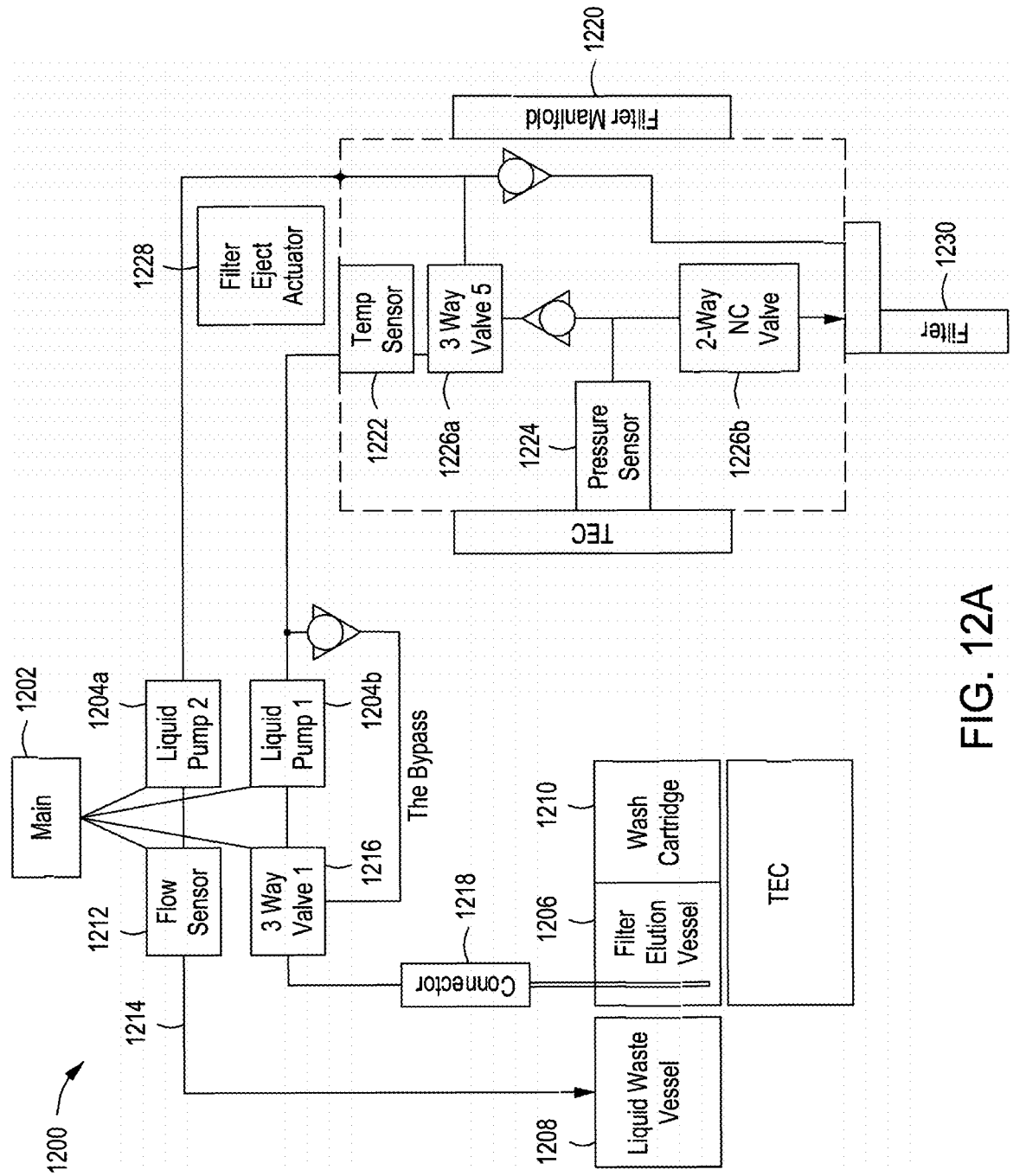
FIGS. 12A-12C provide a functional block diagram and two perspective views of an example filtration module for use in an automated instrument.

The cell wash and/or concentration module, in some implementations, is a filtration module. Turning to FIG. 12A, a block diagram illustrates example functional units of a filtration module 1200. In some implementations, a main control 1202 of the filtration module 1200 includes a first liquid pump 1204 b to intake wash fluid 1206 and a second liquid pump 1204b to remove liquid waste to a liquid waste module 1208 (e.g., such as the liquid waste module 1728 of FIGS. 17A and 17B). A flow sensor 1212 may be disposed on a connector 1214 to the liquid waste module 1208 to monitor release of liquid waste from the filtration module. A valve 1216 (a three-way valve as illustrated) may be disposed on a connector 1218 to the wash fluid in wash cartridge 1210 to selectively connect the wash fluid and the filtration module 1200.

The filtration module 1200, in some implementations, includes a filter manifold 1220 for filtering and concentrating a cell sample. The filter manifold 1220 may include one or more temperature sensor(s) 1222 and pressure sensor (s) 1224 to monitor flow and temperature of the wash fluid and/or liquid waste. The sensors 1222, 1224, in some embodiments, are monitored and analyzed by a processing system of the automated multi-mode cell processing system, such as the processing system 1410 of FIG. 14. The filter manifold 1220 may include one or more valves 1226b for directing flow of the wash fluid and/or liquid waste. The processing system of the automated multi-mode cell processing instrument, for example, may actuate the valves according to a set of instructions for directing filtration by the filtration module 1200.

The filtration module 1200 includes at least one filter 1230. Examples of filters suitable for use in the filtration module 1200 include membrane filters, ceramic filters and metal filters. The filter may be used in any shape; the filter may for example be cylindrical or essentially flat. The filter selected for a given operation or a given workflow, in some embodiments, depends upon the type of workflow (e.g., bacterial, yeast, viral, etc.) or the volumes of materials being processed. For example, while flat filters are relatively low cost and commonly used, filters with a greater surface area, such as cylindrical filters, may accept higher flow rates. In another example, hollow filters may demonstrate lower recovery rates when processing small volumes of sample (e.g., less than about 10 ml). For example, for use with bacteria, it may be preferable that the filter used is a membrane filter, particularly a hollow fiber filter. With the term "hollow fiber" is meant a tubular membrane. The internal diameter of the tube, in some examples, is at least 0.1 mm, more preferably at least 0.5 mm, most preferably at least 0.75 mm and preferably the internal diameter of the tube is at most 10 mm, more preferably at most 6 mm, most preferably at most 1 mm. Filter modules having hollow fibers are commercially available from various companies, including G.E. Life Sciences (Marlborough, Mass.) and InnovaPrep (Drexel, Mo.) (see, e.g., US20110061474A1 to Page et al., entitled "Liquid to Liquid Biological Particle Concentrator with Disposable Fluid Path").

In some implementations, the filtration module 1200 includes a filter ejection means 1228 (e.g., actuator) to eject a filter 1230 post use. For example, a user or the robotic handling system may push the filter 1230 into position for use such that the filter is retained by the filter manifold 1220 during filtration. After filtration to remove the used filter 1230, the filter ejection actuator 1228 may eject the filter 1230, releasing the filter 1230 such that the user or the robotic handling system may remove the used filter 1230 from the filtration module 1200. The used filter 1230, in some examples, may be disposed within the solid waste module 1718 of FIGS. 17A and 17B, or returned to a filter cartridge 1240, as illustrated in FIG. 12D.

Figure 12D:
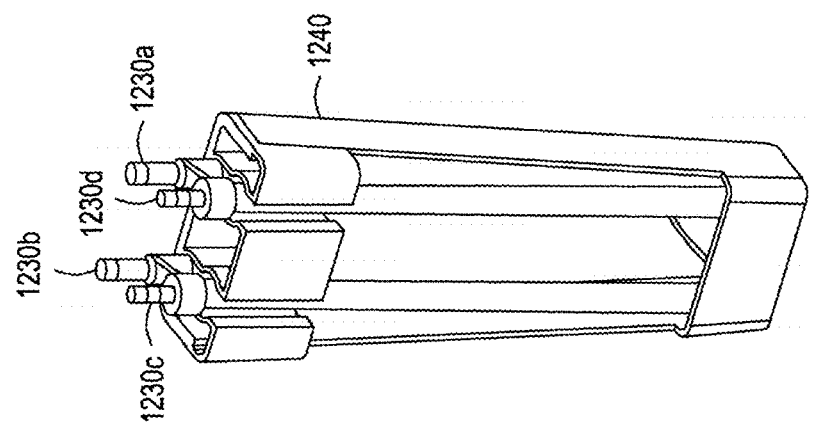
FIG. 12D is a perspective view of an example filter cartridge for use in an automated instrument.

Turning to FIG. 12D, in some implementations, filters 1230a, b, c, d provided in the filter cartridge 1240 disposed within the chassis of the automated instrument are transported to the filtration module 1200 by a robotic handling system (e.g., the robotic handling system 1708 of FIGS. 17A and 17B) and positioned within the filtration module 1200 prior to use.

The filtration module 1200, in some implementations, requires periodic cleaning. For example, the processing system may alert a user when cleaning is required through the user interface of the automated instrument and/or through a wireless messaging means (e.g., text message, email, and/or personal computing device application). A decontamination filter, for example, may be loaded into the filtration module 1200 and the filtration module 1200 may be cleaned with a wash solution and/or alcohol mixture.

Figure 11A:
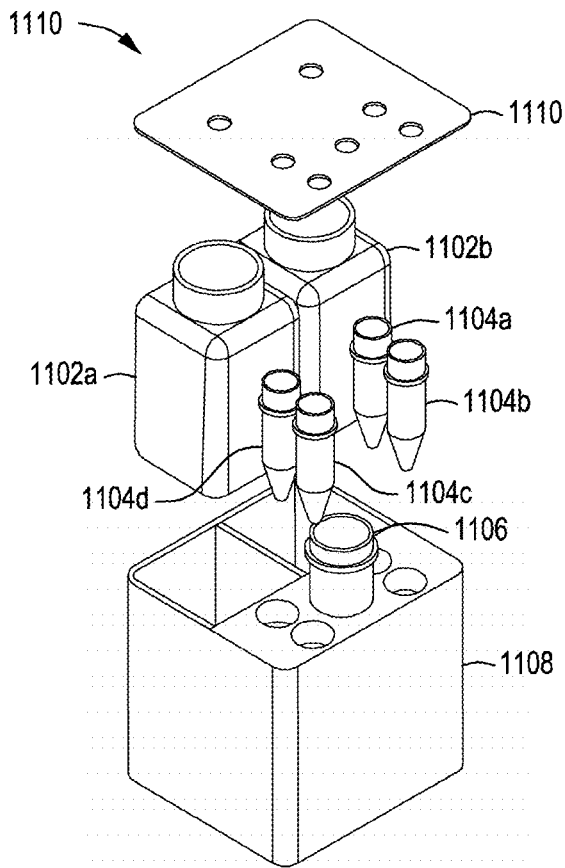
FIGS. 11A-11B depict an exploded view and a top view, respectively, of an example wash cartridge for use in an automated instrument.

In some implementations, the filtration module 1200 is in fluid connection with a wash cartridge 1210 (such as the wash cartridge 1100 of FIG. 11A) containing the wash fluid via the connector 1218. For example, upon positioning by the user of the wash cartridge 1210 within the chassis of the automated instrument, the connector 1218 may mate with a bottom inlet of the wash cartridge 1210, creating a liquid passage between the wash fluid 1206 and the filtration module 1200.

Figure 12C:
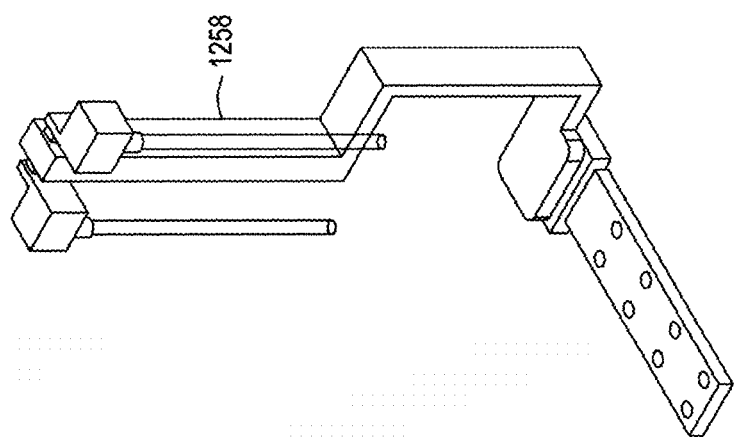
Figure 12B:
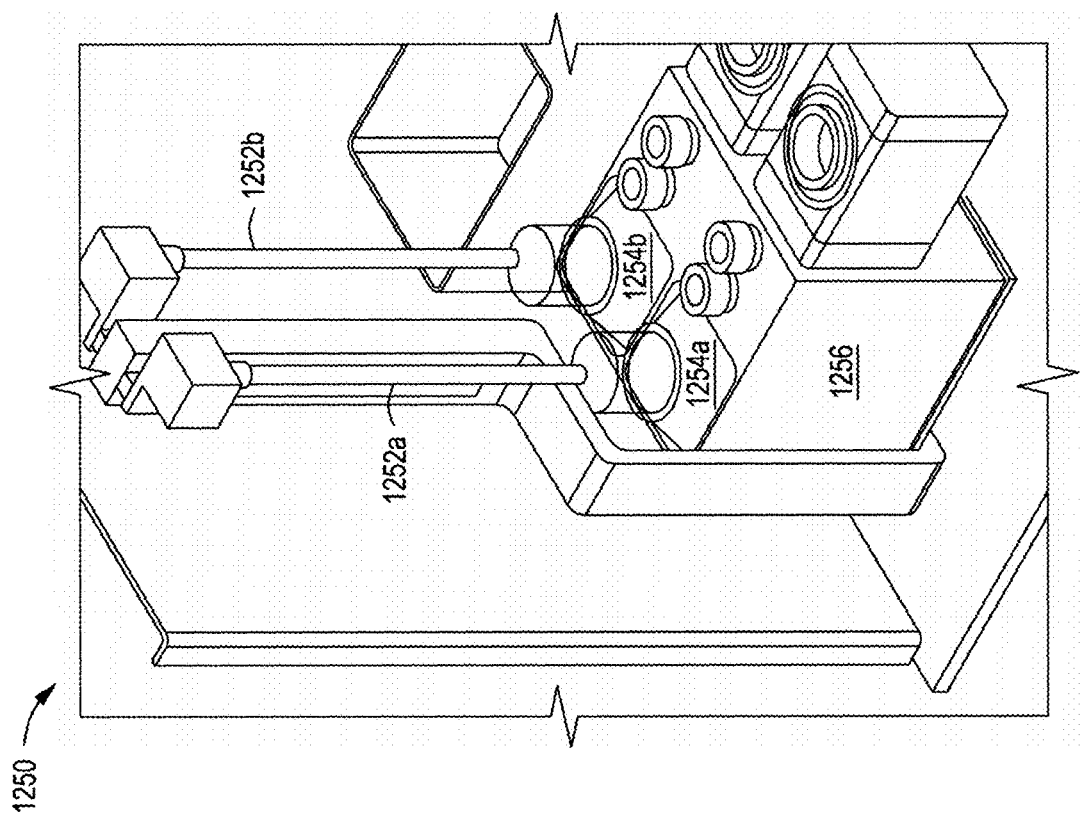

Turning to FIGS. 12B and 12C, in some implementations, a dual filter filtration module 1250 includes dual filters 1252a and 1252b disposed over dual wash reservoirs 1254a and 1254b. In an example, each filter may be a hollow core fiber filter having 0.45 um pores and greater than 85 cm2 area. The wash reservoirs 1254a and 1254b, in some examples, may be 50 mL, 100 mL, or over 200 mL in volume. In some embodiments, the wash reservoirs 1254a and 1254*b* are disposed in a wash cartridge 1256, such as the wash or reagent cartridge 1100 of FIG. 11A.

The processing system of the automated instrument, in some implementations, controls actuation of the dual filters 1252*a* and 1252*b* in an X (horizontal) and Z (vertical) direction to position the filters 1252*a*, 1252*b* in the wash reservoirs 1254*a* and 1254*b*. In a particular example, the dual filters 1252*a* and 1252*b* may be move in concert along the X axis but have independent Z axis range of motion.

As illustrated, the dual filters 1252*a* and 1252*b* of the filtration module 1250 are connected to a slender arm body 1258. In some embodiments, any pumps and valves of the filtration module 1250 may be disposed remotely from the body 1258 (e.g., within a floor of the chassis of the automated instrument). In this manner, the filtration module 1250 may replace much bulkier conventional commercial filtration modules.

Figure 17A:
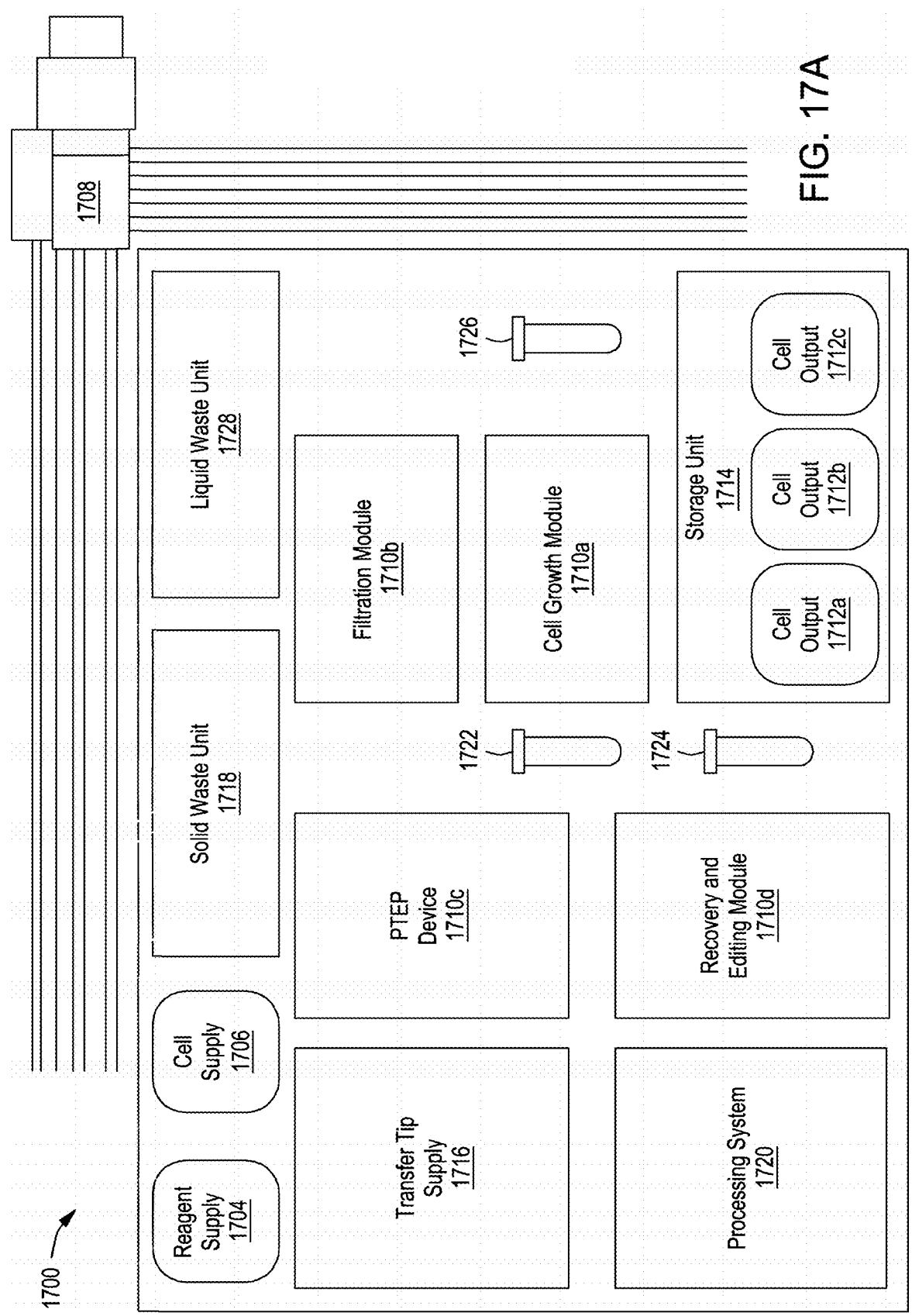
FIG. 17A is a functional block system diagram of another example embodiment of an automated instrument for the automated transformation of multiple cells.
Figure 17B:
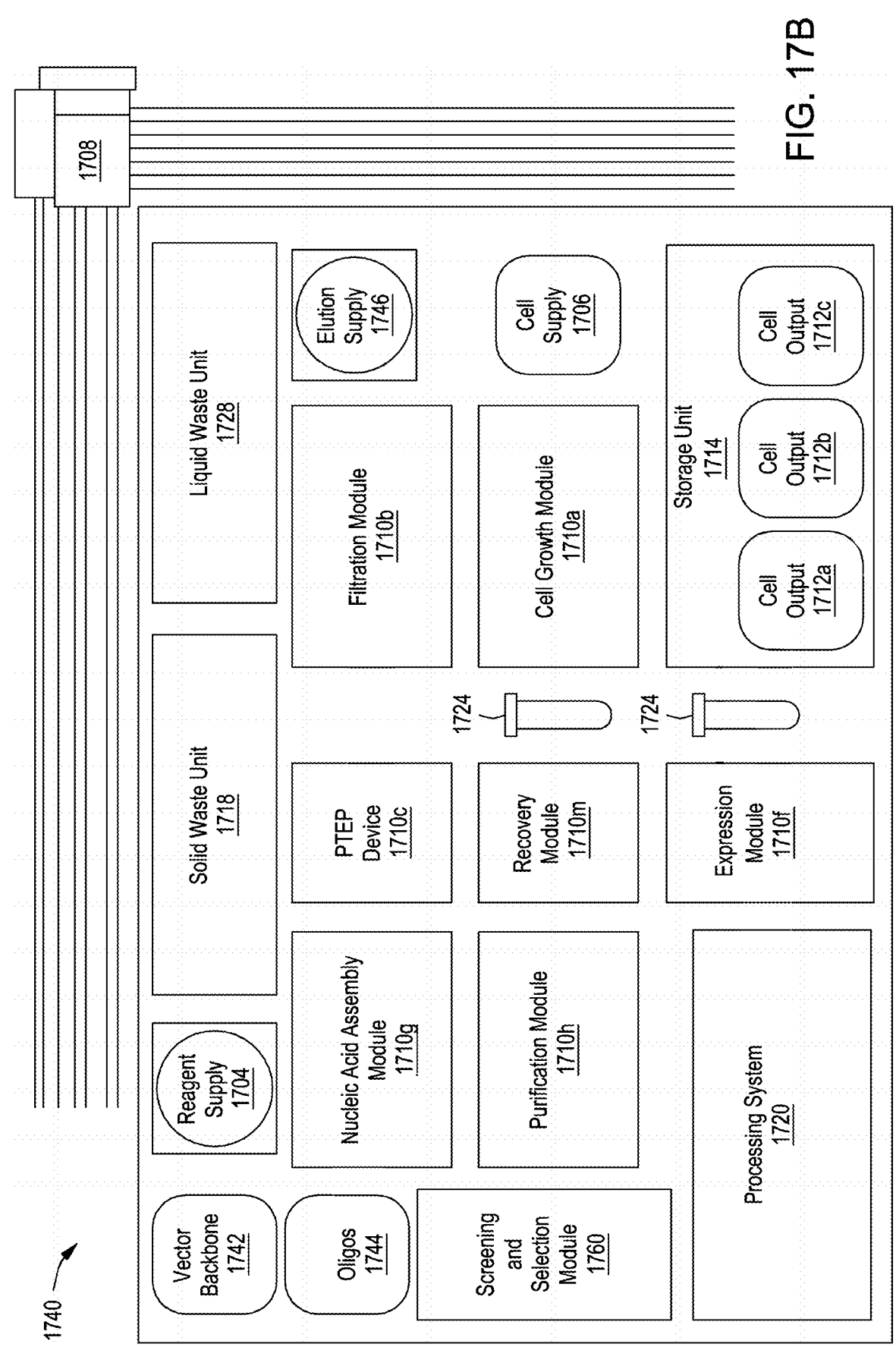
FIG. 17B is a functional block system diagram of yet another example embodiment of an automated instrument for the transformation of multiple cells.
Figure 18A:
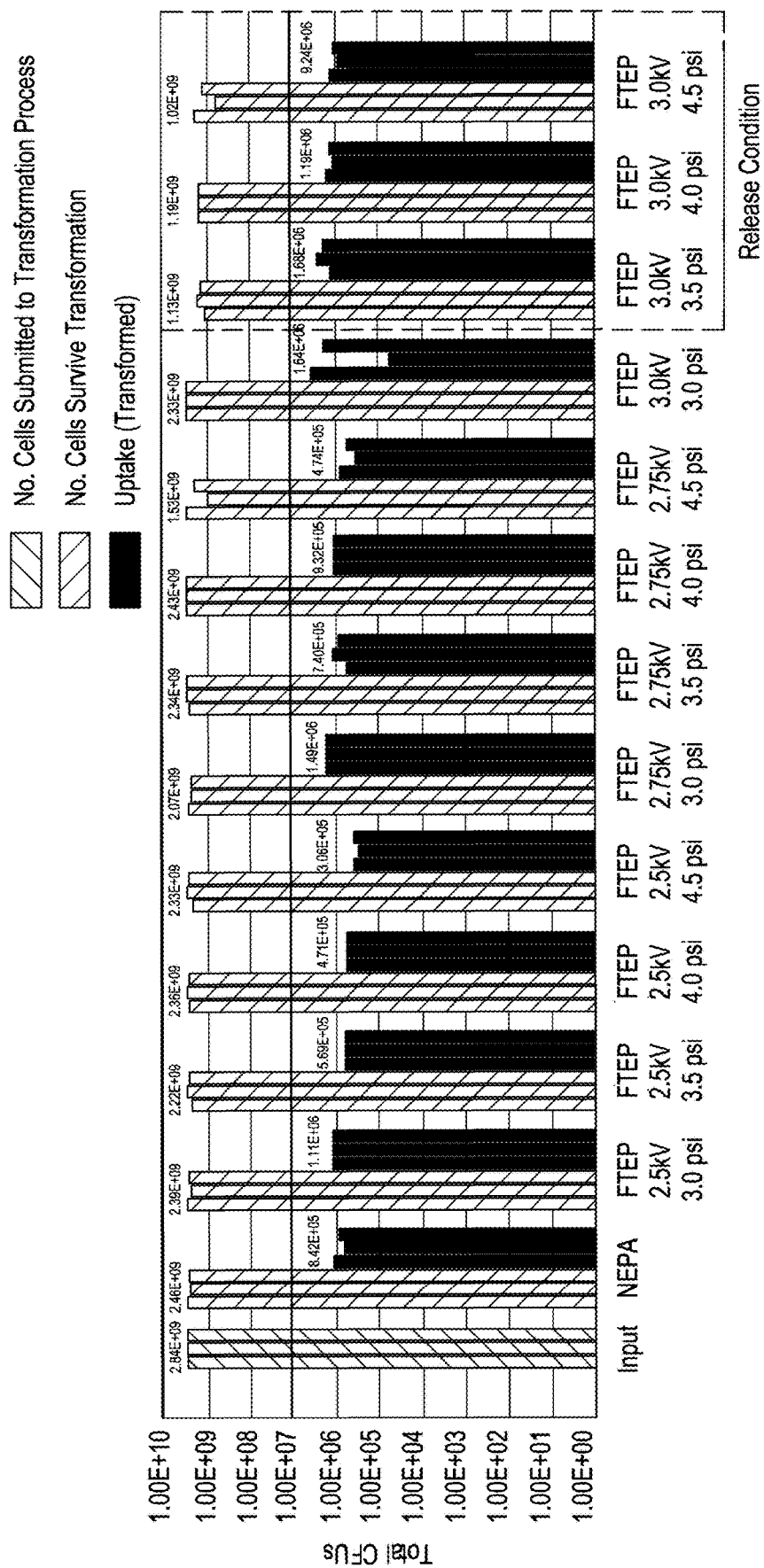
FIG. 18A is a bar graph showing the results of electroporation of *E. coli* using a device of the disclosure and a comparator electroporation device.
Figure 18B:
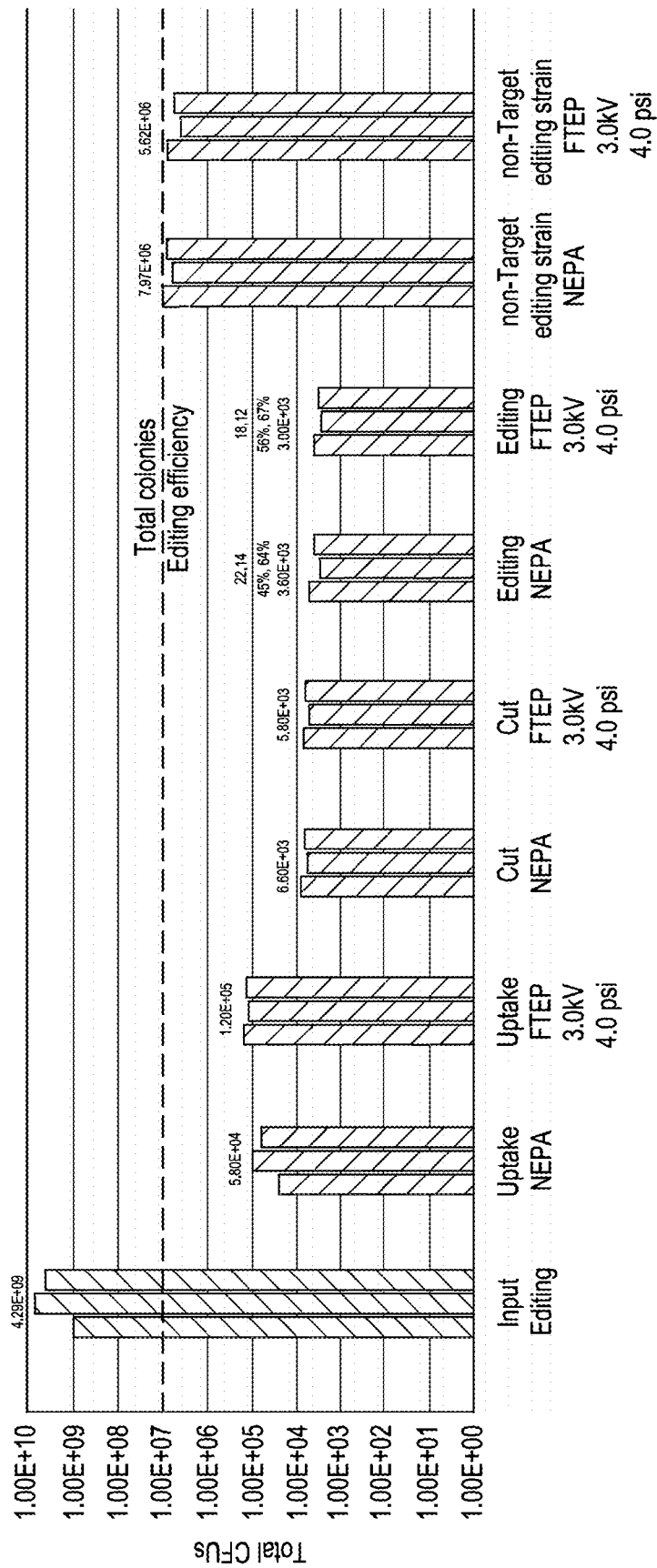
FIG. 18B is a bar graph showing uptake, cutting, and editing efficiencies of *E. coli* cells transformed via an FTEP as described herein benchmarked against a comparator electroporation device.

Further, in some embodiments, the filtration module 1250 is in liquid communication with a waste purge system designed to release liquid waste into a liquid waste storage unit, such as the liquid waste vessel 1208 of FIG. 12A or the liquid waste storage module 1728 of FIGS. 17A and 17B.

Wash and Reagent Cartridges

In some embodiments, the automated multi-module cell processing instrument comprises one or more wash or reagent cartridges such as those illustrated in FIGS. 11A-11E. The cartridge 1100 includes a pair of containers 1102 *a, b*, a set of four small tubes 1104 *a, b, c, d*, and a larger tube 1106 held in a cartridge body 1108. One or more of the containers 1102 *a, b*, and tubes 1104 *a, b, c, d* and 1106, in some embodiments, is sealed with a pierceable foil for access by an automated liquid handling system, such as a sipper or pipettor. In other embodiments, one or more of the containers 1102*a, b*, and tubes 1104*a, b, c, d*, and 1106 includes a sealable access gasket. The top of one or more of the containers 1102*a, b*, and tubes 1104*a, b, c, d*, and 1106, in some embodiments, is marked with machine-readable indicia (not illustrated) for automated identification of the contents.

In some embodiments, containers 1102*a, b* contain wash solutions. The wash solution may be a same or different wash solutions. In some examples, wash solutions may contain, e.g., buffer, buffer and 10% glycerol, 80% ethanol.

Figure 11B:
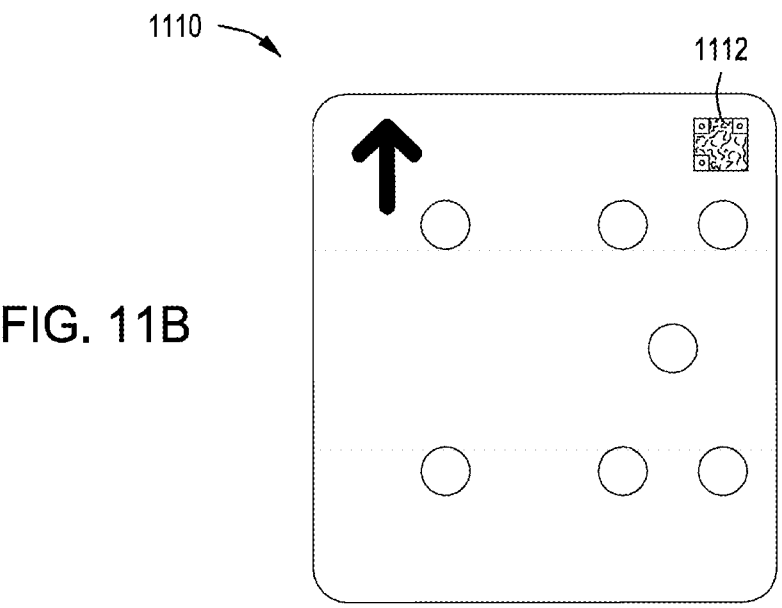

In some implementations, a cover 1110 secures the containers 1102*a, b* and tubes 1104*a, b, c, d* and 1106 within the cartridge body 1108. Turning to FIG. 11B, the cover 1120 may include apertures for access to each of the containers 1102*a, b* and tubes 1104*a, b, c, d* and 1106. Further, the cover 1120 may include machine-readable indicia 1112 for identifying the type of cartridge (e.g., accessing a map of the cartridge contents). Alternatively, apertures may be marked separately with the individual contents.

Figure 11C:
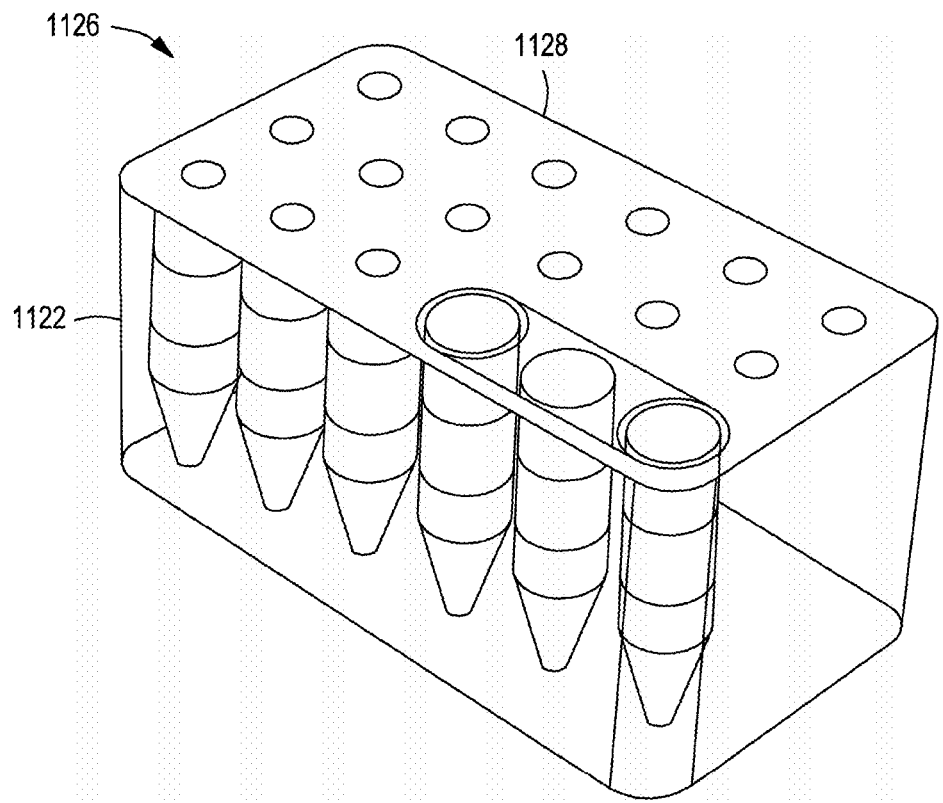
FIGS. 11C-11E depict an example reagent cartridge for use in an automated instrument.

In some embodiments, the reagent cartridge is a reagent cartridge such as that illustrated in FIG. 11C. FIG. 11C shows a reagent cartridge 1126 having a body 1122 including a set of eighteen tubes or vials 1128; however, the embodiment shown in FIG. 11C does not include an FTEP device. Looking at FIG. 11E, reagent cartridge includes sixteen tubes or vials 1126*a-p* and an FTEP device 1124, held in a cartridge body 1122. One or more of the tubes or vials 1128 (FIG. 11C) or 1126*a-p* (FIG. 11E), in some embodiments, is sealed with pierceable foil for access by an automated liquid handling system, such as a sipper or pipettor. In other embodiments such as that shown in FIG. 11E, one or more of the tubes or vials 1126*a*-1126*p* includes a sealable access gasket. The top of each of the small tubes or vials 1126*a*-1126*p*, in some embodiments, is marked with machine-readable indicia (not illustrated) for automated identification of the contents. The machine-readable indicia may include a bar code, QR code, or other machine-readable coding. Other automated means for identifying a particular container can include color coding, symbol recognition (e.g., text, image, icon, etc.), and/or shape recognition (e.g., a relative shape of the container). Rather than being marked upon the vessel itself, in some embodiments, an upper surface of the cartridge body and/or the cartridge cover may contain machine-readable indicia for identifying contents. The small tubes or vials may each be of a same size. Alternatively, multiple volumes of tubes or vials may be provided in the reagent cartridge 1100. In an illustrative example, each tube or vial may be designed to hold between 2 and 20 mL, between 4 and 10 mL, or about 5 mL. In some embodiments where only small volumes of some reagents are required, tube inserts may be used to accommodate small (e.g., microfuge) tubes in a larger receptacle.

In an illustrative example, the tubes or vials 1126*a*-1126*p* may each hold one the following materials: a vector backbone, oligonucleotides, reagents for nucleic acid assembly, a user-supplied cell sample, an inducer agent, magnetic beads in buffer, ethanol, an antibiotic for cell selection, reagents for eluting cells and nucleic acids, an oil overlay, other reagents, and cell growth and/or recovery media.

Figure 11D:
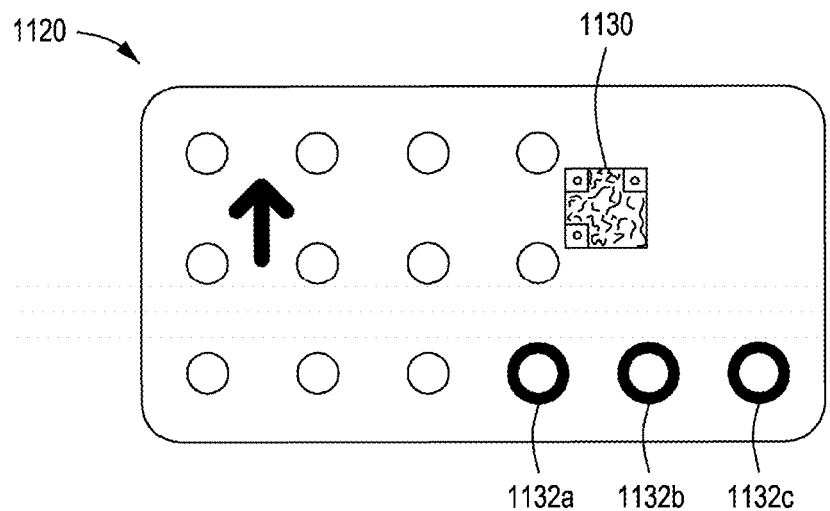

In some implementations, a cover 1120 as seen in FIG. 11D secures the tubes or vials 1128 within the cartridge body 1122 of FIG. 11C. Turning to FIG. 11D, the cover 1120 may include apertures for access to each of the small tubes or vials 1126. Three large apertures 1132*a-c* are outlined in a bold band to indicate positions to add user-supplied materials. The user-supplied materials, for example, may include a vector backbone, oligonucleotides, and a cell sample. Further, the cover 1120 may include machine-readable indicia 1130 for identifying the type of cartridge (e.g., accessing a map of the cartridge contents). Alternatively, each aperture may be marked separately with the individual contents. In some implementations, to ensure positioning of user-supplied materials, the vials or tubes provided for filling in the lab environment may have unique shapes or sizes such that the cell sample vial or tube only fits in the cell sample aperture, the oligonucleotides vial or tube only fits in the oligonucleotides aperture, and so on.

FTEP Modules

The FTEP (transformation) module may implement any cell transformation or transfection techniques routinely performed by electroporation. Electroporation is a widely-used method for permeabilization of cell membranes that works by temporarily generating pores in the cell membranes with electrical stimulation. The applications of electroporation include the delivery of DNA, RNA, siRNA, peptides, proteins, antibodies, drugs or other substances to a variety of cells such as mammalian cells (including human cells), plant cells, archea, yeasts, other eukaryotic cells, bacteria, and other cell types. Electrical stimulation may also be used for cell fusion in the production of hybridomas or other fused cells. During a typical electroporation procedure, cells are suspended in a buffer or medium that is favorable for cell survival. For bacterial cell electroporation, low conductance mediums, such as water, glycerol solutions and the like, are often used to reduce the heat production by transient high current. The cells and material to be electroporated into the cells (collectively "the cell sample") is then placed in a cuvette embedded with two flat electrodes for an electrical discharge. For example, Bio-Rad (Hercules, Calif.) makes the Gene Pulser Xcell™ line of products to electroporate cells in cuvettes. Traditionally, electroporation requires high field strength.

Generally speaking, microfluidic electroporation—using cell suspension volumes of less than approximately 20 ml and as low as 1 μl—allows more precise control over a transfection or transformation process and permits flexible integration with other cell processing tools compared to bench-scale electroporation devices. Microfluidic electroporation thus provides unique advantages for, e.g., single cell transformation, processing and analysis; multi-unit FTEP device configurations; and integrated, automated multi-module cell processing.

The present disclosure provides electroporation devices, modules, and methods that achieve high efficiency cell electroporation with low toxicity where the electroporation devices and systems can be integrated with other automated cell processing tools. Further, the electroporation device of the disclosure allows for multiplexing where two to many electroporation units are constructed and used in parallel, and allows for particularly easy integration with robotic liquid handling instrumentation. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

Although the disclosure is focused primarily on the above-described FTEP modules for use in the instrument, a person of ordinary skill in the art would understand upon reading the present disclosure that other electroporation and/or microfluidic devices could be used in the invention in an equivalent fashion to that described herein. Specific electroporation and microfluidic methods that can be used in the devices of the disclosure include, but are not limited to, those described in U.S. App. No. 62/566,374; U.S. App. No. 62/566,375; U.S. App. No. 62/551,069; U.S. App. No. 2017/0218355; WO 2017/040995; U.S. App. No. 20150368604; U.S. App. No. 20070218355; U.S. App. No. 20110009807; U.S. Pat. Nos. 9,063,136; 9,029,109; 8,058,056; 7,951,582; 7,771,984; 7,186,559; 6,492,175; Zhu T et al., Biomed Microdevices 12:35-40 (2010), T. Geng et al. Journal of Controlled Release 144: 91-100 (2010)h; Zhan, Y et al., (2011). Birck and NCN Publications. Paper 979; Adamo A et al., Anal Chem. February 5; 85(3): 1637-1641 (2013); del Rosal et al., Lab Chip. October 7, 13(19): 3803-3821 (2013); Genga T and Lu C, Lab Chip, 13, 3803-3821 (2013), Li, Y. et al., Sci. Rep. 5, 17817 (2015), Zhao, D. et al., Sci. Rep. 6, 18469 (2016), Garcia P. A. et al., Lab Chip, 17, 490 (2017).

During the electroporation process, it is important to use voltage sufficient for achieving electroporation of material into the cells, but not too much voltage as too much voltage will decrease cell viability. For example, to electroporate a suspension of a human cell line, 200 volts is needed for a 0.2 ml sample in a 4 mm-gap cuvette with exponential discharge from a capacitor of about 1000 g. However, if the same 0.2 ml cell suspension is placed in a longer container with 2 cm electrode distance (5 times of cuvette gap distance), the voltage required would be 1000 volts, but a capacitor of only 40 μF (1/25 of 1000 g) is needed because the electric energy from a capacitor follows the equation of:

$$E=0.5U^2C$$

where E is electric energy, U is voltage and C is capacitance. Therefore a high voltage pulse generator is actually easy to manufacture because it needs a much smaller capacitor to store a similar amount of energy. Similarly, it would not be difficult to generate other wave forms of higher voltages.

The electroporation devices of the disclosure can allow for a high rate of cell transformation in a relatively short amount of time. The rate of cell transformation is dependent on the cell type and the number of cells being transformed. For example, for $E.\ coli$, the electroporation devices can provide a cell transformation rate of $10^3$ to $10^{12}$ cells per second, $10^4$ to $10^{10}$ per second, $10^5$ to $10^9$ per second, or $10^6$ to $10^8$ per second. Typically, $10^8$ yeast cells may be transformed per minute, and $10^{10}$-$10^{12}$ bacterial cells may be transformed per minute. The electroporation devices also allow transformation of batches of cells ranging from 1 cell to $10^{12}$ cells in a single transformation procedure using parallel devices.

Figure 4A:
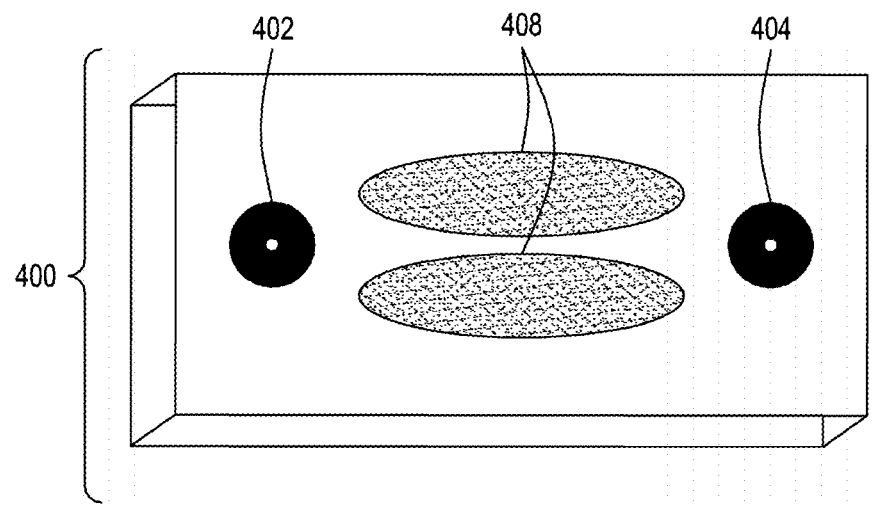
FIG. 4A is an illustration of a top view of one embodiment of the FTEP devices of the disclosure.
Figure 4B:
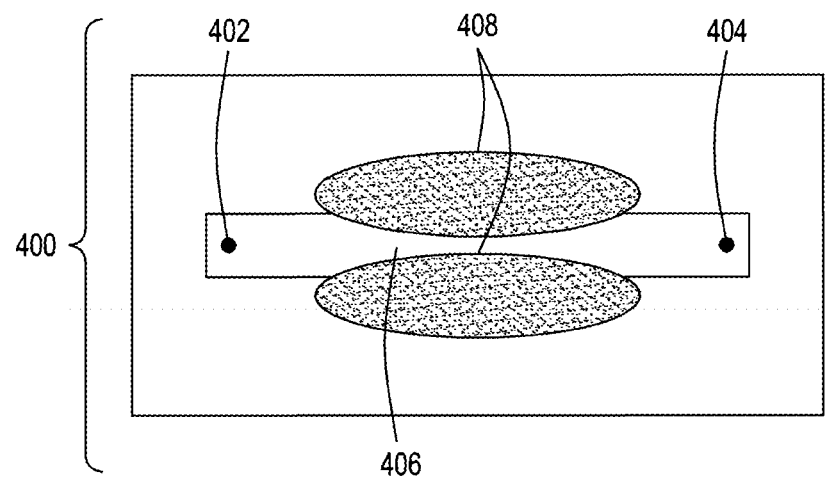
FIG. 4B is an illustration of the top view of a cross section of the embodiment of the device shown in FIG. 4A.
Figure 4C:
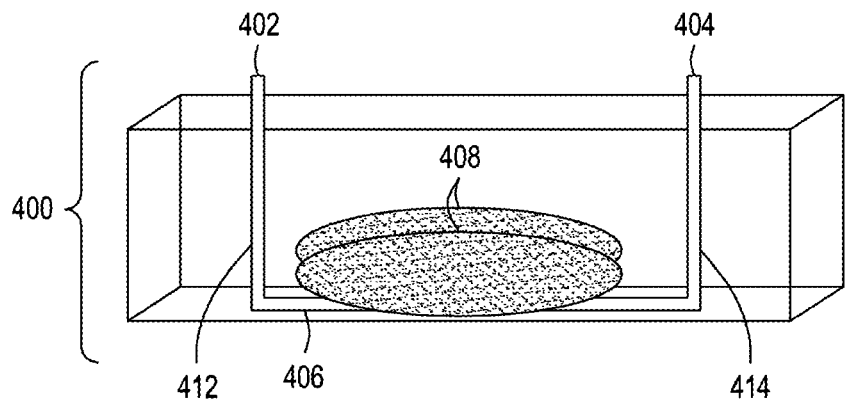
FIG. 4C is an illustration of a side view of a cross section of the embodiment of the device shown in FIGS. 4A and 4B.

One embodiment of the FTEP device described herein is illustrated in FIGS. 4A-4C. FIG. 4A shows a planar top view of an FTEP device 400 having an inlet 402 for introducing a fluid containing cells and nucleic acid to be delivered to the cells into the FTEP device 400 and an outlet 404 for removing the transformed cells following electroporation. Oval electrodes 408 are positioned so as to define a center portion of the flow channel (not shown) where the channel narrows based on the curvature of the electrodes. FIG. 4B shows a cutaway view from the top of the device 400, with the inlet 402, outlet 404, and electrodes 408 positioned with respect to a flow channel 406. Note that the electrodes 408 define a narrowing of flow channel 406. FIG. 4C shows a side cutaway view of the device 400 with the inlet 402 and inlet channel 412, and outlet 404 and outlet channel 414. The electrodes 408 are oval in shape and positioned so that they define a narrowed portion of the flow channel 406.

In the FTEP devices of the disclosure, the toxicity level of the transformation results in greater than 30% viable cells after electroporation, preferably greater than 35%, 40%, 45%, 50%, 55%, 60%, 70%, 75%, 80%, 85%, 90%, 95% or even 99% viable cells following transformation, depending on the cell type and the nucleic acids being introduced into the cells.

The housing of the FTEP device can be made from many materials depending on whether the FTEP device is to be reused, autoclaved, or is disposable, including stainless steel, silicon, glass, resin, polyvinyl chloride, polyethylene, polyamide, polystyrene, polyethylene, polypropylene, acrylonitrile butadiene, polycarbonate, polyetheretheketone (PEEK), polysulfone and polyurethane, co-polymers of these and other polymers. Similarly, the walls of the channels in the device can be made of any suitable material including silicone, resin, glass, glass fiber, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Preferred materials include crystal styrene, cyclo-olefin polymer (COP) and cyclic olephin co-polymers (COC), which allow the device to be formed entirely by injection molding in one piece with the exception of the electrodes and, e.g., a bottom sealing film if present.

The FTEP devices described herein (or portions of the FTEP devices) can be created or fabricated via various techniques, e.g., as entire devices or by creation of structural layers that are fused or otherwise coupled. For example, for metal FTEP devices, fabrication may include precision mechanical machining or laser machining; for silicon FTEP devices, fabrication may include dry or wet etching; for glass FTEP devices, fabrication may include dry or wet etching, powderblasting, sandblasting, or photostructuring; and for plastic FTEP devices fabrication may include thermoforming, injection molding, hot embossing, or laser machining. The components of the FTEP devices may be manufactured separately and then assembled, or certain components of the FTEP devices (or even the entire FTEP device except for the electrodes) may be manufactured (e.g., using 3D printing) or molded (e.g., using injection molding) as a single entity, with other components added after molding. For example, housing and channels may be manufactured or molded as a single entity, with the electrodes (and, e.g., bottom sealing film) later added to form the FTEP module (see, FIG. 10F (i)). Alternatively, the FTEP device may also be formed in two or more parallel layers, e.g., a layer with the horizontal channel and filter, a layer with the vertical channels, and a layer with the inlet and outlet ports, which are manufactured and/or molded individually and assembled following manufacture. (See, e.g., FIG. 9A.)

In specific aspects, the FTEP device can be manufactured using a circuit board as a base, with the electrodes, filter and/or the flow channel formed in the desired configuration on the circuit board, and the remaining housing of the device containing, e.g., the one or more inlet and outlet channels and/or the flow channel formed as a separate layer that is then sealed onto the circuit board. The sealing of the top of the housing onto the circuit board provides the desired configuration of the different elements of the FTEP devices of the disclosure. Also, two to many FTEP devices may be manufactured on a single substrate, then separated from one another thereafter or used in parallel. In certain embodiments, the FTEP devices are reusable and, in some embodiments, the FTEP devices are disposable. In additional embodiments, the FTEP devices may be autoclavable.

The electrodes 408 can be formed from any suitable metal, such as copper, stainless steel, titanium, aluminum, brass, silver, rhodium, gold or platinum, or graphite. One preferred electrode material is alloy 303 (UNS330300) austenitic stainless steel. An applied electric field can destroy electrodes made from of metals like aluminum. If a multiple-use (i.e., non-disposable) flow-through FTEP device is desired—as opposed to a disposable, one-use flow-through FTEP device—the electrode plates can be coated with metals resistant to electrochemical corrosion. Conductive coatings like noble metals, e.g., gold, can be used to protect the electrode plates.

Additionally, the FTEP devices may comprise push-pull pneumatic means to allow multi-pass electroporation procedures; that is, cells to electroporated may be "pulled" from the inlet toward the outlet for one pass of electroporation, then be "pushed" from the outlet end of the flow-through FTEP device toward the inlet end to pass between the electrodes again for another pass of electroporation. This process may be repeated one to many times.

Depending on the type of cells to be electroporated (e.g., bacterial, yeast, mammalian) and the configuration of the electrodes, the distance between the electrodes in the flow channel can vary widely. For example, in the embodiments shown in FIGS. 4A-4I, 5A-5H, 6, and 7A-7E where the electrodes form a portion of the wall of the flow channel where the flow channel decreases in width, the distance between the electrodes in the flow channel may be between 10 μm and 5 mm, or between 25 μm and 3 mm, or between 50 μm and 2 mm, or between 75 μm and 1 mm. In other embodiments such as those depicted in FIGS. 8A-8U, 9A-9C, and 10A-10D where the electrodes are positioned on either end of the channel narrowing, the distance between the electrodes in the flow channel may be between 1 mm and 10 mm, or between 2 mm and 8 mm, or between 3 mm and 7 mm, or between 4 mm and 6 mm. The overall size of the FTEP device may be from 3 cm to 15 cm in length, or 4 cm to 12 cm in length, or 4.5 cm to 10 cm in length. The overall width of the FTEP device may be from 0.5 cm to 5 cm, or from 0.75 cm to 3 cm, or from 1 cm to 2.5 cm, or from 1 cm to 1.5 cm.

The region of the flow channel that is narrowed is typically wide enough so that at least two cells can fit in the narrowed portion side-by-side. For example, a typical bacterial cell is 1 μm in diameter; thus, the narrowed portion of the flow channel of the FTEP device used to transform such bacterial cells will be at least 2 μm wide. In another example, if a mammalian cell is approximately 50 μm in diameter, the narrowed portion of the flow channel of the FTEP device used to transform such mammalian cells will be at least 100 μm wide. That is, the narrowed portion of the FTEP device will not physically contort or "squeeze" the cells being transformed.

In embodiments of the FTEP device where reservoirs are used to introduce cells and nucleic acid into the FTEP device, the reservoirs range in volume from 100 μL to 10 mL, or from 500 μL to 75 mL, or from 1 mL to 5 mL. The flow rate in the FTEP ranges from 0.1 mL to 5 mL per minute, or from 0.5 mL to 3 mL per minute, or from 1.0 mL to 2.5 mL per minute. The pressure in the FTEP device ranges from 1-30 psi, or from 2-10 psi, or from 3-5 psi.

To avoid different field intensities between the electrodes, the electrodes should be arranged in parallel. Furthermore, the surface of the electrodes should be as smooth as possible without pin holes or peaks. Electrodes having a roughness Rz of 1 to 10 μm are preferred. In another embodiment of the invention, the flow-through electroporation device comprises at least one additional electrode which applies a ground potential to the FTEP device.

The electrodes are configured to deliver 1-25 Kv/cm, or 5-20 Kv/cm, or 10-20 Kv/cm. The further apart the electrodes are, the more voltage needs to be supplied; in addition, the voltage delivered of course depends on the types of cells being porated, the medium in which the cells are suspended, the size of the electroporation channel, and the length and diameter of the electrodes. There are many different pulse forms that may be employed with the FTEP device, including exponential decay waves, square or rectangular waves, arbitrary wave forms, or a selected combination of wave forms. One type of common pulse form is the exponential decay wave, typically made by discharging a loaded capacitor to the cell sample. The exponential decay wave can be made less steep by linking an inductor to the cell sample so that the initial peak current can be attenuated. When multiple waveforms in a specified sequence are used, they can be in the same direction (direct current) or different directions (alternating current). Using alternating current can be beneficial in that two topical surfaces of a cell instead of just one can be used for molecular transport, and alternating current can prevent electrolysis. The pulse generator can be controlled by a digital or analog panel. In some embodiments, square wave forms are preferred, and in other embodiments, an initial wave spike before the square wave is preferred.

The FTEP device may be configured to electroporate cell sample volumes between 1 μl to 5 ml, 10 μl to 2 ml, 25 μl to 1 ml, or 50 μl to 750 μl. The medium or buffer used to suspend the cells and material (reagent) to be electroporated into the cells for the electroporation process may be any suitable medium or buffer, such as MEM, DMEM, IMDM, RPMI, Hanks', PBS and Ringer's solution, where the media may be provided in a reagent cartridge as part of a kit. Further, because the cells must be made electrocompetent prior to transformation or transfection, the buffer also may comprise glycerol or sorbitol, and may also comprise a surfactant. For electroporation of most eukaryotic cells the medium or buffer usually contains salts to maintain a proper osmotic pressure. The salts in the medium or buffer also render the medium conductive. For electroporation of very small prokaryotic cells such as bacteria, sometimes water or 10% glycerol is used as a low conductance medium to allow a very high electric field strength. In that case, the charged molecules to be delivered still render water-based medium more conductive than the lipid-based cell membranes and the medium may still be roughly considered as conductive particularly in comparison to cell membranes.

The compound to be electroporated into the cells can be any compound known in the art to be useful for electroporation, such as nucleic acids, oligonucleotides, polynucleotides, DNA, RNA, peptides, proteins and small molecules like hormones, cytokines, chemokines, drugs, or drug precursors.

Figure 4D:
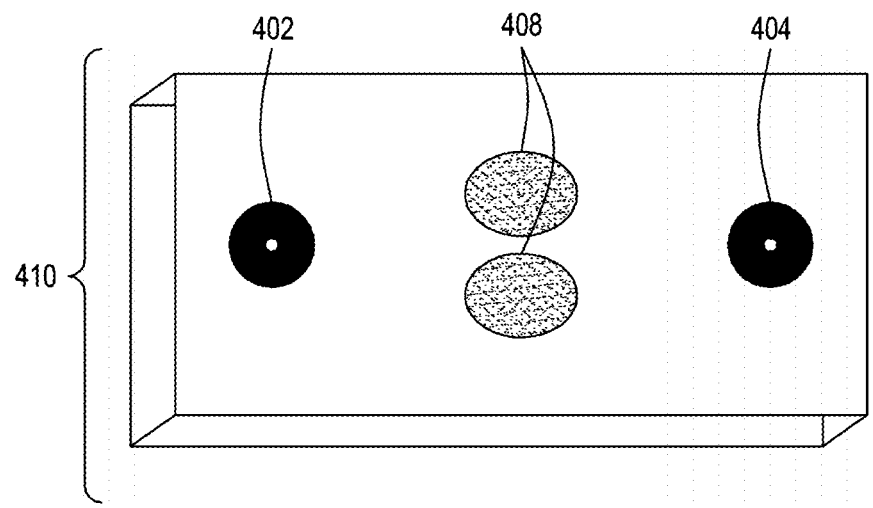
FIG. 4D is an illustration of a top view of another embodiment of the FTEP devices of the disclosure.
Figure 4E:
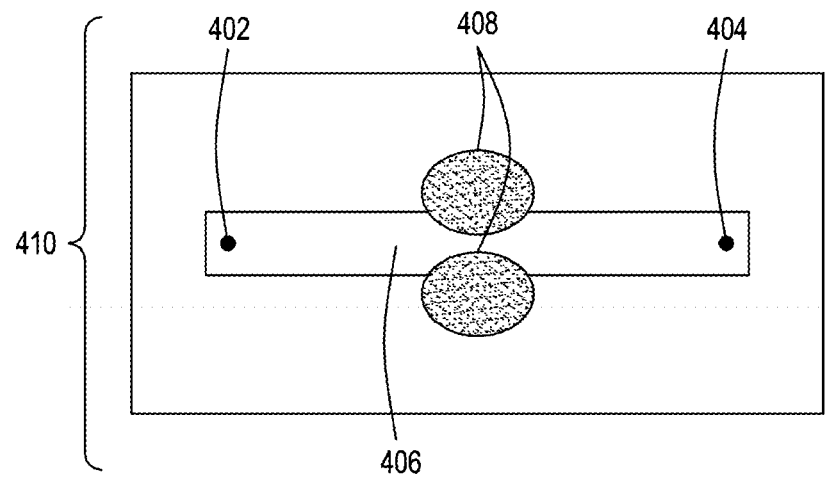
FIG. 4E is an illustration of the top view of a cross section of the embodiment of the device shown in FIG. 4D.
Figure 4F:
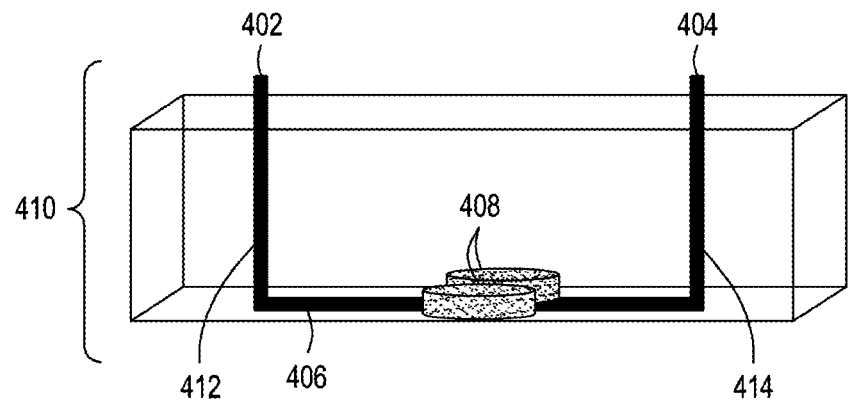
FIG. 4F is an illustration of a side view of a cross section of the embodiment of the device shown in FIGS. 4D and 4E.

Another embodiment of the FTEP devices described herein is illustrated in FIGS. 4D-4F. FIG. 4D shows a top planar view of an FTEP device 410 having an inlet 402 for introducing a fluid containing cells and nucleic acid into the FTEP device 410 and an outlet 404 for removing the transformed cells following electroporation. Cylindrical electrodes 408 are positioned so as to define a center portion of the flow channel (not shown) where the flow channel narrows as a result of the curvature of the electrodes. FIG. 4E shows a cutaway view from the top of the FTEP device 410, with the inlet 402, outlet 404, and electrodes 408 positioned with respect to a flow channel 406. Again, note that the electrodes 408 define a narrowed portion or region of flow channel 406. FIG. 4F shows a side cutaway view of FTEP device 410 with the inlet 402 and inlet channel 412, and outlet 404 and outlet channel 414. The electrodes 408 are cylindrical and positioned in the flow channel 406 defining a narrowed portion of the flow channel 406.

Yet another embodiment of the FTEP devices of the disclosure is illustrated in FIGS. 4G-4I. FIG. 4G shows a top planar view of an FTEP device 420 having an inlet 402 for introducing a fluid containing cells and nucleic acid into FTEP device 420, and an outlet 404 for removing the transformed cells following electroporation. The semi-cylindrical electrodes 408 are positioned so as to define a narrowed portion of a flow channel (not shown) where the channel narrows from both ends based on the curvature of the electrodes. FIG. 4H shows a cutaway view from the top of FTEP device 420, with the inlet 402, outlet 404, and electrodes 408 positioned with respect to a flow channel 406. FIG. 4I shows a side cutaway view of FTEP device 420 with inlet 402 and inlet channel 412, and outlet 404 and outlet channel 414. The semi-cylindrical electrodes 408 are positioned in the flow channel 406 so that they define a narrowed portion of the flow channel 406. It should be noted that the devices depicted in FIGS. 4A-4I show the electrodes positioned substantially mid-way along the flow channel; however, in other aspects of the devices, the electrodes may be positioned in narrowed regions of the flow channel more toward the inlet of the FTEP device or more toward the outlet of the FTEP device.

Figure 5A:
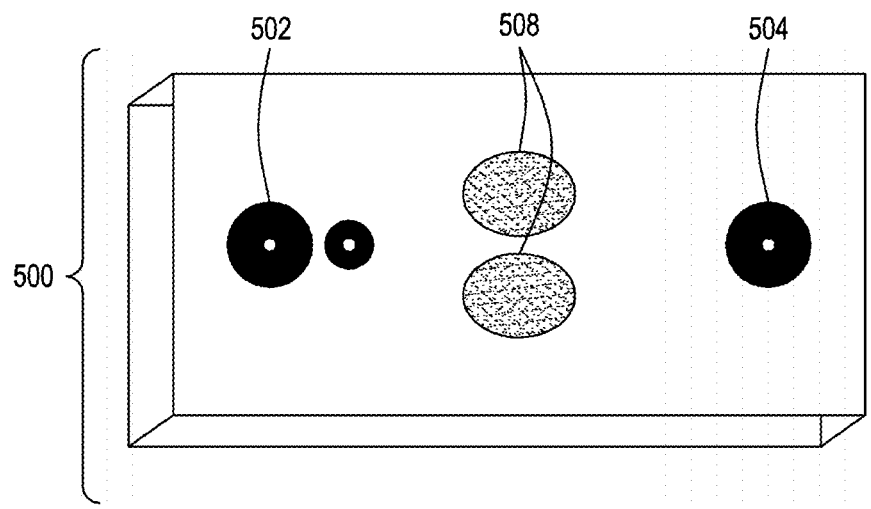
FIG. 5A is an illustration of the top view of a cross section of a further embodiment of the FTEP devices described herein with separate inlets for the cells and the nucleic acids.
Figure 5B:
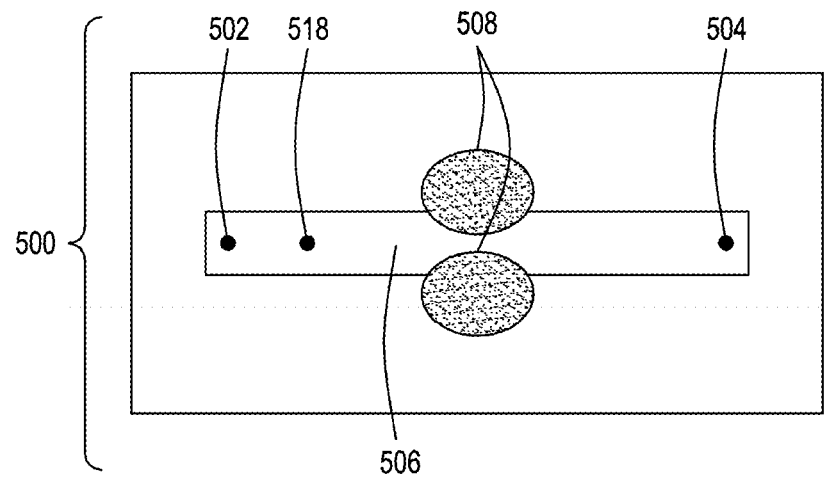
FIG. 5B is an illustration of the top view of a cross section of the embodiment of the device shown in FIG. 5A.

FIGS. 5A-5E show embodiments of the FTEP devices of the disclosure with separate inlets for the cells and the nucleic acid. FIG. 5A shows a top planar view of an FTEP device 500 having a first inlet 502 for introducing a fluid containing cells into FTEP device 500; a second inlet 518 for introducing a fluid containing nucleic acids to be electroporated into the cells into FTEP device 500; electrodes 508; and an outlet 504 for removing the transformed cells following electroporation. Although these embodiments are illustrated with cylindrical electrodes, as shown in FIG. 5A, other shaped electrodes with a curved edge—e.g., oval, semi-cylindrical, and the like as shown in relation to FIGS. 4A-4I—may be used to define the flow channel. FIG. 5B shows a cutaway view from the top of FTEP device 500, with the first inlet 502, second inlet 518, outlet 504, and electrodes 508 positioned with respect to the flow channel 506.

Figure 5C:
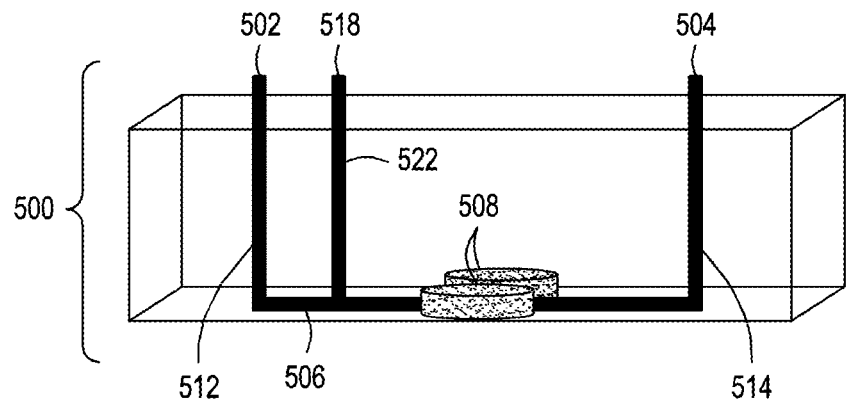
FIG. 5C is an illustration of a side view of a cross section of the embodiment of the device shown in FIG. 5B.
Figure 5D:
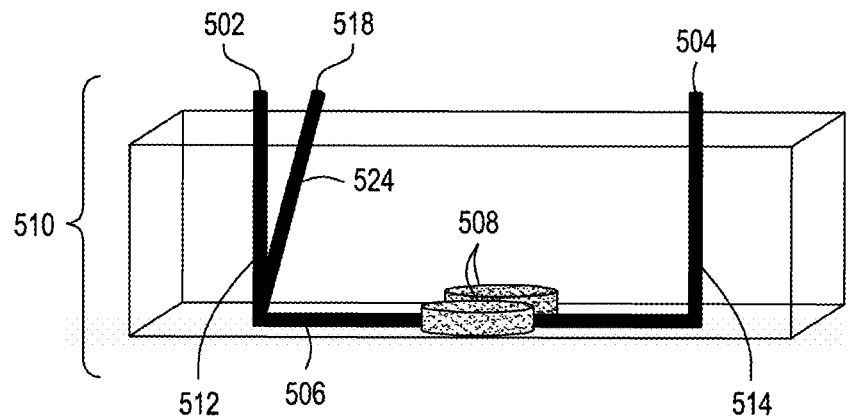
FIG. 5D is an illustration of a side view of a cross section of a variation on the embodiment of the device shown in FIGS. 5A and 5B.
Figure 5E:
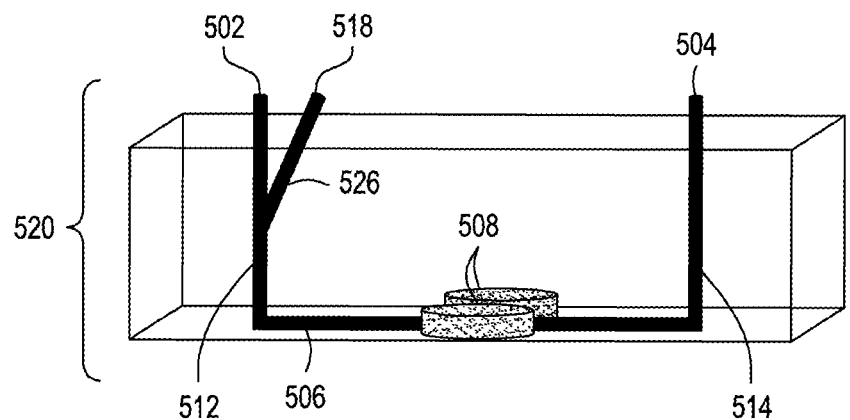
FIG. 5E is an illustration of a side view of a cross section of another variation on the embodiment of the device shown in FIGS. 5C and 5D.

FIG. 5C shows a cutaway view of the embodiment of FTEP device 500 with the first inlet 502 and second inlet 518 positioned as shown in FIGS. 5A and 5B. In FIG. 5C, the first inlet channel 512 and second inlet channel 522 meet independently with flow channel 506, and the liquid (cells and material to be porated or delivered to the cells) flows through the flow channel 506 to the outlet channel 514 and outlet 504 where the transformed cells are removed from the FTEP device. The electrodes 508 are positioned in the flow channel 506 so that they define a narrowed portion of the flow channel 506. FIG. 5D shows a side cutaway view of a variation 510 on the embodiment of the FTEP device 500 depicted in FIGS. 5A and 5B. Here, the first inlet channel 512 and second inlet channel 524 intersect with the flow channel 506 at a three-way junction, and the liquid (cells and material to be porated or delivered to the cells) flows through the flow channel 506 to the outlet channel 514 and outlet 504 where the transformed cells are removed from the FTEP device. The electrodes 508 are positioned in the flow channel 506 defining a narrowed portion of the flow channel 506. FIG. 5E shows a first side cutaway view 520 of a yet another variation of the FTEP device 500 shown in FIGS. 5A and 5B. Here, the first inlet channel 512 and second inlet channel 526 intersect at a junction where the cells and nucleic acids mix prior to introduction of the combined fluids to the flow channel 506. The fluids flow through the flow channel 506 to the outlet channel 514 and outlet 504 where the transformed cells are removed from the FTEP device. Electrodes 508 are positioned in the flow channel 506 so that they define a narrowed portion of the flow channel 506.

Figure 5F:
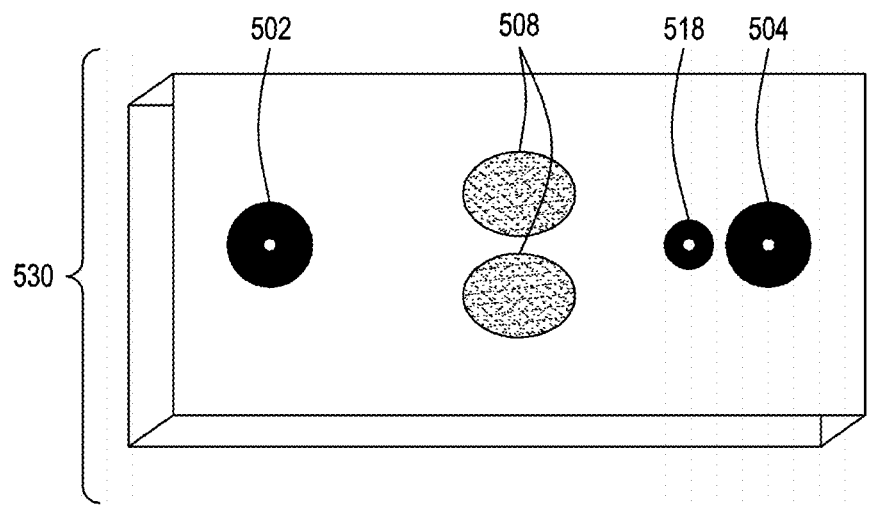
FIG. 5F is an illustration of the top view of a cross section of yet another embodiment of the FTEP devices of the disclosure where the FTEP comprises two separate inlets for the cells and the nucleic acids.
Figure 5G:
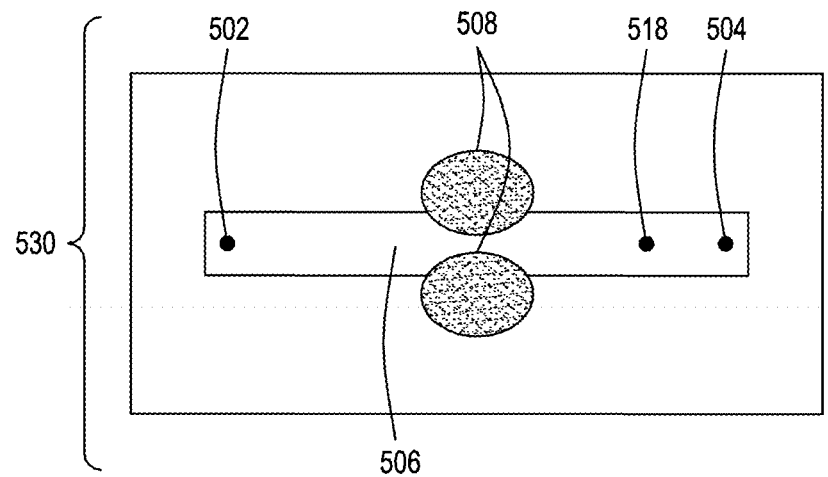
FIG. 5G is an illustration of a top view of a cross section of the embodiment of the device shown in FIG. 5F.
Figure 5H:
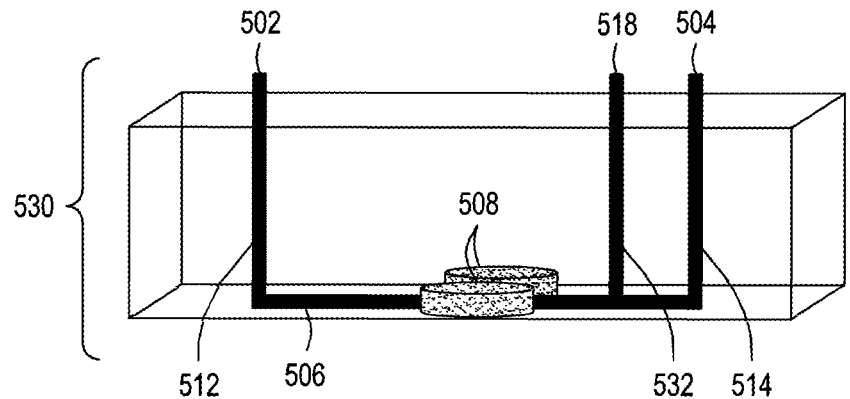
FIG. 5H is an illustration of a side view of a cross section of the embodiment of the device shown in FIGS. 5F and 5G.

FIGS. 5F-5H show another embodiment of the FTEP devices of the disclosure with separate inlets for the cells and the nucleic acid. FIG. 5F shows a top planar view of an electroporation device 530 having a first inlet 502 for introducing a fluid containing cells, a second outlet 518 for introducing nucleic acids to be electroporated into the cells, and an outlet 504 for removing the transformed cells following electroporation. The electrodes 508 are positioned between the first inlet 502 where the cells are introduced into the FTEP device and the second inlet 518 where the nucleic acids are introduced into the FTEP device. FIG. 5G shows a cutaway view from the top of the FTEP device 530, with the first inlet 502, second inlet 518, and outlet 504, and with electrodes 508 positioned between the first inlet channel 502 and the second inlet channel 518, where the electrodes 508 form a narrowed portion of flow channel 506. FIG. 5H shows a side cutaway view of FTEP device 530 with the first inlet 502 where the cells are introduced into the FTEP device and first inlet channel 512, the second inlet 518 where the nucleic acids are introduced into the FTEP device and second inlet channel 532, and an outlet channel 514 and outlet 504 where the transformed cells are removed from the FTEP device. The electrodes 508 are positioned in the flow channel 506 defining a narrow portion of the flow channel 506 and are positioned between the first inlet channel 512 and the second inlet channel 532 such that the material to be introduced into the cells is added to the fluid comprising the cells after the cells have been electroporated.

Figure 6:
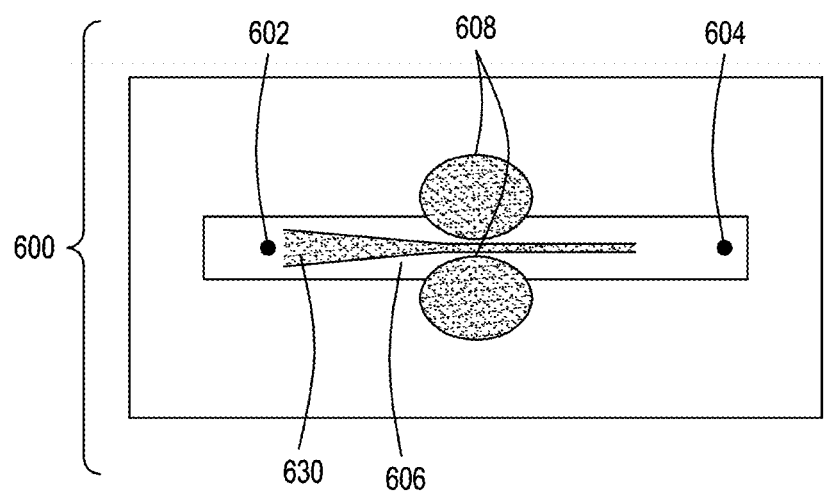
FIG. 6 is an illustration of a top view of a cross section of yet an additional embodiment of the FTEP devices of the disclosure, here including flow focusing of fluid from the input channels.

FIG. 6 illustrates an FTEP device in which the flow of the fluid introduced into the flow channel from the input channel(s) is focused, e.g., using an immiscible fluid such as an oil or a stream of air to narrow the stream of the fluid containing the cells and the nucleic acids as it passes by the electrodes. FIG. 6 shows a cutaway view from the top of the FTEP device 600, with the inlet 602, outlet 604, and the electrodes 608 positioned between the first inlet channel 602 and outlet 604. The flow focusing 630 is effected by an immiscible fluid, where the electrodes 608 form a narrowed portion of flow channel 606. (For methods and inlet configurations relevant to flow focusing, see, e.g., US Pub. Nol. 2010/0184928 to Kumacheva.)

Figure 7A:
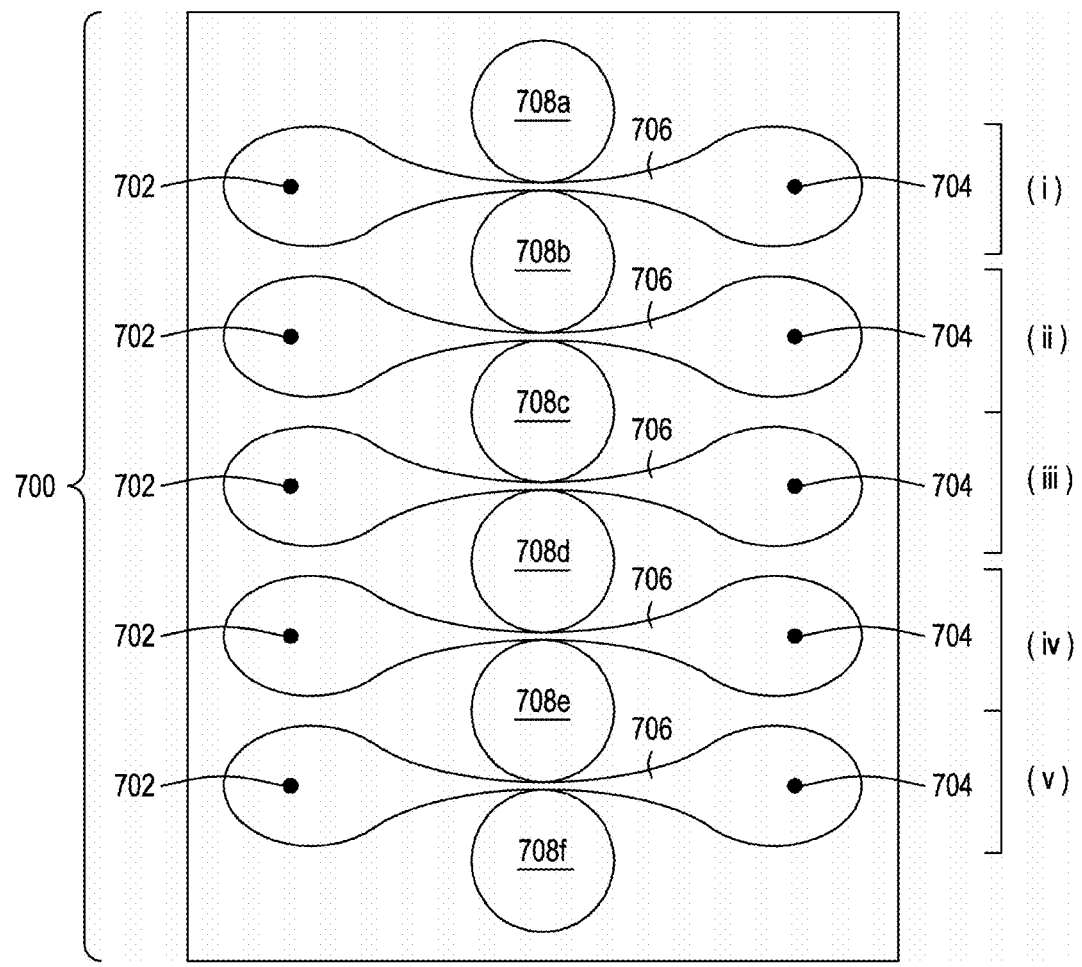
FIG. 7A is an illustration of a top view of a cross section of a first multiplexed embodiment of the FTEP devices of the disclosure.
Figure 7B:
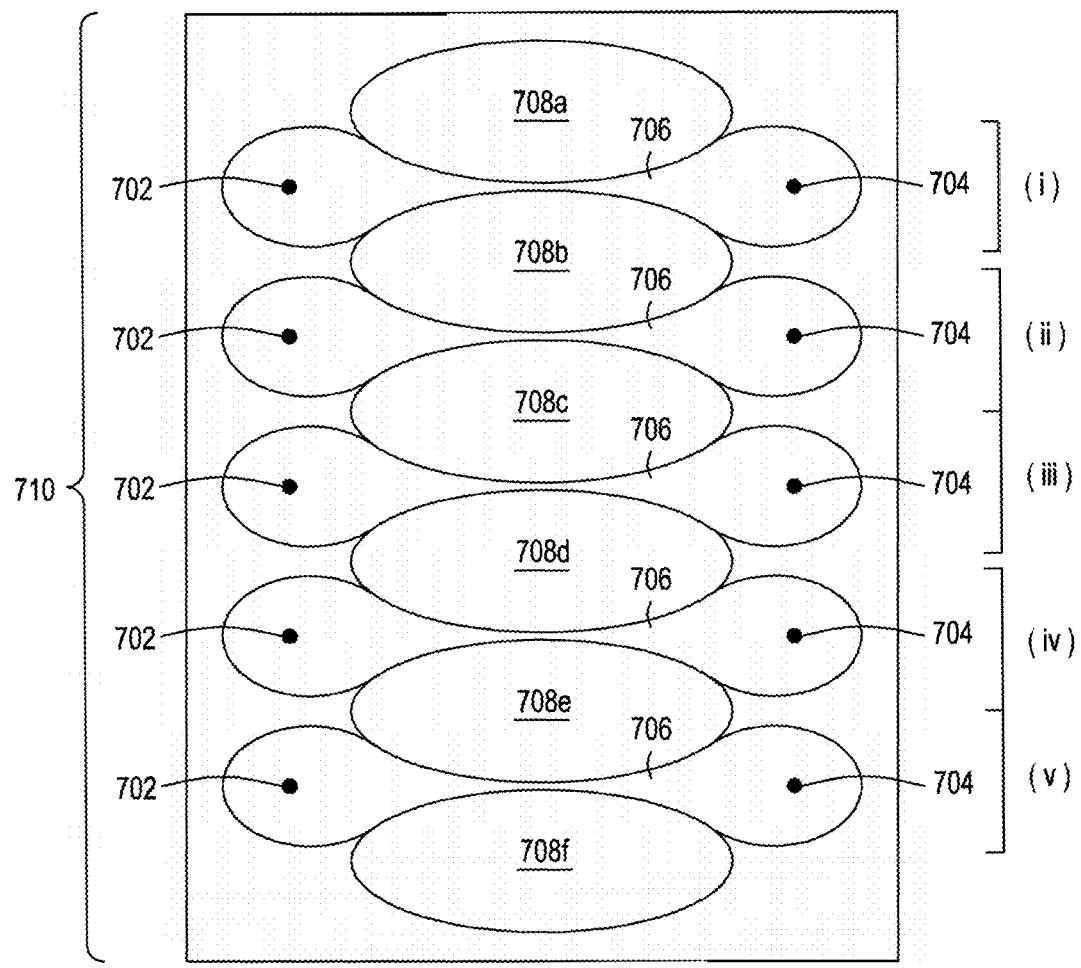
FIG. 7B is an illustration of a top view of a cross section of a second multiplexed embodiment of the devices of the disclosure.

Multiplexed embodiments of exemplary FTEP devices are illustrated in FIGS. 7A-7E. FIG. 7A illustrates a top view of a cross section of a first multiplexed aspect of the FTEP devices of the disclosure. The FTEP device in FIG. 7A is a multiplexed FTEP device 700 in which parallel flow channels 706 for each FTEP module are defined in part by shared cylindrical electrodes 708a-708f forming devices (i), (ii), (iii), (iv), and (v). Each flow channel 706 has an inlet 702 for introducing different sets of cells and/or nucleic acids into the FTEP units and an outlet 704 for removing the transformed cells from the FTEP units. Adjacent units share electrodes, where the electrodes alternate charge, e.g., +/−/+/−/+ (that is, if electrode 708a is +, electrode 708b is −, electrode 708c is +, electrode 708d is −, and so on). FIG. 7B is an illustration of a top view of a cross section of a second multiplexed embodiment of the FTEP devices 710 of the disclosure. This is a multiplexed device 710 in which parallel flow channels 706 are defined in part by shared oval electrodes 708a-708f. Each flow channel 706 has an inlet 702 for introducing different sets of cells and/or nucleic acids into the flow channels 706, and an outlet for removing the transformed cells from FTEP units (i), (ii), (iii), (iv), and (v). Again, adjacent devices share electrodes, where the electrodes alternate charge, e.g., +/−/+/−/+.

Figure 7C:
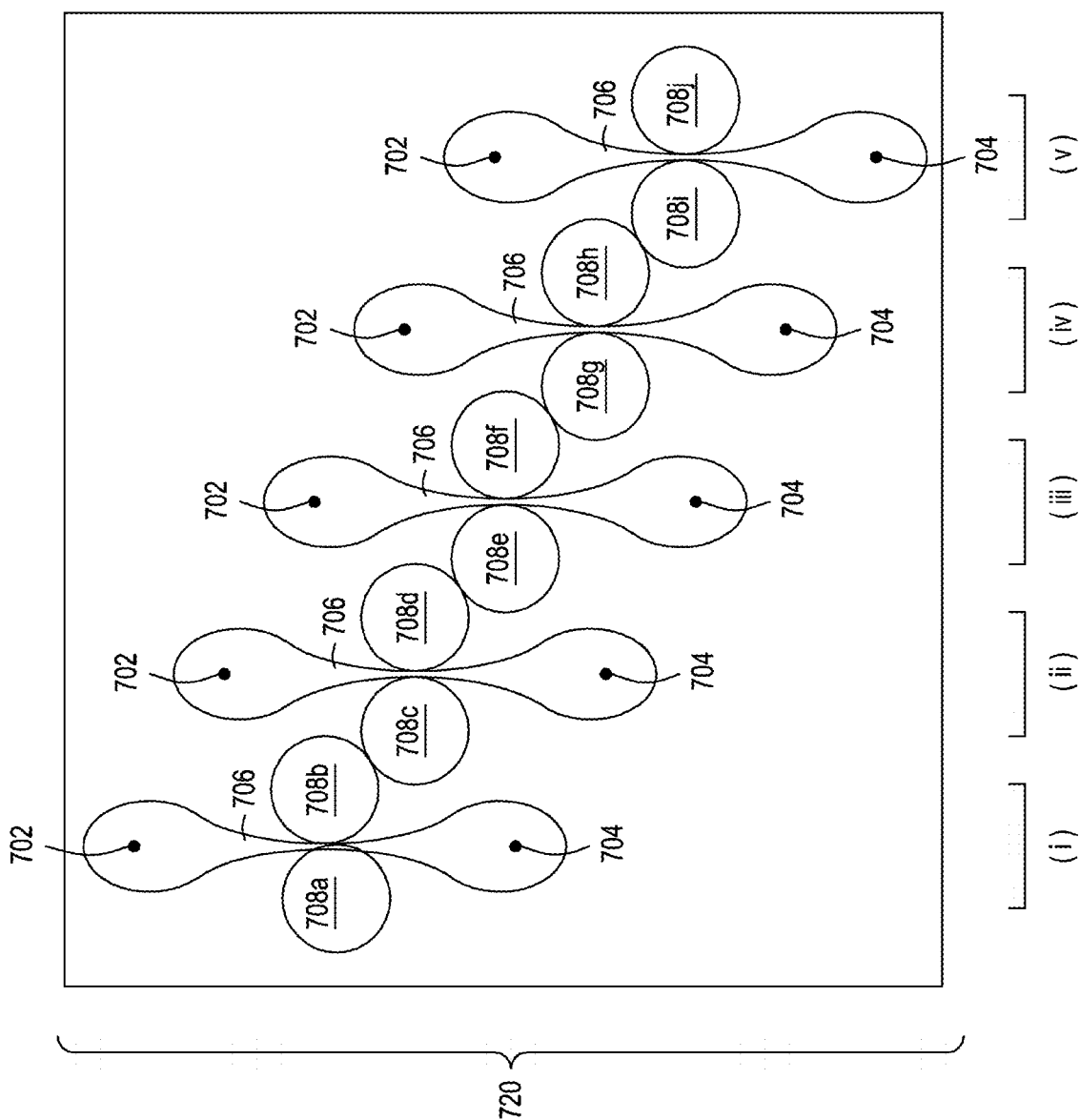
FIG. 7C is an illustration of a top view of a cross section of a third multiplexed embodiment of the devices of the disclosure.
Figure 7D:
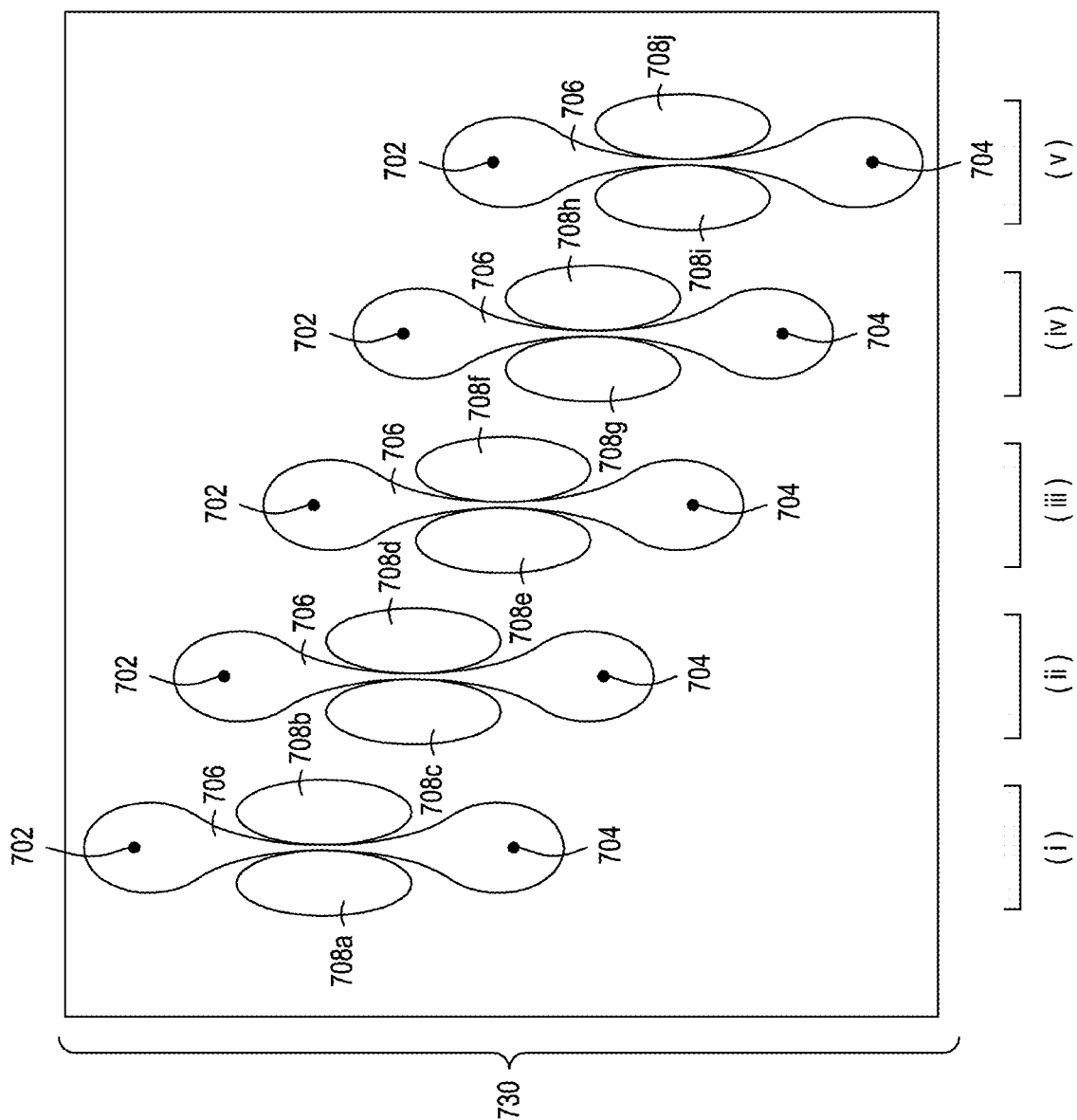
FIG. 7D is an illustration of a top view of a cross section of a fourth multiplexed embodiment of the devices of the disclosure.
Figure 7E:
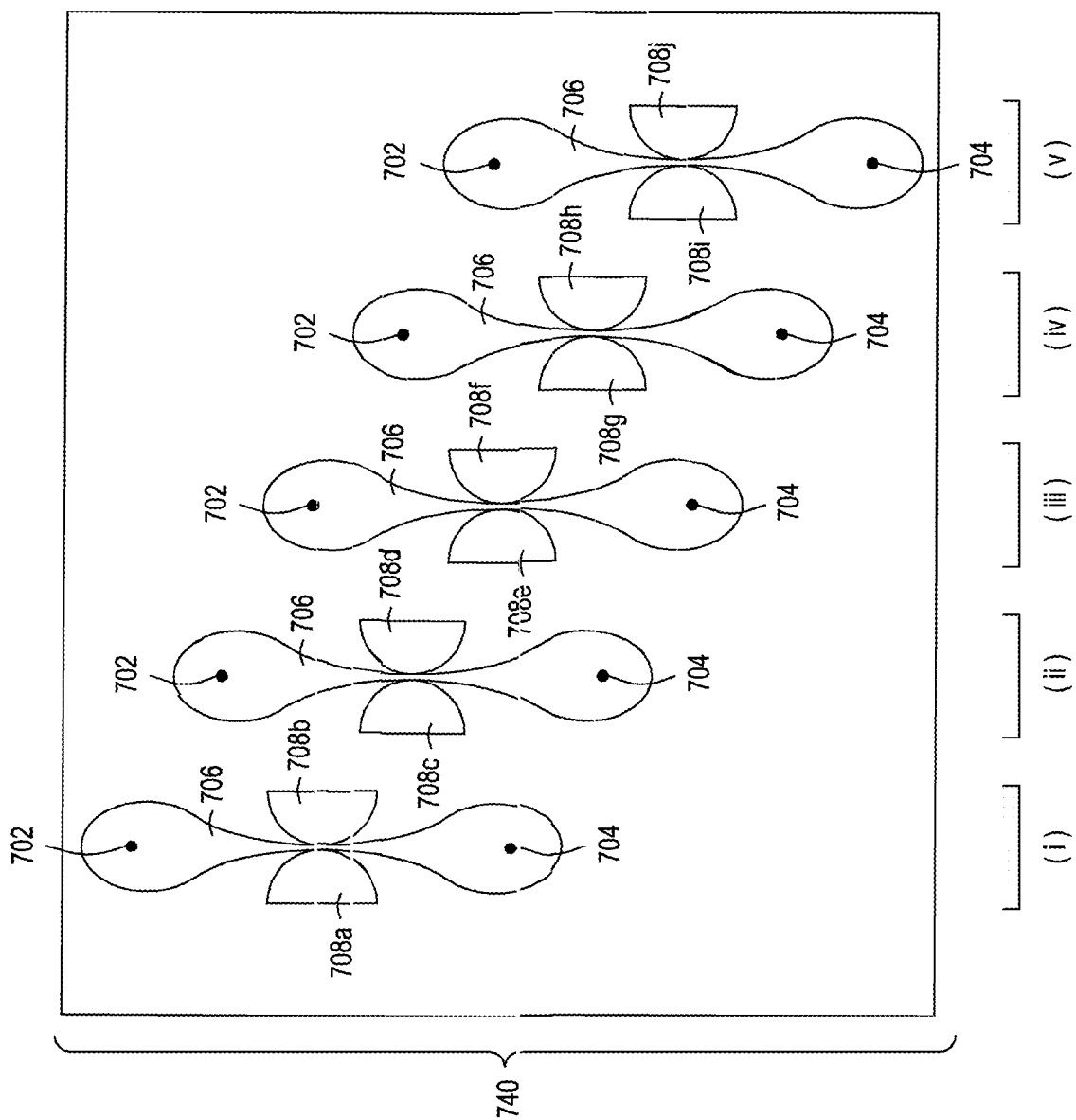
FIG. 7E is an illustration of a top view of a cross section of a fifth multiplexed embodiment of the devices of the disclosure.

FIG. 7C is an illustration of a top view of a cross section of a third multiplexed embodiment of the FTEP devices of the disclosure. In this exemplary multiplexed FTEP device 720, the individual FTEP units are staggered. The parallel flow channels 706 are defined in part by individual cylindrical electrodes 708a-708j that are not shared as shown in FIGS. 7A and 7B. Each flow channel 706 has its own pair of electrodes 708, an inlet 702 for introducing different sets of cells and/or nucleic acids into the FTEP device, and an outlet for removing transformed cells from the FTEP units (i), (ii), (iii), (iv), and (v). FIG. 7D is an illustration of a top view of a cross section of another exemplary multiplexed FTEP device. In this multiplexed FTEP device 730, staggered, parallel flow channels 706 are defined in part by individual oval electrodes 708a-708j. Each flow channel 706 has its own un-shared pair of electrodes 708 (e.g., 708a/708b, 708c/708d, 708e/708f, 708g/708h, and 708i/708j), an inlet 702 for introducing different sets of cells and/or nucleic acids into the FTEP units, and an outlet 704 for removing transformed cells from the FTEP units. FIG. 7E is an illustration of a top view of a cross section of another exemplary multiplexed FTEP device. In this exemplary multiplexed device 740, staggered, parallel flow channels 706 are defined in part by individual half-cylindrical electrodes 708a-708j. Each flow channel 706 has its own pair of electrodes 708, a separate inlet 702 for introducing different sets of cells and/or nucleic acids into the FTEP unit, and an outlet 704 for removing the transformed cells from the FTEP unit.

Figure 8A:
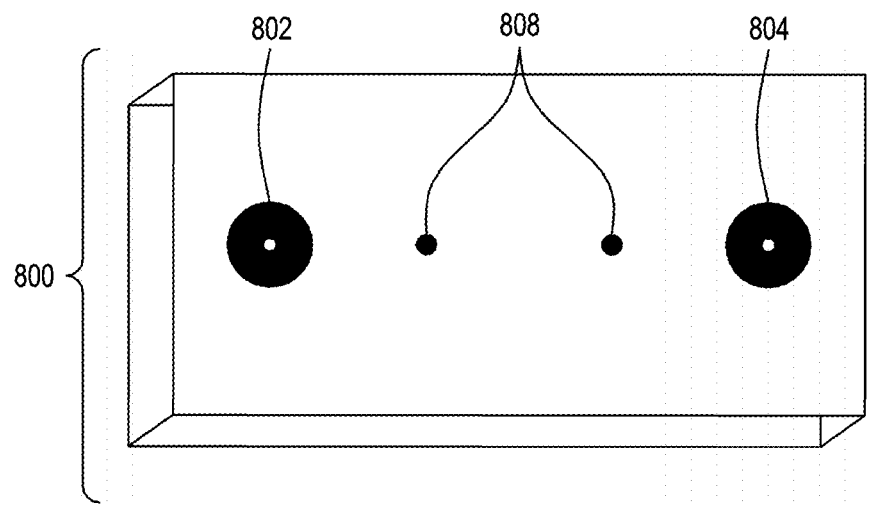
FIG. 8A is an illustration of a top view of yet another embodiment of the FTEP devices of the disclosure where the electrodes are placed on either end of the narrowed region of the flow channel rather than on either side and defining the narrowed region of the flow channel.
Figure 8B:
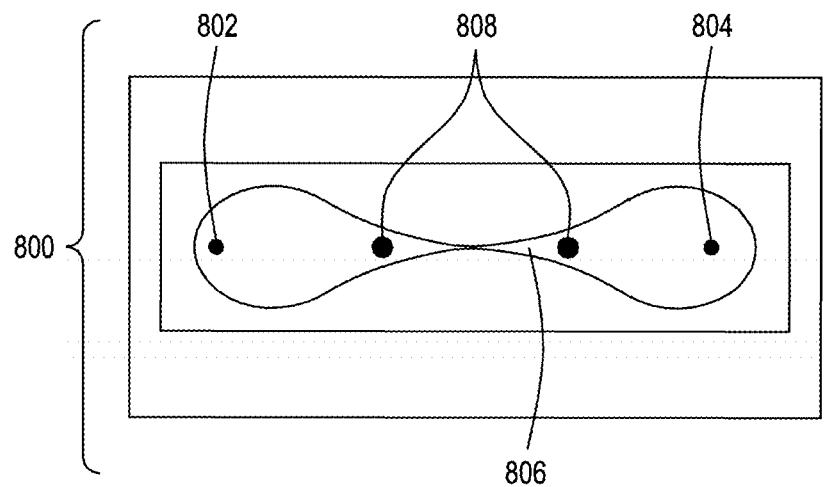
FIG. 8B is an illustration of the top view of a cross section of the embodiment of the device shown in FIG. 8A.
Figure 8C:
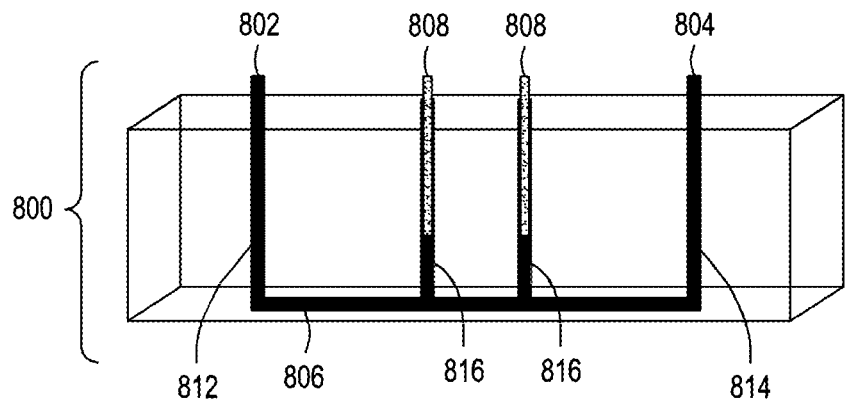
FIG. 8C is an illustration of a side view of a cross section of the embodiment of the device shown in FIGS. 8A and 8B.
Figure 8D:
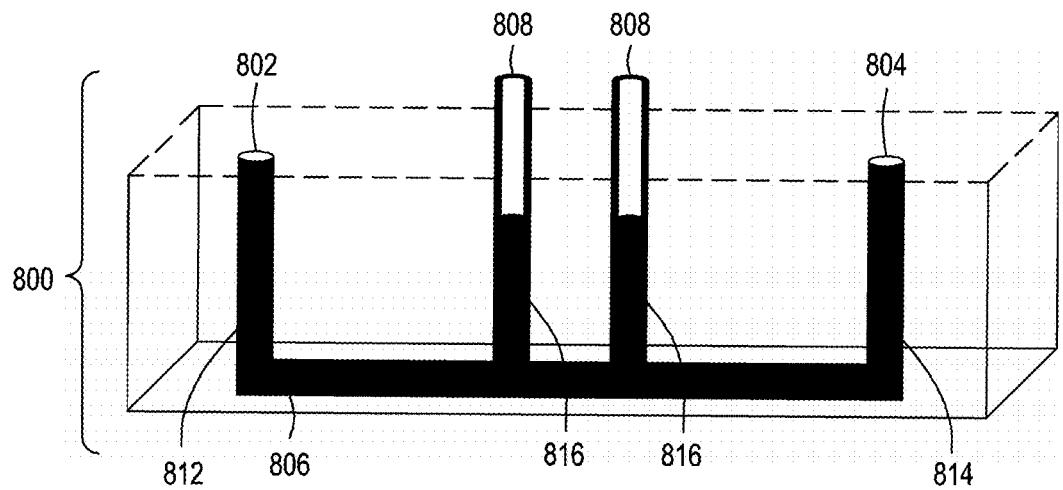
FIG. 8D is an illustration of a side view of a cross section of the bottom half of the embodiment of the devices shown in FIGS. 8A, 8B and 8C.
Figure 8E:
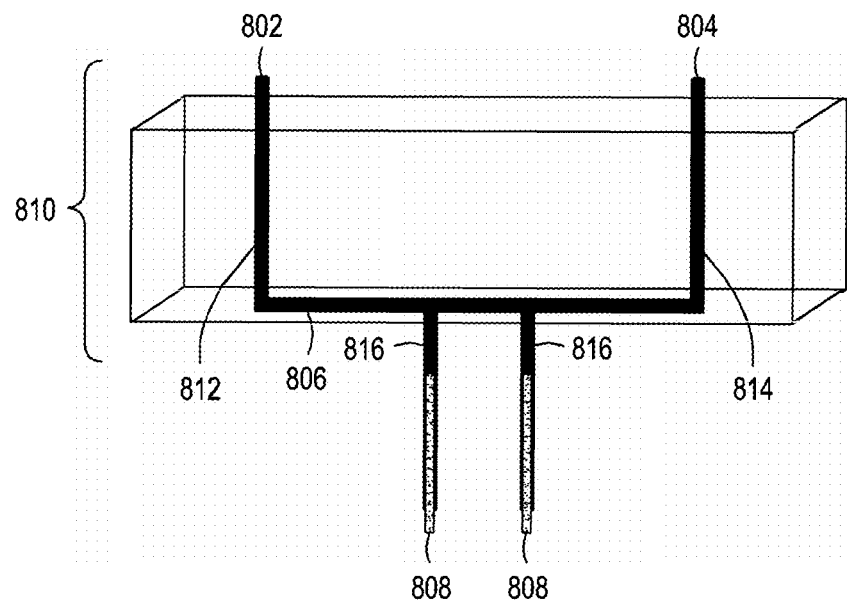
FIG. 8E is an illustration of a side view of a cross section of a variation of the embodiment of the devices shown in FIGS. 8A-8D where here the electrodes are positioned on the bottom of the FTEP device, on the opposite surface from the inlet and outlet.
Figure 8F:
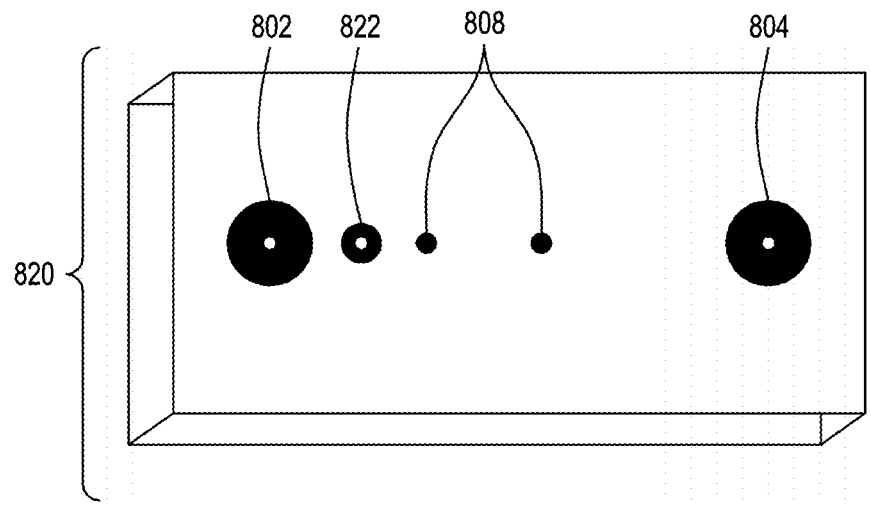
FIG. 8F is an illustration of a top view of yet another embodiment of the FTEP devices of the disclosure.
Figure 8G:
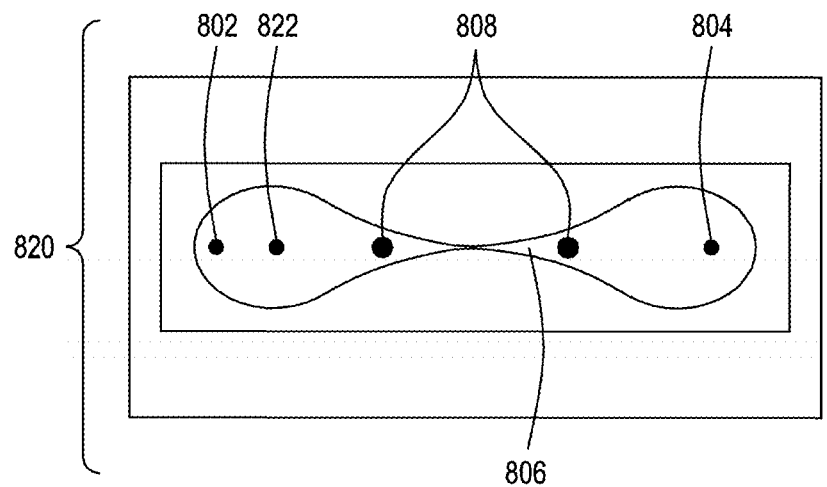
FIG. 8G an illustration of the top view of a cross section of the embodiment of the device shown in FIG. 8F.
Figure 8H:
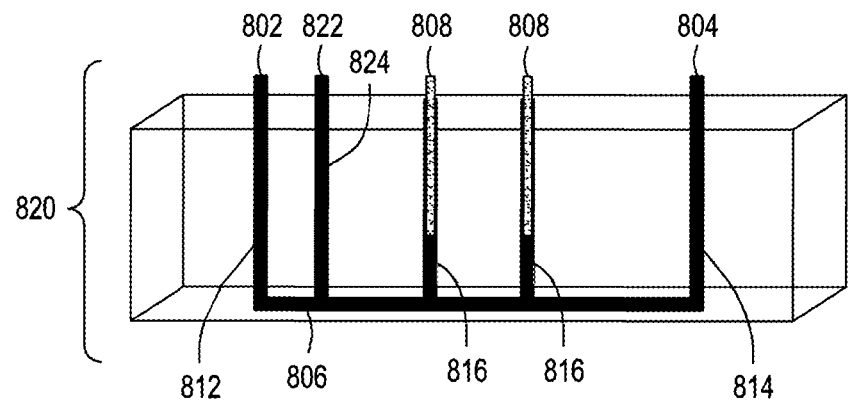
FIG. 8H is an illustration of a side view of a cross section of one variation of the embodiment of the device shown in FIGS. 8F and 8G.
Figure 8I:
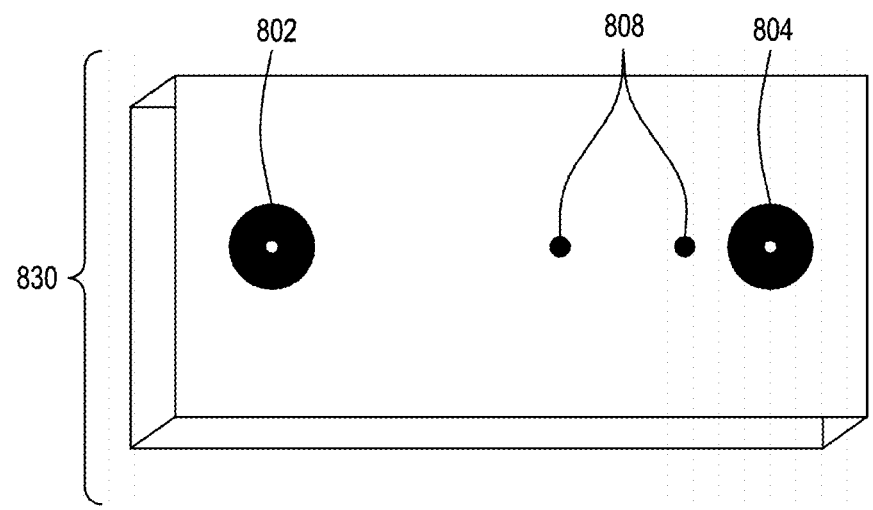
FIG. 8I is an illustration of a top view of an embodiment of the FTEP devices of the disclosure.
Figure 8J:
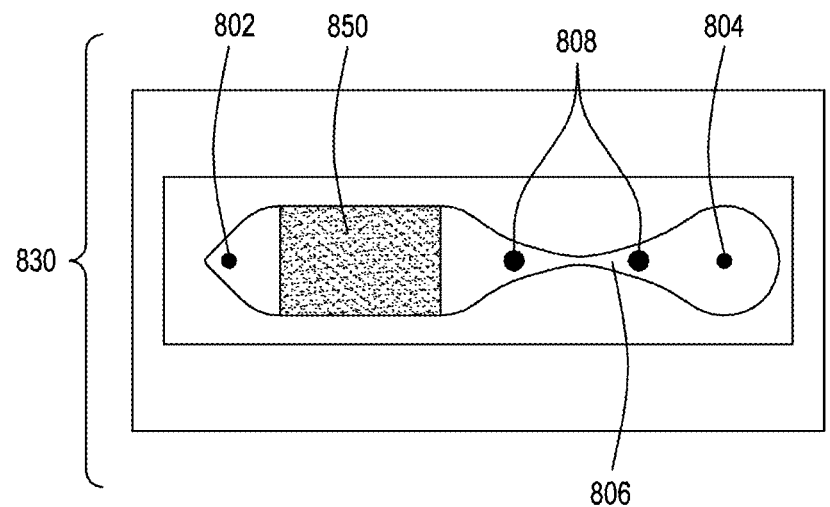
FIG. 8J is an illustration of the top view of a cross section of the embodiment of the device shown in FIG. 8I where in this embodiment the FTEP device comprises a filter.
Figure 8K:
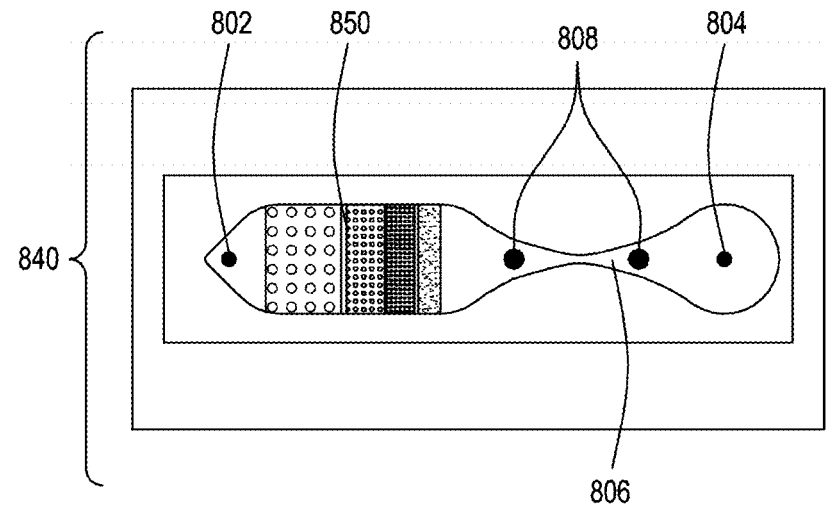
FIG. 8K is an illustration of the top view of a cross section of a variation of the embodiment of the device shown in FIGS. 8I and 8J.
Figure 8L:
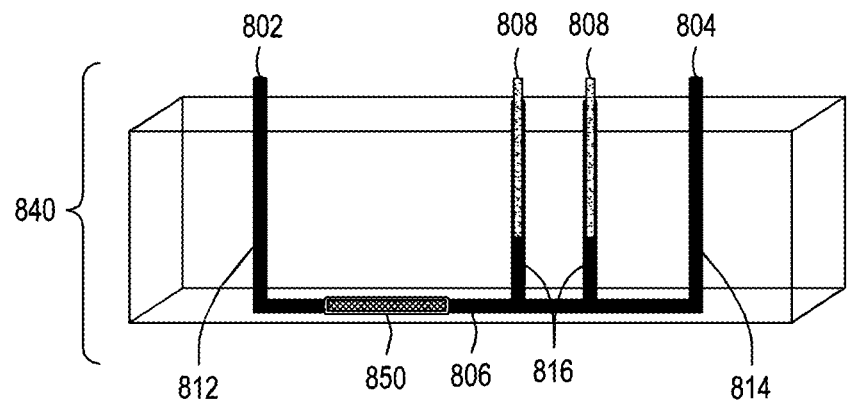
FIG. 8L is an illustration of a side view of a cross section of the embodiment of the devices shown in FIGS. 8I-8K.
Figure 8M:
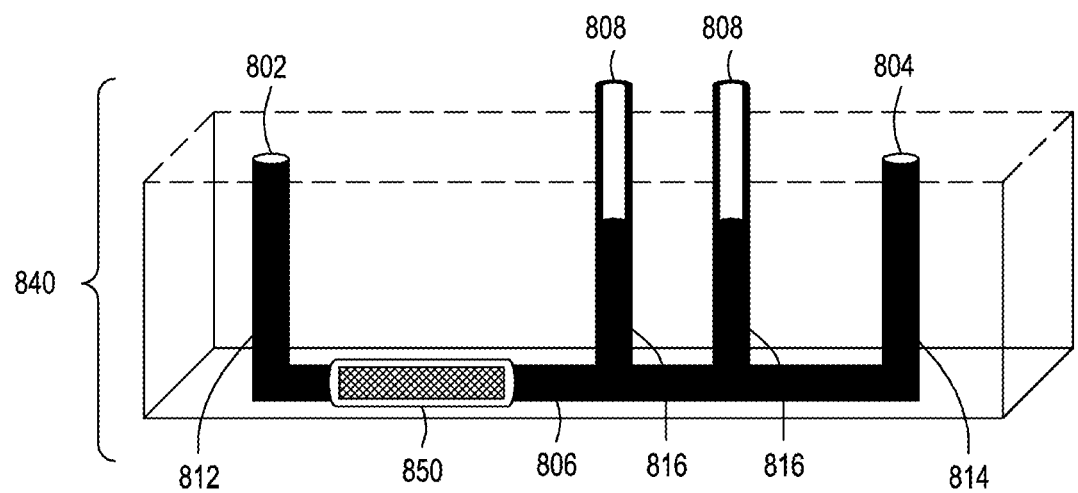
FIG. 8M is an illustration of a side view of a cross section of the bottom half of the embodiment of the devices shown in FIGS. 8I-8L.
Figure 8N:
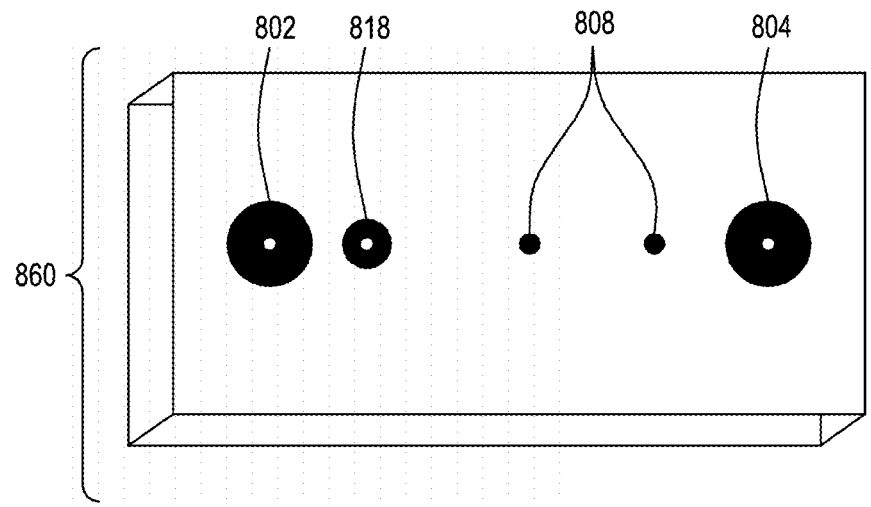
FIG. 8N is an illustration of a top view of yet another embodiment of the FTEP devices of the disclosure.
Figure 8O:
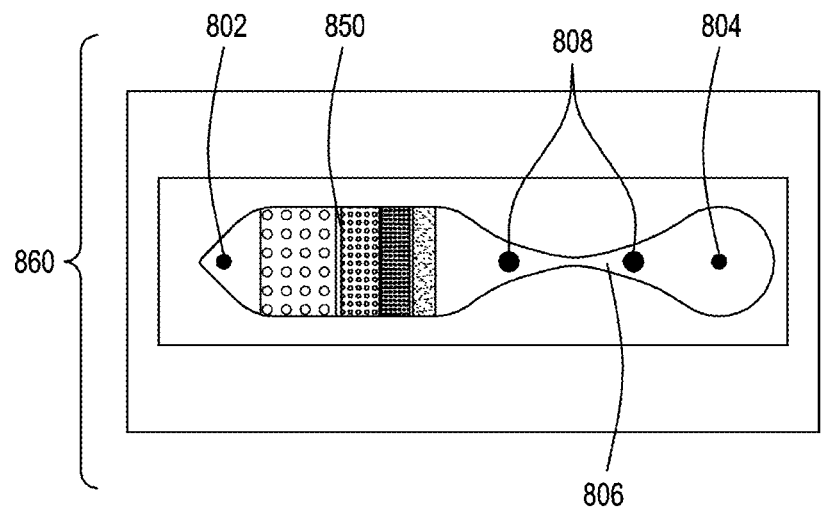
FIG. 8O is an illustration of the top view of a cross section of the embodiment of the device shown in FIG. 8N.
Figure 8P:
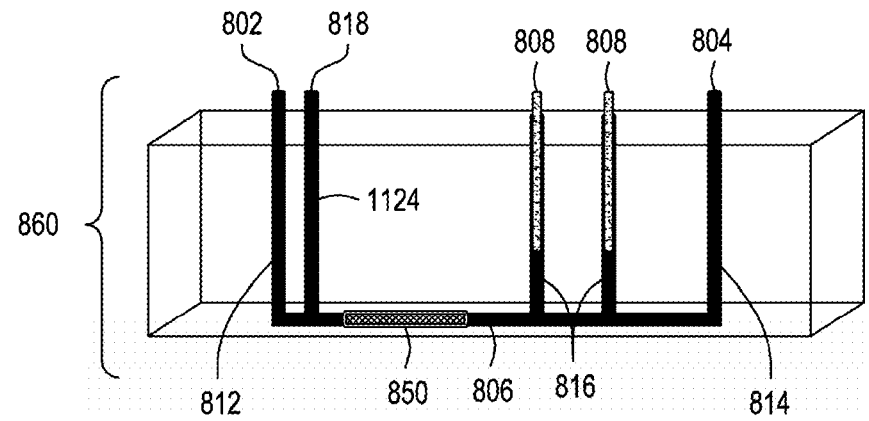
FIG. 8P is an illustration of a side view of a cross section of the embodiment of the device of the disclosure shown in FIGS. 8N-8O.
Figure 8Q:
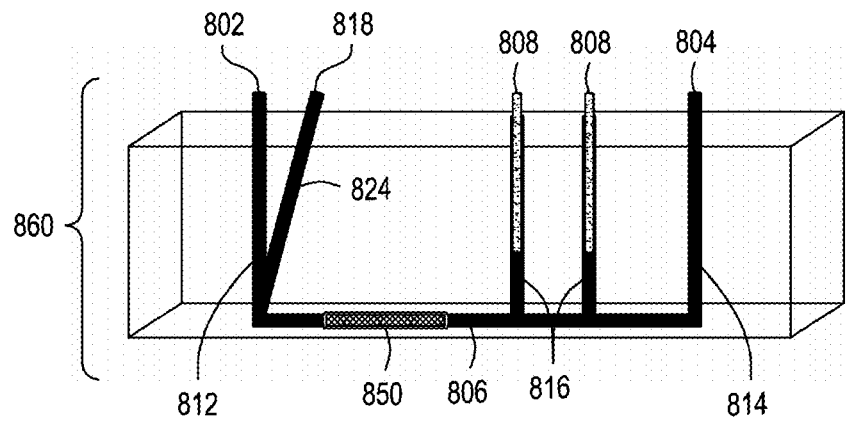
FIG. 8Q is an illustration of a side view of a cross section of a variation on the embodiment of the device shown in FIGS. 8N-8O.
Figure 8R:
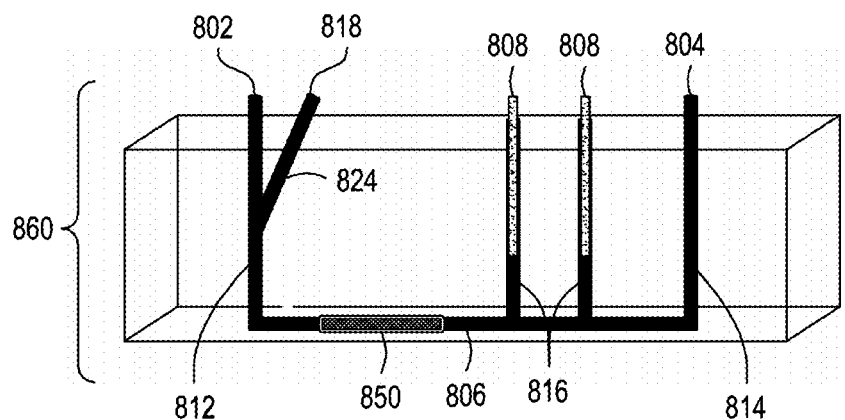
FIG. 8R is an illustration of a side view of a cross section of another variation on the embodiment of the device shown in FIGS. 8N-8Q.
Figure 8S:
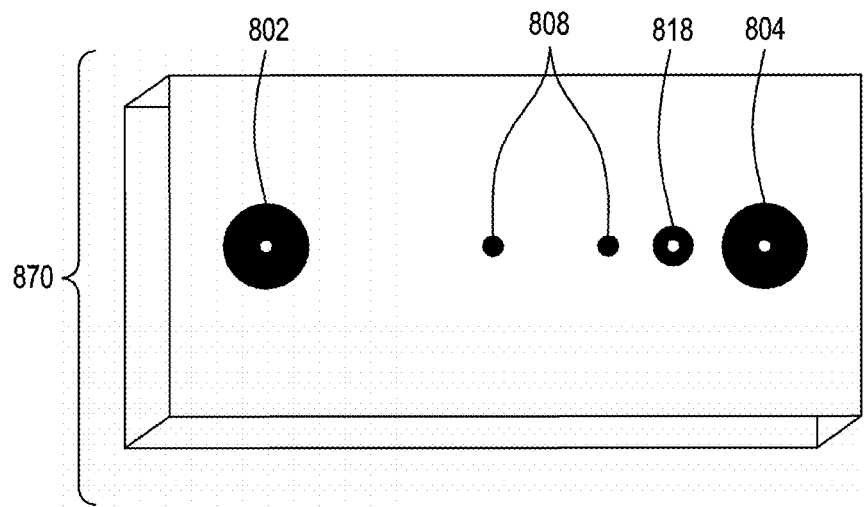
FIG. 8S is an illustration of the top view of a cross section of yet another embodiment of the FTEP devices of the disclosure.
Figure 8T:
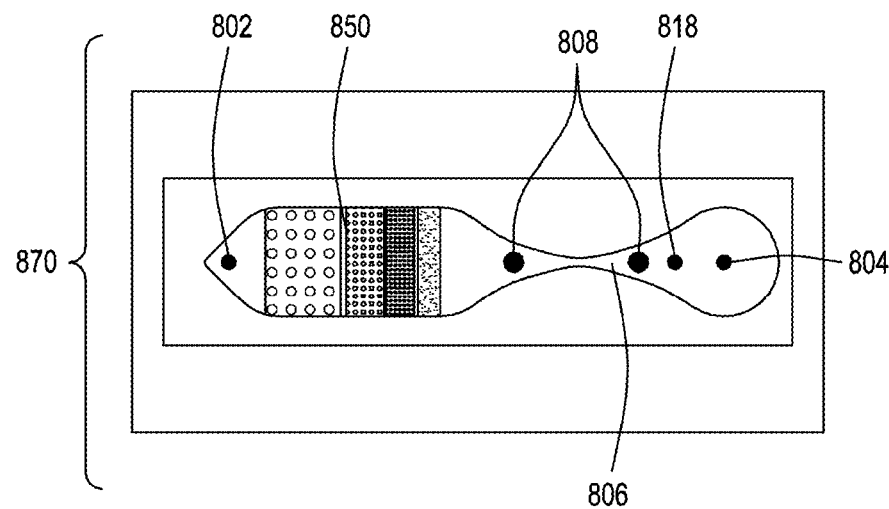
FIG. 8T is an illustration of the top view of a cross section of the embodiment of the device shown in FIG. 8S.
Figure 8U:
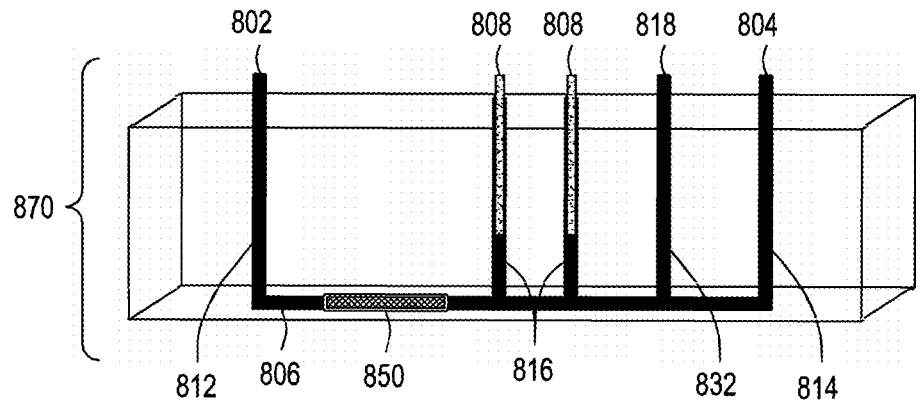
FIG. 8U is an illustration of a side view of a cross section of the embodiment of the device shown in FIGS. 8S and 8T.

Additional embodiments of the FTEP devices of the disclosure are illustrated in FIGS. 8A-8U. Note that in the FTEP devices in FIGS. 8A-8U the electrodes are not positioned on either side of the flow channel to narrow the flow channel; instead, the electrodes are placed such that a first electrode is placed between the inlet and the narrowed region of the flow channel, and the second electrode is placed between the narrowed region of the flow channel and the outlet. FIG. 8A shows a top planar view of an FTEP device 800 having an inlet 802 for introducing a fluid containing cells and nucleic acid into FTEP device 800 and an outlet 804 for removing the transformed cells from the FTEP following electroporation. The electrodes 808 are introduced through channels (not shown) in the device. FIG. 8B shows a cutaway view from the top of the FTEP device 800, with the inlet 802, outlet 804, and electrodes 808 positioned with respect to a flow channel 806. FIG. 8C shows a side cutaway view of FTEP device 800 with the inlet 802 and inlet channel 812, and outlet 804 and outlet channel 814. The electrodes 808 are positioned in electrode channels 816 so that they are in fluid communication with the flow channel 806, but not directly in the path of the cells traveling through the flow channel 806. Again note that the first electrode is placed between the inlet and the narrowed region of the flow channel, and the second electrode is placed between the narrowed region of the flow channel and the outlet.

An expanded side cutaway view of the bottom portion of the device 800 in FIG. 8D shows that the electrodes 808 in this aspect of the device are positioned in the electrode channels 816 which are generally perpendicular to the flow channel 806 such that the fluid containing the cells and nucleic acid flows from the inlet channel 812 through the flow channel 806 to the outlet channel 814, and in the process fluid flows into the electrode channels 816 to be in contact with the electrodes 808. In this aspect, the inlet channel, outlet channel and electrode channels all originate from the same planar side of the device, as shown in FIGS. 8C and 8D. In certain aspects, however, such as that shown in FIG. 8E, the electrodes are introduced from a different planar side of the FTEP device than the inlet and outlet channels. Here, the electrodes 808 in this alternative aspect of FTEP device 810 are positioned in the electrode channels 816 perpendicular to the flow channel 806 such that fluid containing the cells and nucleic acid flow from the inlet channel 812 through the flow channel 806 to the outlet channel 814. The cells and nucleic acid in buffer flow into the electrode channels 816 to be in contact with both electrodes 808; however, the electrodes 808 are not directly in flow channel 806. In this aspect, the inlet channel and outlet channel originate from a different planar side of the device than do the electrodes and electrode channels.

FIGS. 8F-8H illustrate yet another aspect of the FTEP devices of the disclosure. FIG. 8F shows a top planar view of an FTEP device 820 having a first inlet 802 for introducing a fluid containing cells into FTEP device 820 and an outlet 804 for removing the transformed cells from the FTEP device 820 following electroporation. However, in this FTEP device, there is a second inlet 822 for introducing nucleic acid to be electroporated to the cells. The electrodes 808 are introduced through channels (not shown). FIG. 8G shows a cutaway view from the top of the FTEP device 820, with the first inlet 802, second inlet 822, outlet 804, and the electrodes 808 positioned with respect to the flow channel 806. FIG. 8H shows a side cutaway view of FTEP device 820 with inlets 802, 822 and inlet channels 812, 824 and outlet 804 and outlet channel 814. The electrodes 808 are positioned in the electrode channels 816 so that they are in fluid communication with the flow channel 806, but not substantially in the path of the cells traveling through the flow channel 806. The electrodes 808 in this aspect of the FTEP device 820 are positioned in the electrode channels 816 where the electrode channels 816 are generally perpendicular to the flow channel 806 such that fluid containing the cells and fluid containing the nucleic acids flow from the inlets 802, 822 through the inlet channels 812, 824 into the flow channel 806 and through to the outlet channel 814, and in the process the cells and nucleic acid in medium flows into the electrode channels 816 to be in contact with the electrodes 808. One of the two electrodes 808 and electrode channels 816 is positioned between inlets 802 and 822 and inlet channels 812 and 824 and the narrowed region (not shown) of flow channel 806, and the other electrode 808 and electrode channel 816 is positioned between the narrowed region (not shown) of flow channel 806 and the outlet channel 814 and outlet 804. In FIG. 8H, the inlet channel, outlet channel and electrode channels all originate from the same planar side of the device, although the electrodes (and inlets and outlet) can also be configured to originate from a different planar sides of the FTEP device such as illustrated in FIG. 8E.

FIGS. 8I-8M illustrate yet another embodiment of the devices of the disclosure. FIG. 8I shows a top planar view of an electroporation device 830 having an inlet 802 for introducing a fluid containing cells and nucleic acid into the FTEP device 830 and an outlet 804 for removal of the transformed cells from the FTEP device 8300 following electroporation. The electrodes 808 are introduced through channels (not shown) machined into the device. FIG. 8J shows a cutaway view from the top of the device 830, showing an inlet 802, an outlet 804, a filter 850 of substantially uniform density, and electrodes 808 positioned with respect to the flow channel 806. FIG. 8K shows a cutaway view from the top of an alternative configuration 840 of the device 830, with an inlet 802, an outlet 804, a filter 850 of increasing gradient density, and electrodes 808 positioned with respect to the flow channel 806. In FIGS. 8I-8M, like FIGS. 8F-8H, the first electrode is placed between the inlet and the narrowed region of the flow channel, and the second electrode is placed between the narrowed region of the flow channel and the outlet. In some embodiments such as those depicted in FIGS. 8I-8M, the FTEP devices comprise a filter disposed within the flow channel positioned in the flow channel after the inlet channel and before the first electrode channel. The filter may be substantially homogeneous in porosity (e.g., have a uniform density as in FIG. 8J); alternatively, the filter may increase in gradient density where the end of the filter proximal to the inlet is less dense, and the end of the filter proximal to the outlet is more dense (as shown in FIG. 8K). The filter may be fashioned from any suitable and preferably inexpensive material, including porous plastics, hydrophobic polyethylene, cotton, glass fibers, or the filter may be integral with and fabricated as part of the FTEP device body (see, e.g., FIG. 10E).

FIG. 8L shows a side cutaway view of the device 840 with an inlet 802 and an inlet channel 812, and an outlet 804 and an outlet channel 814. The electrodes 808 are positioned in the electrode channels 816 so that they are in fluid communication with the flow channel 806, but not directly in the path of the cells traveling through flow channel 806. Note that filter 850 is positioned between inlet 802 and inlet channel 812 and electrodes 808 and electrode channels 816. An expanded side cutaway view of the bottom portion of the FTEP device 840 in FIG. 8M shows that the electrodes 808 in this aspect of the FTEP device 840 are positioned in the electrode channels 816 and perpendicular to the flow channel 806 such that fluid containing the cells and nucleic acid flows from the inlet channel 812 through the flow channel 806 to the outlet channel 814, and in the process fluid flows into the electrode channels 816 to be in contact with both electrodes 808. In FIGS. 8L and 8M, the inlet channel, outlet channel and electrode channels all originate from the same planar side of the device, although the electrodes (and the inlets and outlet) can also be configured to originate from a different planar side such as illustrated in FIG. 8E.

FIGS. 8N-8R illustrate other embodiments of the FTEP devices of the disclosure. FIG. 8N shows a top view of an FTEP device 860 having a first inlet 802 for introducing a fluid containing cells into the FTEP device and a second inlet 818 for introducing a fluid containing nucleic acids to be introduced to the cells into the FTEP device, electrodes 808 positioned in electrode channels (not shown), and an outlet 804 for removal of the transformed cells following electroporation. FIG. 8O shows a cutaway view from the top of the device 860, comprising a first inlet 802, second inlet 818, outlet 804, filter 850, and electrodes 808 positioned with respect to the flow channel 806. Again note that the electrodes 808 are positioned so that the first electrode is on the "inlet end" of the narrowed region in flow channel 806 and the second electrode is on the "outlet end" of the narrowed region in flow channel 806. FIG. 8P shows a first side cutaway view of an embodiment of the device 860 with the first inlet 802 and second inlet 818 positioned as shown in FIG. 8N. The first inlet channel 812 and second inlet channel 824 meet separately with the flow channel 806 prior to encountering filter 850, and the liquid flows from the inlet channels 812 and 824 through the flow channel 806 (and filter 850) to the outlet channel 814 and outlet 804. Note that in some embodiments, electrodes 808 may be positioned in electrode channels 816 such that electrodes 808 are flush with the walls of flow channel 806 (e.g., see FIG. 10F(iii)). Alternatively, electrodes 808 may extend a minimal distance into flow channel 806; however, in doing so electrodes 808 do not extend into flow channel 806 to the extent that the electrodes impede the flow of the cells through the flow channel.

FIG. 8Q shows a side cutaway view of a variation of the embodiment of the FTEP device 860 shown in FIGS. 8N-8P with the first inlet 802 and second inlet 818 positioned as shown in FIG. 8N. The first inlet channel 812 and second inlet channel 824 intersect with flow channel 806 at a three-way junction with flow channel 806 and prior to encountering filter 850. The liquid flows through the flow channel 806 to the outlet channel 824 and outlet 804. The electrodes 808 are positioned in the electrode channels 816 so that they are in fluid communication with the flow channel 806, but not directly in the path of the cells traveling through the flow channel 806. Again, the electrodes 808 are positioned so that the first electrode is on the "inlet end" of the narrowed region in flow channel 806 and the second electrode is on the "outlet end" of the narrowed region in flow channel 806. FIG. 8R shows a side cutaway view of yet another variation on the embodiment of the FTEP device 860 shown in FIGS. 8N-8P. The first inlet channel 812 and second inlet channel 826 intersect at a junction into a single channel prior to intersecting flow channel 806. The fluids flow from the inlets 802 and 818, through the inlet channels 812 and 826, into and through flow channel 806 and the filter 850, into electrode channels 816 (such that electrodes 808 are in fluid communication with flow channel 806) and continuing through flow channel 806 to the outlet channel 814 and finally to the outlet 804 where the transformed cells are removed from the FTEP device 860. Again in this embodiment, the electrodes 808 are positioned in the electrode channels 816 so that they are in fluid communication with the flow channel 806, but not directly in the flow path of the cells traveling through the flow channel 806. Although each of FIGS. 8P-8R show the inlet channels, outlet channel and electrode channels originating from the same planar side of the device, all of the inlets, outlet and electrodes in each of these aspects can also be configured to originate from different planar sides of the FTEP device.

FIGS. 8S-8U illustrate another embodiment of the FTEP devices of the disclosure. FIG. 8S shows a top view of an electroporation device 870 having a first inlet 802 for introducing a fluid containing cells into FTEP device 870, a second inlet 818 for introducing nucleic acids to be porated into the cells into FTEP device 870, and an outlet 804 for removing transformed cells from FTEP device 870 following electroporation. The electrodes 808 are introduced through channels (not shown) machined into the device and are positioned between the first inlet 802 and the second inlet 818. FIG. 8T shows a cutaway view from the top of the device 870, with the first inlet 802, second inlet 818, outlet 804, and the electrodes 808 positioned with respect to the flow channel 806. Additionally, the FTEP device depicted in FIG. 8T comprises a filter 850 disposed between the first inlet 802 and the first electrode 808 and before the narrowed region of flow channel 806. Filter 850 in this embodiment has a gradient of pore sizes, from large to small (moving from the inlet 802 toward the narrowed portion of flow channel 806. FIG. 8U shows a side cutaway view of FTEP device 870 comprising a first inlet 802 and first inlet channel 812, a filter 850, a second inlet 818 and second inlet channel 832, and an outlet 804 and outlet channel 814. The electrodes 808 are positioned in the electrode channels 816 perpendicular to flow channel 806 and between the first and second inlets. The electrodes 808 are in fluid communication with flow channel 806, but not in the flow channel and thus in the path of the cells traveling through flow channel 806. Nucleic acids are added to FTEP device 870 via the second inlet 818 and through the second inlet channel 832 and encounter the cells after the cells are electroporated. In FIG. 8U, the inlet channels, outlet channel and electrode channels all originate from the same planar side of the device, although these features can also be configured to originate from different planar sides of FTEP device 870.

Figure 9A:
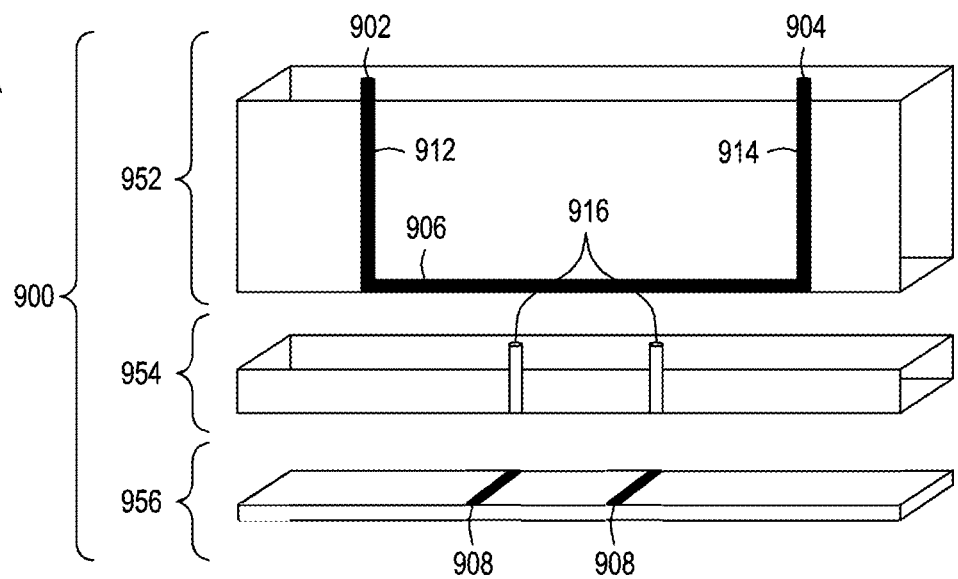
FIG. 9A is an illustration of a side view of a cross section of another embodiment of the FTEP devices of the disclosure.
Figure 9B:
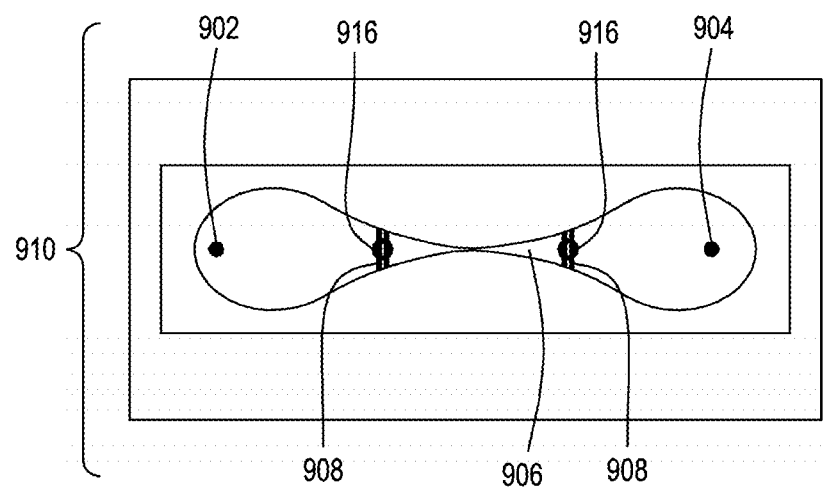
FIG. 9B is an illustration of the top view of a cross section of the embodiment of the device shown in FIG. 9A.

FIGS. 9A and 9B show the side and top cutaway views, respectively, of yet another embodiment of the invention. FIG. 9A shows a multilayer device 900 with a top layer 952 having an inlet 902 and an inlet channel 912, a flow channel 906, and outlet 904 and an outlet channel 914. The electrodes 908 are on bottom layer 956, e.g., provided as strips on a solid substrate. The middle layer 954 is a solid substrate with electrode channels 916 provided therein, and the electrode channels 916 in this aspect provide fluid communication between the electrodes 908 of bottom layer 956 and flow channel 906 of top layer 952. The cells and nucleic acids in fluid are introduced to the FTEP device 900 via inlet 902 and flow through inlet channel 912 and into flow channel 906, and then to the outlet channel 914. In the process, the fluid flows into electrode channels 916 so that electrodes 908 are in fluid contact with flow channel 906. The cells are porated as they pass through flow channel 906 between the two electrodes 908. FIG. 9B shows the top view of a cutaway 910 of the embodiment of the FTEP device 900 showing the position of the inlet 902, outlet 904, electrodes 908 and electrode channels 916 with respect to the flow channel 906. Although the electrodes are shown here as strips, they may also be configured to be other shapes, e.g., round, cylindrical, asymmetric, rectangular, or square.

Figure 9C:
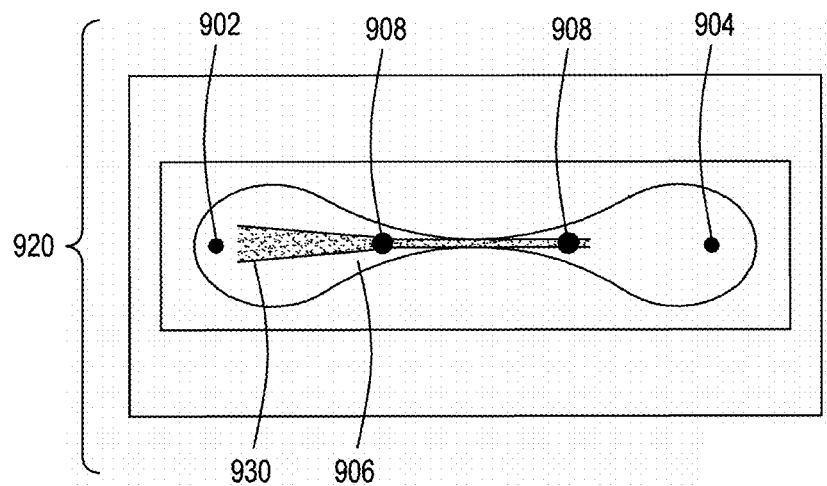
FIG. 9C is an illustration of a top view of a cross section of an embodiment of an FTEP device with a flow focusing feature.

FIG. 9C illustrates an FTEP device in which flow focusing 930 of the fluid introduced into the flow channel from the input channel(s) takes place, e.g., using an immiscible fluid such as an oil or using air to focus (narrow) the stream of the fluid containing the cells and nucleic acids as the fluid encounters the electrode channels, and the electrodes. FIG. 9C shows a cutaway view from the top of the device 920, with the first inlet 902, the flow focusing 930 of the fluid after it exits the inlet channel and enters the flow channel 906, and the electrodes 908 positioned between the inlet 902 and the outlet 904, where the electrodes 908 are positioned on either end of a narrowed portion of flow channel 906.

Figure 10A:
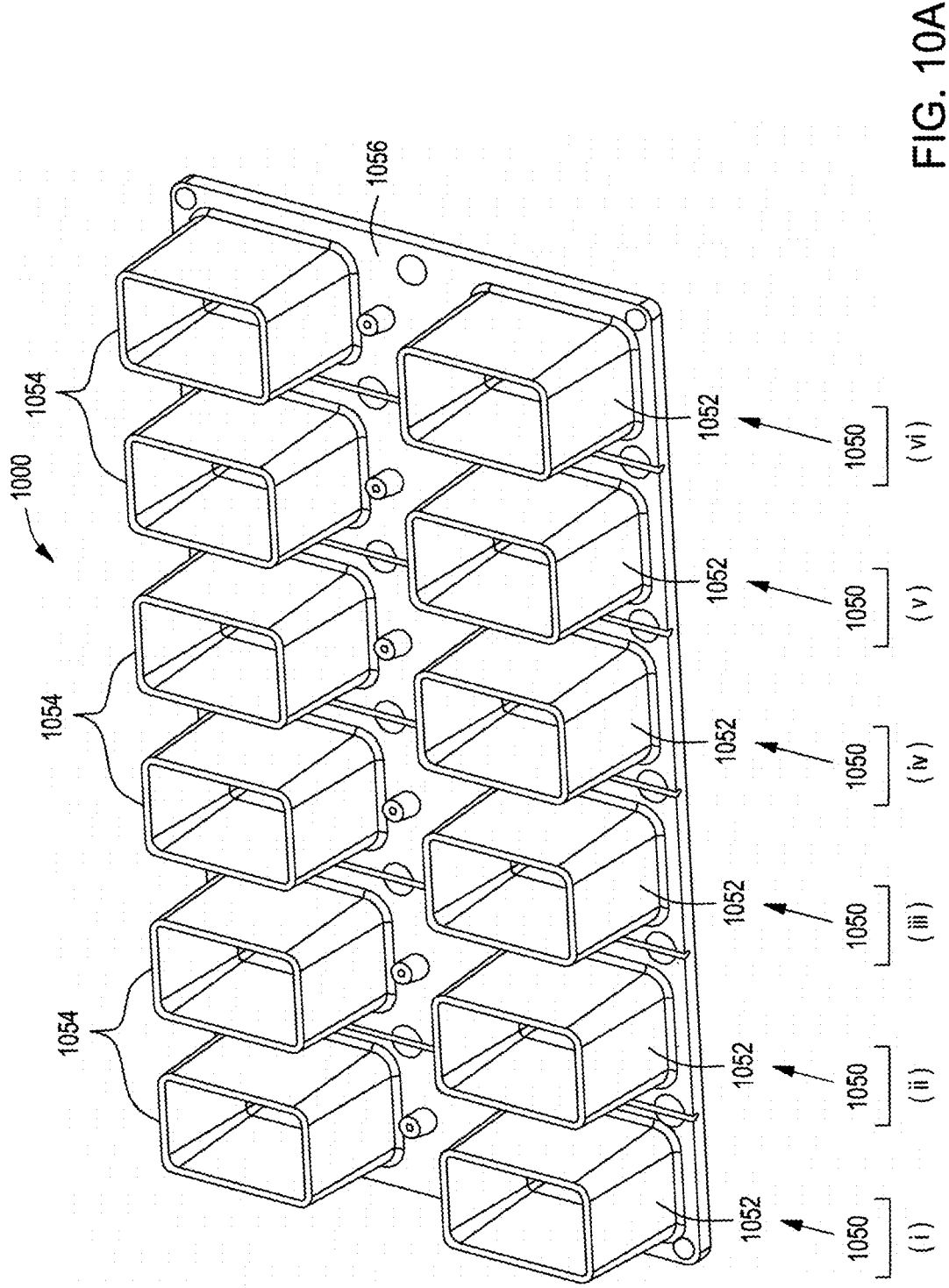
FIGS. 10A through 10C are top perspective, bottom perspective, and bottom views, respectively, of a flow-through electroporation device that may be part of a stand-alone FTEP module or as one module in an automated multi-module cell processing system.
Figure 10B:
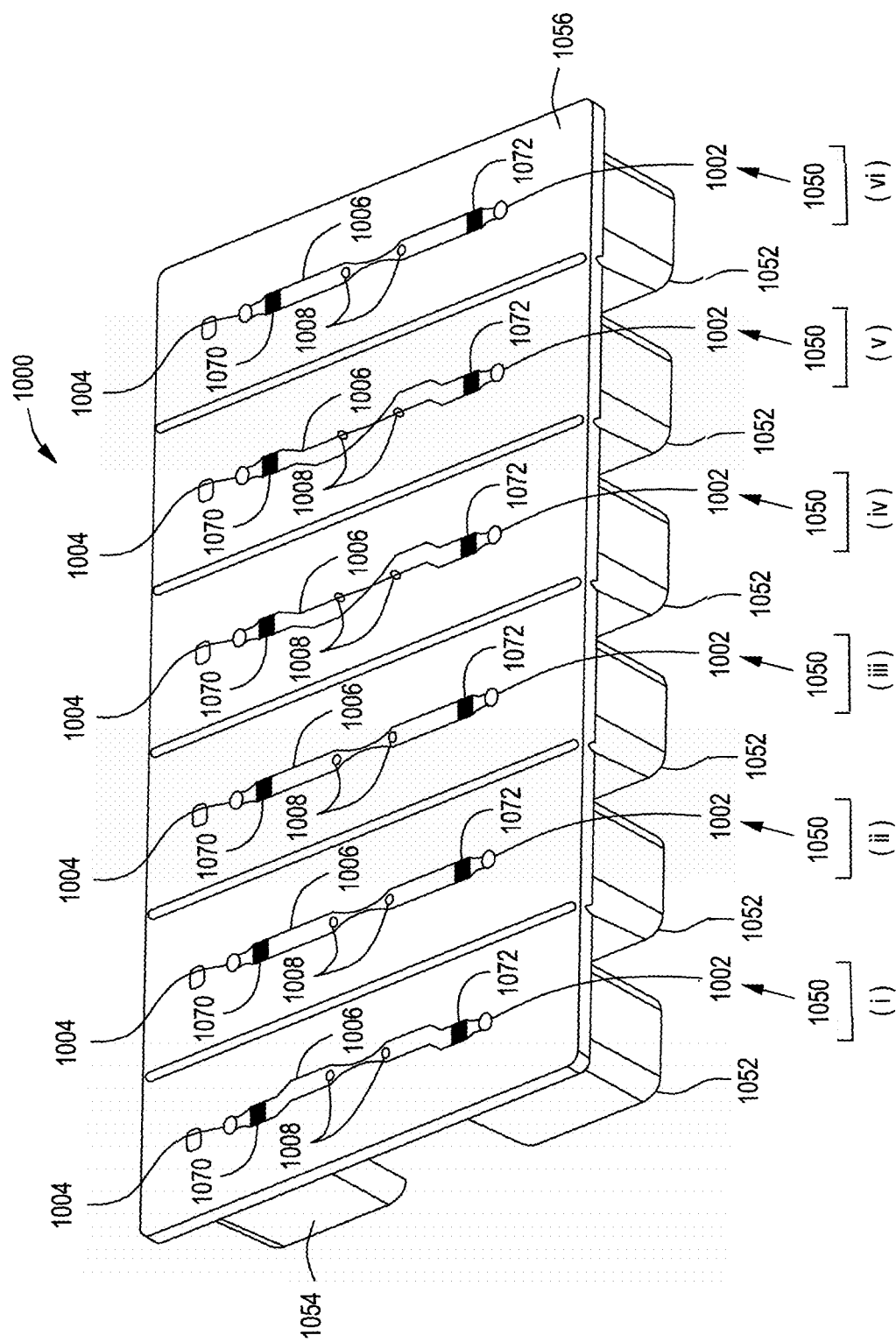
Figure 10C:
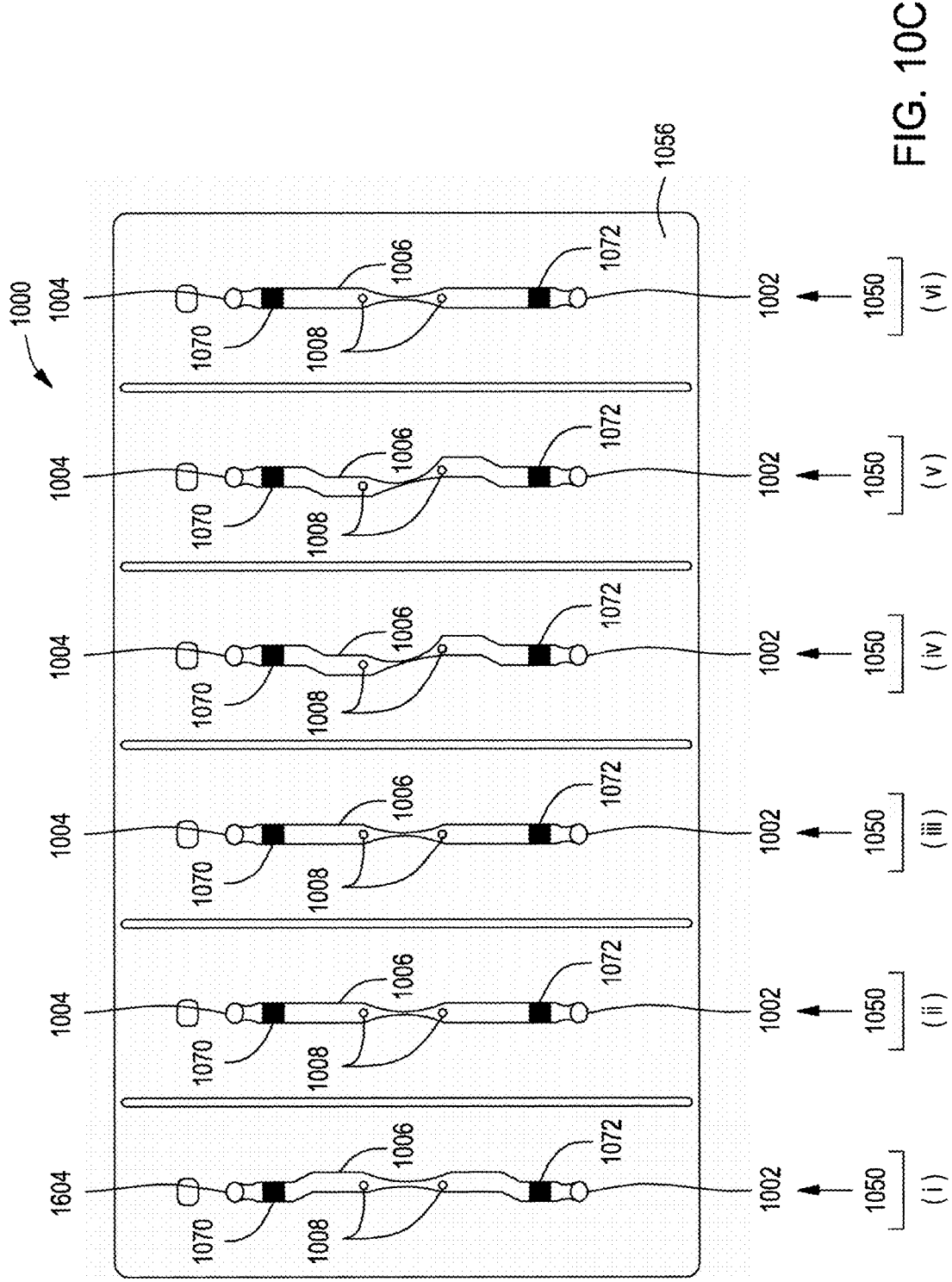
Figure 11E:
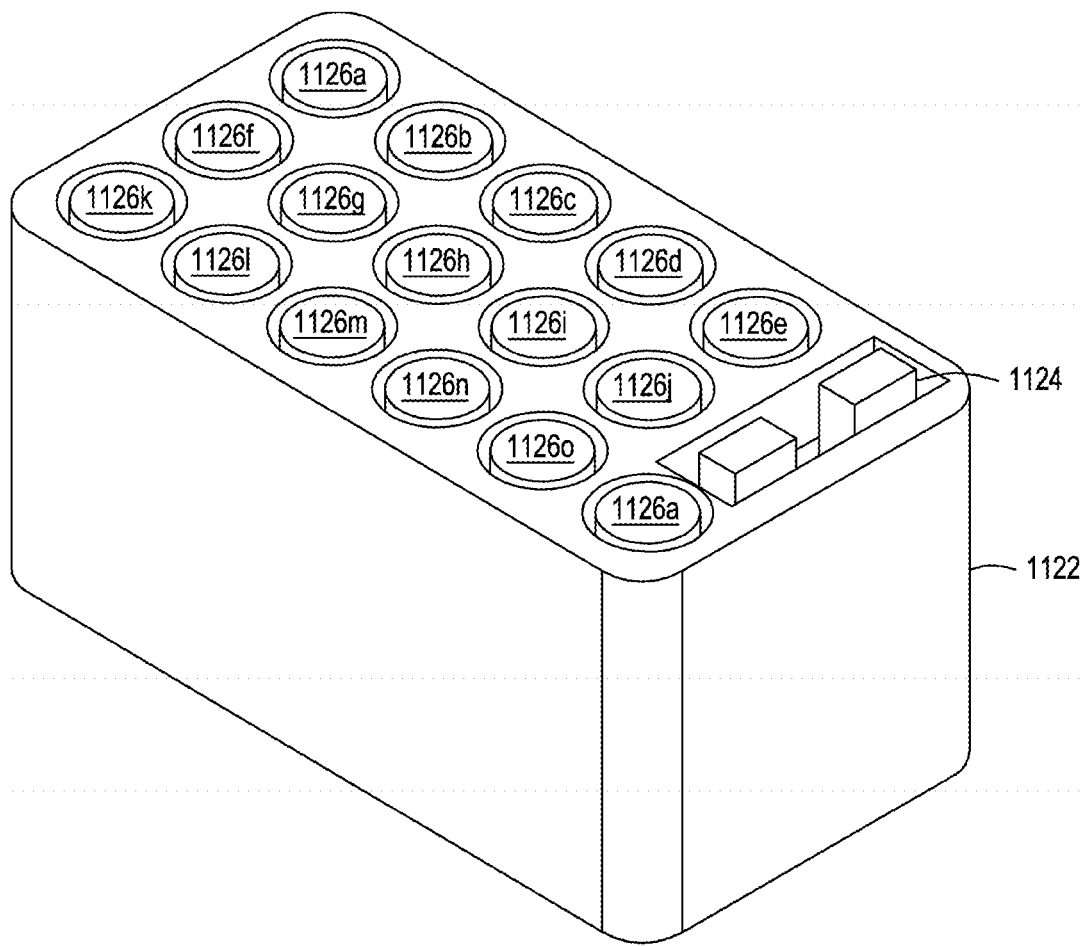

The reagent cartridges for use in the automated instruments (e.g., cartridge 1122 of FIG. 11E), in some embodiments, include one or more FTEP devices (e.g., electroporation module 1124 of FIG. 11E). FIGS. 10A through 10C are top perspective, bottom perspective, and bottom views, respectively, of six co-joined FTEP devices 1050 that may be part of, e.g., reagent cartridge 1122 in FIG. 11E infra (i.e., serve as FTEP 1124 in reagent cartridge 1122). FIG. 10A depicts six FTEP units 1050 (i.e., (i), (ii), (iii), (iv), (v), and (vi)) arranged on a single, integrally-formed injection molded cyclic olefin copolymer (COC) substrate 1056. The channels 1006 shown in FIG. 10B are sealed with a COC film having a thickness of 50 microns to 1 mm (not shown). The COC film may be thermally bonded to the base of the assembly 1000 (the surface most prominently displayed in FIG. 10B). In FIGS. 10B and 10C, the co-joined FTEP devices have different channel architectures and electrode placements that may be advantageous in various applications. For instance, the curved channels of devices (i), (iv) and (v) take advantage of inertia to direct the cells in the fluid away from the electrodes. The electrodes may be positioned off center in the channel to further enhance cells flow and reduce the potential for damage to the cells. This may be particularly important for cells or materials that are particularly sensitive to electrolytic effects or local changes in pH proximate the electrodes. The electrodes may be at least partially embedded into the channel walls, as shown in embodiments (iii) and (iv), so as to further reduce these effects.

Each of the six FTEP units 1050 have wells or reservoirs 1052 that define cell sample inlets and wells 1054 that define cell sample outlets. FIG. 10B is a bottom perspective view of the six co-joined FTEP devices 1050 of FIG. 15A also depicting six FTEP units 1050 (i.e., (i)-(vi)) arranged on a single substrate 1056. Six inlet wells 1052 can be seen, one for each flow-through electroporation unit 1050, and one outlet well 1054 can be seen. Also seen in FIG. 10B for each FTEP unit 1050 are an inlet 1002, an outlet 1004, a flow channel 1006, and two electrodes 1008 on either end of a narrowed region in flow channel 1006. Filters 1070 and 1072 are included in the channels to prevent clogging of the channel, particularly at narrowed region of the flow channel. FIG. 10C is a bottom view of the six co-joined FTEP devices 1050 of FIGS. 10A and 10B. Depicted in FIG. 10C are six FTEP units 1050 (i.e., (i)-(vi)) arranged on a single substrate 1056, where each FTEP unit 1050 comprises an inlet 1002, outlet 1004, flow channel 1006 and two electrodes 1508 on either end of a narrowed region in flow channel 1006 in each FTEP unit 1050. Once the six FTEP units 1050 are fabricated, they can be separated from one another (e.g., "snapped apart") upon the depicted score lines and used one at a time as seen in the cartridge depicted in FIG. 11E; alternatively, the FTEP units may be used in embodiments where two or more FTEP units 1050 are used in parallel.

Figure 10D:
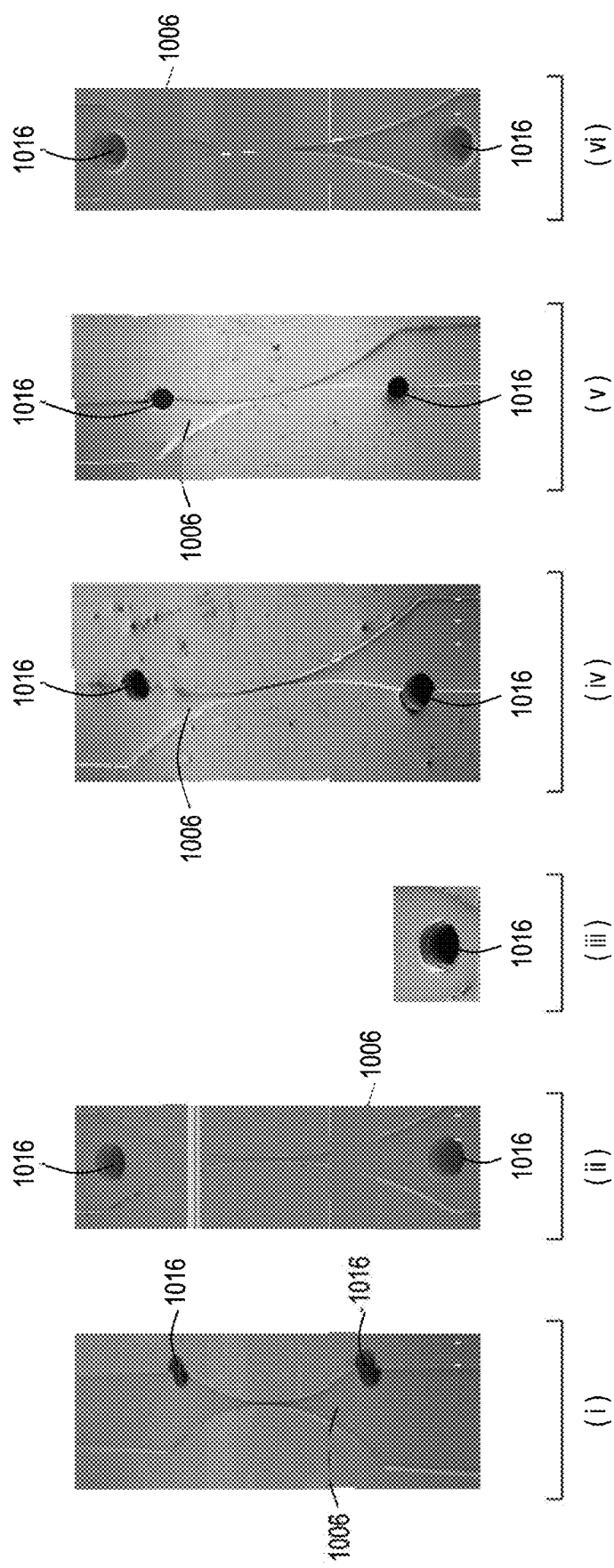
FIG. 10D shows scanning electromicrographs of the FTEP units depicted in FIG. 10C.

FIG. 10D shows scanning electromicrographs of the FTEP units depicted in FIG. 10C with the units (i), (ii), (iii), (iv), (v), and (vi) in FIG. 10D corresponding to units (i), (ii), (iii), (iv), (v), and (vi) in FIG. 10C. In FIG. 10D, for each unit both the electrode channels 1016 as well as the flow channel 1006 can be seen.

Figure 10E:
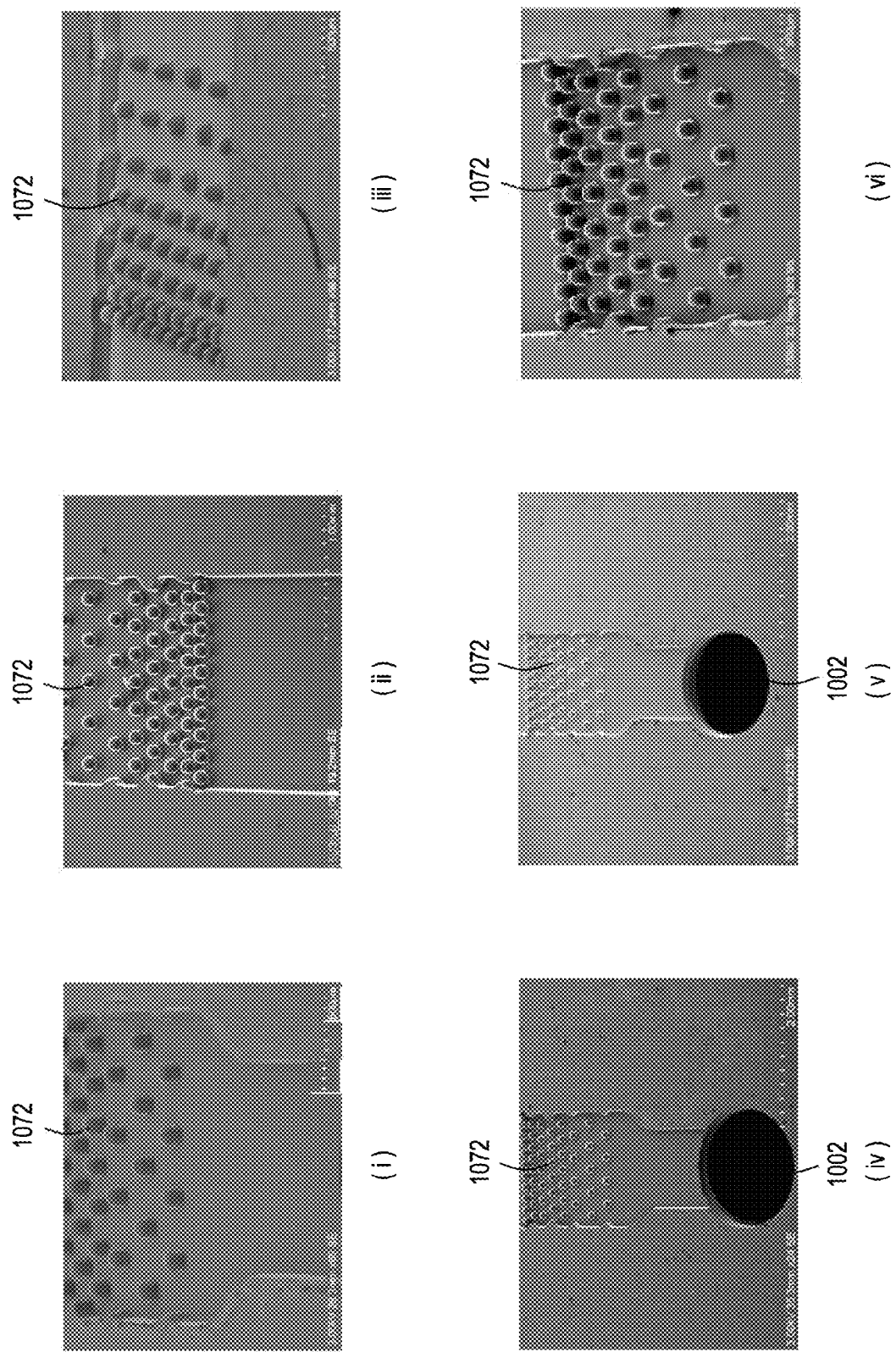
FIG. 10E shows scanning electromicrographs of filters 1070 and 1502 depicted as black bars in FIGS. 10B and 10C.

FIG. 10E shows scanning electromicrographs of the filters 1070 and 1072 depicted as black bars in FIGS. 10B and 10C. Note in this embodiment, the porosity of the filter 1072 varies from large pores (near the inlet 1002) to small pores toward the flow channel (not shown). In this embodiment, the channel optionally but not necessarily narrows. If a second filter is present, the second filter may also vary in porosity. In the case of a second filter between the second electrode and the outlet channel, the filter can vary from large pores (near the second electrode) to small pores toward the outlet channel. Scale information is shown in each micrograph.

In certain embodiments, the filter serves the purpose of filtering the fluid containing the cells and DNA before the fluid encounters the narrowed portion of the flow channel. The filter thus decreases the likelihood that cells or other matter do not clog the narrowed portion of the flow channel. Instead, if there is particulate matter that poses a threat to clogging the narrowed portion of the flow channel, the filter will catch the particulate matter leaving other pores through which the rest of the cell/DNA/fluid can move. The depicted construction (integral molding with the channel wall) is particularly advantageous because it reduces cost and complexity of the device while also reducing the risk that pieces of the filter itself may dislodge and clog the channel or otherwise interfere with device operation. Note that in this embodiment, the filter has a gradient pore size (from large pores proximate the inlet to smaller pores proximal the narrowed portion of the flow channel); however, in alternative embodiments the pores may be the same size or not gradient in size.

Further, in yet other embodiments the flow channel may not narrow. In these specific embodiments, the pores themselves can serve to provide such a narrowing function for enhancing electroporation, and the flow channel walls do not narrow or narrow minimally as the fluid flows through the channel. These embodiments can allow control of the rate of flow of cells through the device to optimize introduction of nucleic acid into various cell types.

Moreover, though the scanning electromicrographs in FIG. 10E shown the filter elements as rounded "pegs", it should be understood that the filter elements may be triangular-, square-, rectangular-, pentagonal-, hexagonal-, oval-, elliptical- or other faceted-shaped pegs.

Figure 10F:
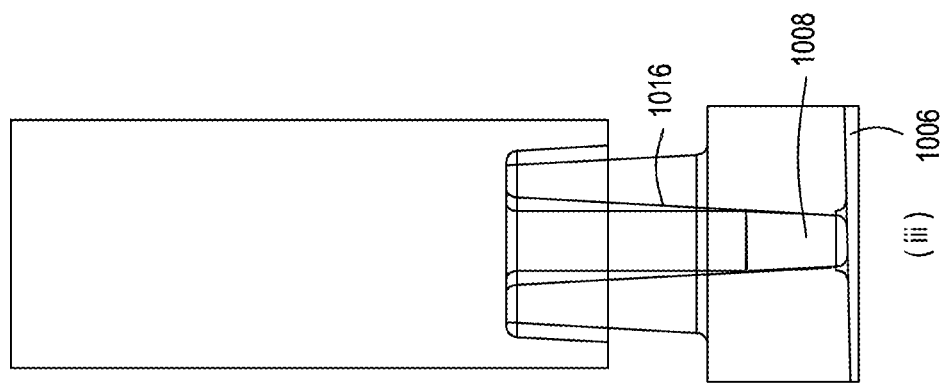
FIG. 10F depicts (i) the electrodes before insertion into the FTEP device; (ii) an electrode; and (iii) the electrode inserted into an electrode channel with the electrode and electrode channel adjacent to the flow channel.
Figure 10F:
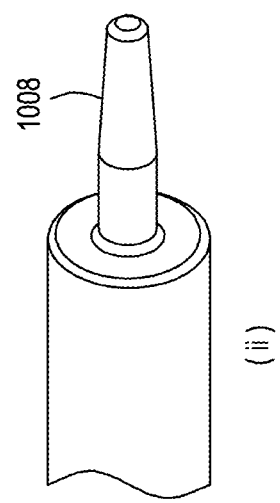
Figure 10F:
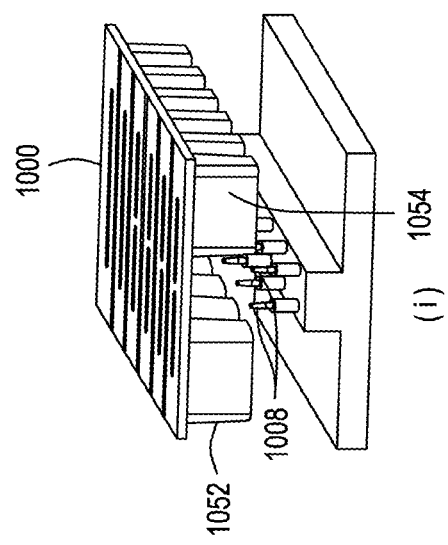

FIG. 10F depicts (i) the electrodes 1008 before insertion into the FTEP device 1000 (here, a six-unit FTEP device) having inlet reservoirs 1052 and outlet reservoirs 1054. In the preferred embodiment, the device 1000 is used in an orientation inverted relative to that shown in FIG. 10F (i). FIG. 10F (ii) depicts an electrode 1008 contained within and projecting from a sheath. FIG. 10F (iii) depicts the electrode 1008 inserted into an electrode channel 1016 with the electrode channel 1016 (and electrode 1008) adjacent to the flow channel 1006. In the embodiment shown in FIG. 10F (iii), the electrode is even with the walls of the flow channel; that is, the electrode is not in the path of the cells/DNA/fluid flowing through flow channel 1006, however, neither is the electrode recessed within the electrode channel 1016. Indeed, the electrode 1008 may be recessed within the electrode channel 1016, may be extend to the end of electrode channel 1016 and thus be even with the walls of flow channel 1006, or electrode 1008 may extend a minimal distance into flow channel 1006 so long as the electrode does not impede movement of the cells through the flow channel. The rounded or beveled edges of the aperture in the flow channel 1006 help prevent trapping air and reduce discontinuities in the electric field.

Figure 10G:
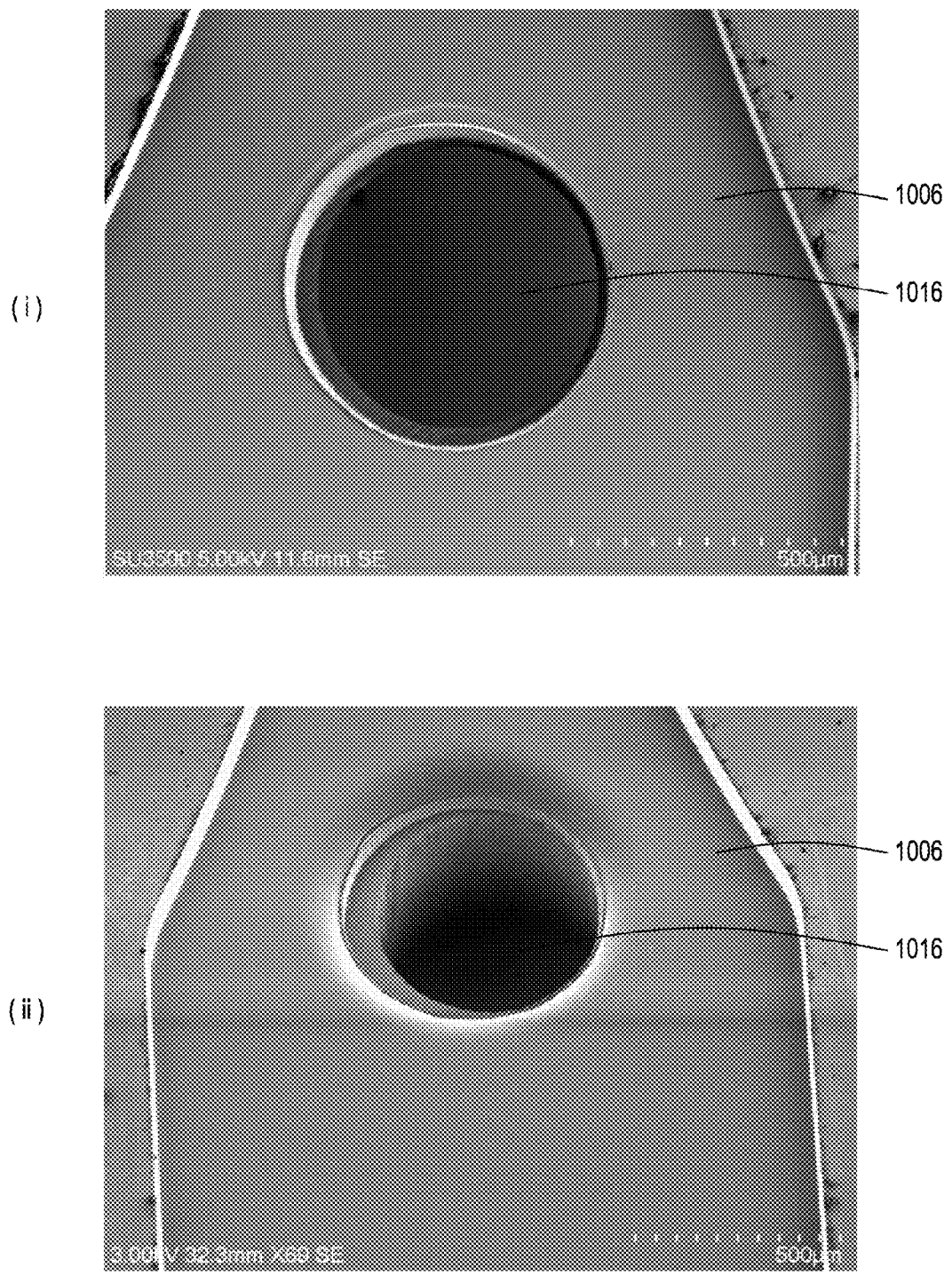
FIG. 10G shows two scanning electromicrographs of two different configurations of the aperture where the electrode channel meets the flow channel.

FIG. 10G presents two scanning electromicrographs of two different configurations of the aperture where electrode channel 1016 meets flow channel 1006. In FIG. 10G (i) (top), the edge of the junction of electrode channel 1016 and flow channel 1506 comprises a sharp edge. In contrast, in FIG. 10G (ii) (bottom), the edges of the junction of electrode channel 1016 and flow channel 1006 comprises a rounded edge. Both configurations were tested (data not shown), and it was found that the rounded-edge configuration decreases the likelihood that air will become trapped between flow channel 1006 and the electrode (not seen in this Figure) in electrode channel 1016. It can be seen that in this embodiment the inlet apertures have a rounded edge, the advantages of which include resistance to air trapping, promotion of laminar flow, and reduction of risk of cell damage. The rounded edges may have a radius of curvature of about 10, 20, 30, 40, 50, 60, 70, 80, 90, 100, 150, 200 or 250 microns. Indeed, the electrodes of the FTEP devices should be "wet"; that is, immersed in the fluid/cells/DNA.

After transformation, the cells are allowed to recover under conditions that promote the transformation and/or expression of the introduced nucleic acids in the cells. These temperatures and the duration of maintaining the temperatures can be determined by a preprogrammed set of parameters (e.g., identified within the processing script or in another memory space accessible by the processing system), or manually controlled by the user through interfacing with the processing system.

Once sufficient time has elapsed for the assembly reaction to take place, in some implementations, the nucleic acid assembly is transferred to a purification module. The processing system, for example, may monitor timing of the assembly reaction based upon one or more of the type of reaction, the type of materials, and user settings provided to the automated instrument. The robotic handling system 1708 of FIGS. 17A-17B, for example, may transfer the nucleic acid assembly to the purification module through a sipper or pipettor interface. In another example, the robotic handling system 1708 of FIGS. 17A-17B may transfer a vial containing the nucleic acid assembly from a chamber of the nucleic acid assembly module to a chamber of the de-salt/purification module.

In some implementations, the nucleic acid assembly is de-salted and eluted at the purification module. The purification module, for example, may remove unwanted components of the nucleic acid assembly mixture (e.g., salts, minerals, etc.). In some embodiments, the purification module concentrates the assembled nucleic acids into a smaller volume that the nucleic acid assembly volume. Examples of methods for exchanging liquid following nucleic acid assembly include magnetic beads (e.g., SPRI or Dynal (Dynabeads) by Invitrogen Corp. of Carlsbad, Calif.), silica beads, silica spin columns, glass beads, precipitation (e.g., using ethanol or isopropanol), alkaline lysis, osmotic purification, extraction with butanol, membrane-based separation techniques, filtration etc. For example, one or more micro-concentrators fitted with anisotropic, hydrophilic-generated cellulose membranes of varying porosities may be used. In another example, the de-salt/purification module may process a liquid sample including a nucleic acid and an ionic salt by contacting the mixture with an ion exchanger including an insoluble phosphate salt, removing the liquid, and eluting nucleic acid from the ion exchanger.

In an illustrative embodiment, the nucleic acid assembly may be combined with magnetic beads, such as SPRI beads, in a chamber of a purification module. The nucleic acid assembly may be incubated at a set temperature for sufficient time for the assembled nucleic acids to bind to the magnetic beads. After incubation, a magnet may be engaged proximate to the chamber so that the nucleic acid assembly can be washed and eluted. An illustrative example of this process is discussed in relation to the combination nucleic acid assembly and purification module of FIG. 3.

Once the nucleic acid assembly has been eluted, the nucleic acid assembly, in some implementations, is transferred to the transformation module. The robotic handling system 1708 of FIGS. 17A-17B, for example, may transfer the assembled nucleic acids to the transformation module through a sipper or pipettor interface to the FTEP as described above. For example, the de-salted assembled nucleic acids, during the transfer, may be combined with the electrocompetent cells from step 1408. In other embodiments, the transformation module may accept each of the electrocompetent cells and the nucleic acid assembly separately and enable the mixing (e.g., open one or more channels to combine the materials in a shared chamber).

The cells are transformed in the FTEP module. A buffer or medium may be transferred to the transformation module and added to the cells so that the cells may be suspended in a buffer or medium that is favorable for cell survival during electroporation. Prior to transferring the buffer or medium, machine-readable indicia may be scanned upon the vial or other container or reservoir situated in the position designated for the buffer or medium to confirm the contents of the vial, container, or reservoir. Further, the machine-readable indicia may indicate a type of buffer or medium provided to the instrument. The type of buffer or medium, in some embodiments, may cause the instrument to select a particular processing script (e.g., settings and activation of the transformation module appropriate for the particular buffer or medium). For bacterial cell electroporation, low conductance mediums, such as water or glycerol solutions, may be used to reduce the heat production by transient high current. For yeast cells a sorbitol solution may be used. For mammalian cell electroporation, cells may be suspended in a highly conductive medium or buffer, such as MEM, DMEM, IMDM, RPMI, Hanks', PBS, HBSS, HeBS and Ringer's solution. In a particular example, the robotic handling system may transfer a buffer solution to FTEP module from one of the cartridges. As described in relation to FIGS. 4A-4I, 5A-5H, 6, 7A-7E, 8A-8U, and 9A-9C, the FTEP device may be a disposable FTEP device and/or the FTEP device may be provided with the cartridge (FTEP device 1124 of cartridge 1122 in FIG. 11E).

Once transformed, the cells are transferred to a second growth/recovery module. The robotic handling system 1708 of FIGS. 17A-17B, for example, may transfer the transformed cells to the second growth module through a sipper or pipettor interface. In another example, the robotic handling system 108 of 1A-1B or 1708 of FIGS. 17A-17B may transfer a vial containing the transformed cells from a chamber of the transformation module to a chamber of the second growth module.

The second growth module, in some embodiments, acts as a recovery module, allowing the cells to recover from the transformation process. In other embodiments, the cells may be provided to a separate recovery module prior to being transported to the second growth module. During recovery, the second growth module allows the transformed cells to uptake and, in certain aspects, integrate the introduced nucleic acids into the genome of the cell. The second growth module may be configured to incubate the cells at any user-defined temperature optimal for cell growth, preferably 25°, 30°, or 37° C.

In some embodiments, the second growth module behaves as a selection module, selecting the transformed cells based on an antibiotic or other reagent. In the example of an antibiotic selection agent, the antibiotic may be added to the second growth module to enact selection. Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, or chloramphenicol-resistance gene. The robotic handling system 1708 of FIGS. 17A-17B, for example, may transfer the antibiotic to the second growth module through a sipper or pipettor interface. In some embodiments, removing dead cell background is aided using lytic enhancers such as detergents, osmotic stress by hyponic wash, temperature, enzymes, proteases, bacteriophage, reducing agents, or chaotropes. The processing system 1410 of FIG. 14, for example, may alter environmental variables, such as temperature, to induce selection, while the robotic handling system 1708 of FIGS. 17A-17B may deliver additional materials (e.g., detergents, enzymes, reducing agents, etc.) to aid in selection. In other embodiments, cell removal and/or media exchange by filtration is used to reduce dead cell background.

Some implementations may include the storage module 1714 of FIGS. 17A-17B. The robotic handling system 1708 of FIGS. 17A-17B, for example, may transfer the cells to the storage module 114 through a sipper or pipettor interface. In another example, the robotic handling system 1708 of FIGS. 17A-17B may transfer a vial containing the cells from a chamber of the second growth module to a vial or tube within the storage unit.

In some implementations, the method can be timed to introduce materials and/or complete the transformation cycle or growth cycle in coordination with a user's schedule. For example, the automated instrument may provide the user the ability to schedule completion of one or more cell processing cycles such that the method is enacted with a goal of completion at the user's preferred time. The time scheduling, for example, may be set through a user interface, such as the user interface 1416 of FIG. 14. For illustration only, a user may set completion of a first cycle to 4:00 PM so that the user can supply additional cartridges of materials to the automated instrument to enable overnight processing of another round of cell processing. Thus a user may time the programs so that two or more cycles may be programmed in a specific time period, e.g., a 24-hour period.

In some implementations, throughout the method, the automated instrument may alert the user to its current status. For example, the user interface 1416 of FIG. 14 may present a graphical indication of the present stage of processing. In a particular example, a front face of the automated multi-module call processing instrument may be overlaid with a user interface (e.g., touch screen) that presents an animated graphic depicting present status of the cell processing. The user interface may further present any user and/or default settings associated with the current processing stage (e.g., temperature setting, time setting, etc.). In certain implementations, the status may be communicated to a user via wireless communications controller.

Although illustrated as a particular series of operations, in other embodiments, more or fewer steps may be included in the method. For example, in some embodiments, the contents of reservoirs, cartridges, and/or vials may be screened to confirm appropriate materials are available to proceed with processing. For example, in some embodiments, one or more imaging sensors (e.g., barcode scanners, cameras, etc.) may confirm contents at various locations within the housing of the automated instrument. In one example, multiple imaging sensors may be disposed within the housing of the automated instrument, each imaging sensor configured to detect one or more materials (e.g., machine-readable indicia such as barcodes or QR codes, shapes/sizes of materials, etc.). In another example, at least one imaging sensor may be moved by the robotic handling system to multiple locations to detect one or more materials. In further embodiments, one or more weight sensors may detect presence or absence of disposable or replaceable materials. In an illustrative example, the transfer tip supply holder may include a weight sensor to detect whether or not tips have been loaded into the region. In another illustrative example, an optical sensor may detect that a level of liquid waste has reached a threshold level, requiring disposal prior to continuation of cell processing or addition of liquid if the minimum level has not been reached to proceed. Requests for additional materials, removal of waste supplies, or other user interventions (e.g., manual cleaning of one or more elements, etc.), in some implementations, are presented on a graphical user interface of the automated instrument. The automated instrument, in some implementations, contacts the user with requests for new materials or other manual interventions, for example through a software app, email, or text message.

Workflows for Cell Processing in an Automated Instrument

The automated instrument is designed to perform a variety of cell processing workflows using the same modules. For example, source materials, in individual containers or in cartridge form, may differ and the corresponding instructions (e.g., software script) may be selected accordingly, using the same basic instrumentation and robotic handling system; that is, the instrument can be configured to perform a number of different workflows for processing cell samples and different types of cell samples.

Figure 15A:
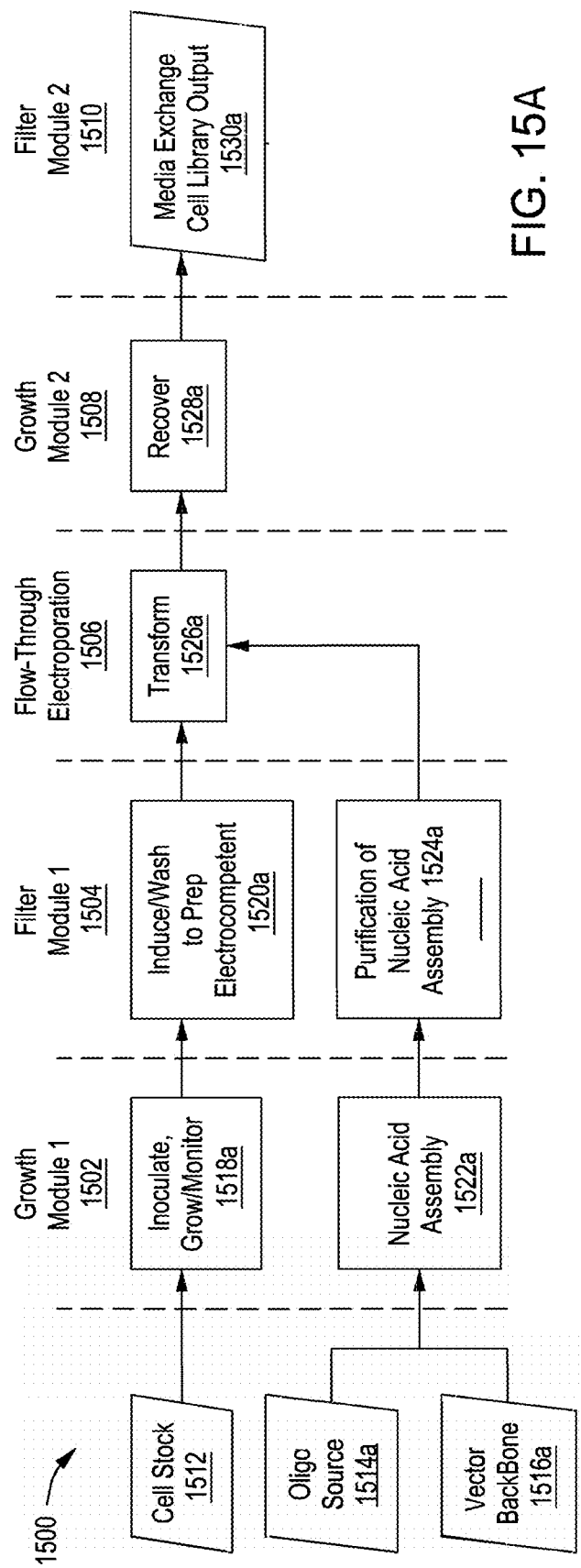
FIG. 15A is a flow diagram of a first example workflow for automated introduction of nucleic acids in an automated instrument.
Figure 15B:
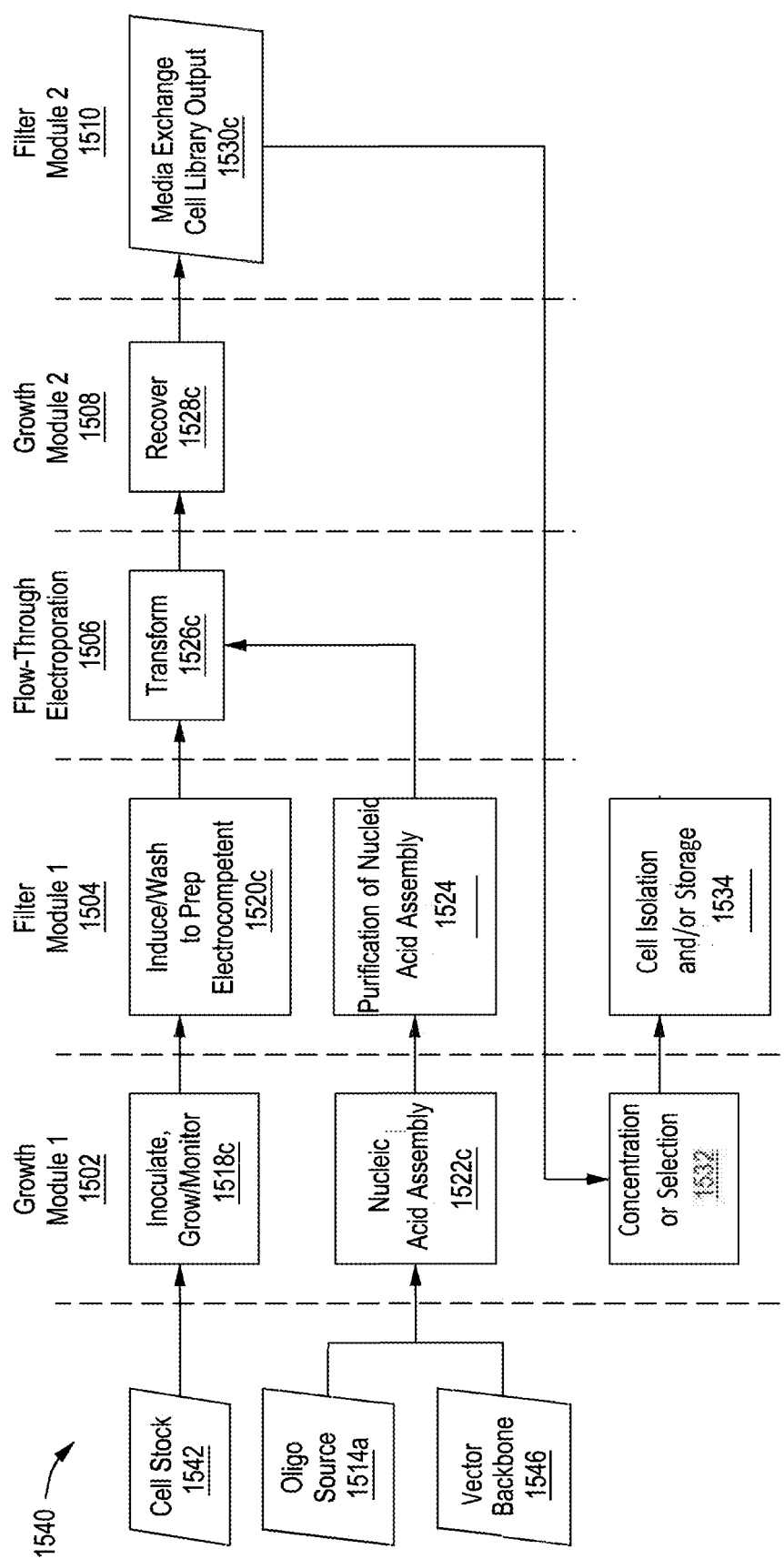
FIG. 15B is a flow diagram of a first example workflow for automated introduction of nucleic acids in an instrument.
Figure 15C:
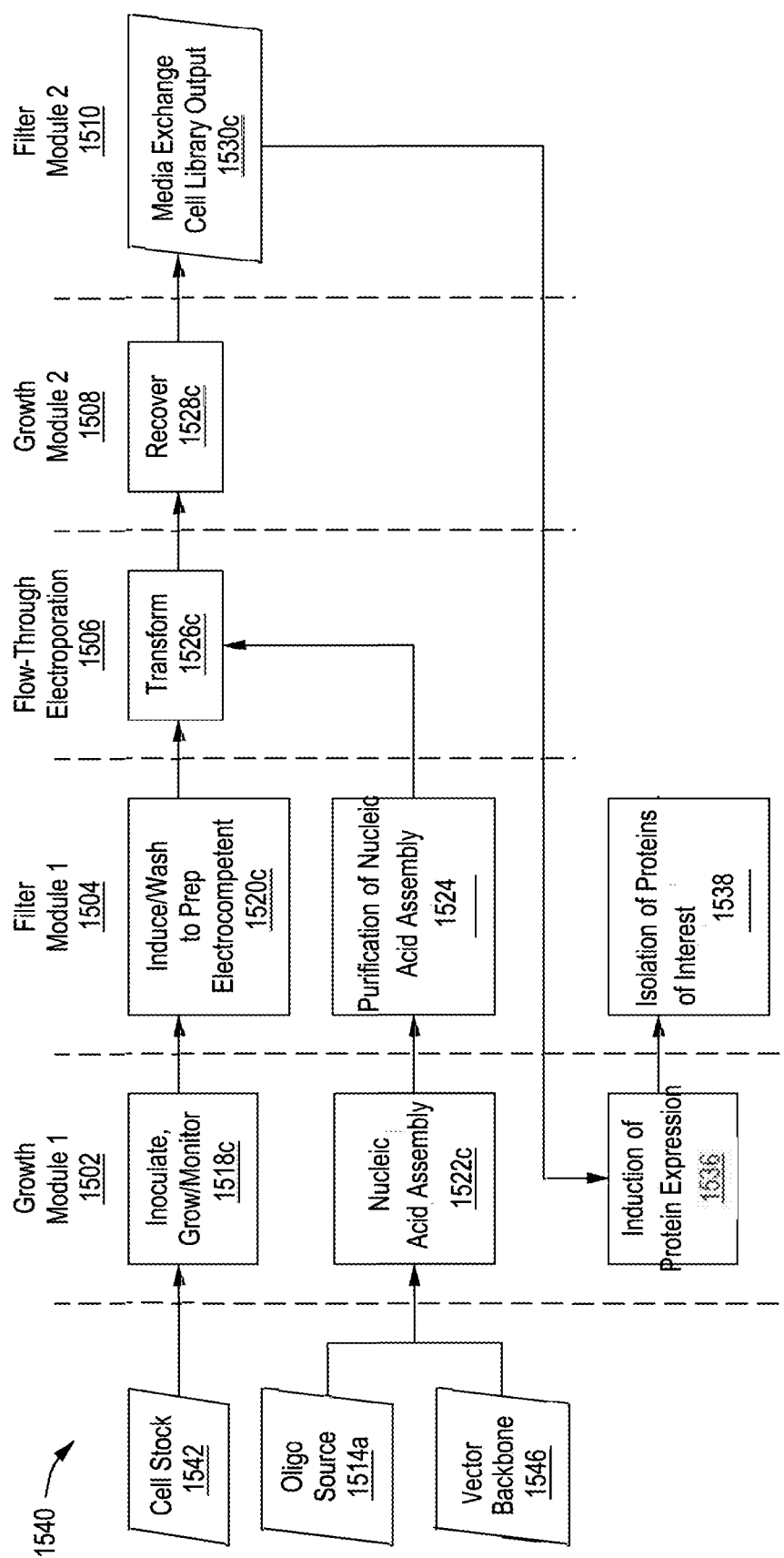
FIG. 15C is a flow diagram of a second example workflow for automated introduction of nucleic acids with additional protein expression and isolation.

FIGS. 15A through 15C illustrate example workflows that may be performed using an exemplary automated instrument including two cell growth modules 1502, 1508, two filtration modules 1504 and 1510, and a flow-through electroporation module 1506. Although described as separate growth modules 1502, 1508 and filtration modules 1504, 1510, each may instead be designed as a dual or integrated module. For example, a dual growth module, including growth modules 1502 and 1508, may include dual rotating growth vials sharing some circuitry, controls, and a power source and disposed in a same housing. Similarly, a dual filtration module may include filtration modules 1504 and 1510, including two separate filters and liquid supply tubes but sharing circuitry, controls, a power source, and a housing. The modules 1502, 1504, 1506, 1508, and 1510, for example, may be part of the instrument.

Turning to FIG. 15A, a flow diagram illustrates a first workflow 1500 involving processing steps resulting in introduction of nucleic acids to a cell stock 1512. This flow chart optionally uses a cartridge of source materials. For example, a cartridge may include an oligo source 1514a and a vector backbone 1516a. The cell stock 1512, in some embodiments, is included with the oligo or reagents. The cell stock 1512 may be supplied within a kit including the cartridge. Alternatively, a user may add a container (e.g., vial or tube) of the cell stock 1512 to a cartridge.

The workflow 1500, in some embodiments, is performed based upon a script executed by a processing system of the automated instrument, such as the processing system 1410 of FIG. 14. The script, in a first example, may be accessed via a machine-readable marker or tag added to the first cartridge. In some embodiments, each processing stage is performed using a separate script. For example, each cartridge may include an indication of a script or a script itself for processing the contents of the cartridge.

In some implementations, the first stage begins with introducing the cell stock 1512 into the first growth module 1502 for inoculation, growth, and monitoring (1518a). In one example, a robotic handling system adds a vial of the cell stock 1512 to medium contained in the rotating growth vial of the first growth module 1502. In another example, the robotic handling system pipettes cell stock 1512 from the first cartridge and adds the cell stock 1012 to the medium contained in the rotating growth vial. The cells may have been maintained at a temperature of 4° C. at this point. In a particular example, 20 ml of cell stock may be grown within a rotating growth vial of the first growth module 1002 at a temperature of 30° C. to an OD of 0.50. The cell stock 1012 added to the first growth module 1502 may be monitored over time until 0.50 OD is sensed via automated monitoring of the growth vial. Monitoring may be periodic or continuous. This may take, for example, around 900 minutes (estimated), although the exact time depends upon detection of the desired OD.

In some implementations, after growing the cells to the desired OD, an inducer is added to the first growth module 1502 for inducing the cells. In a particular example, 100 µl of inducer may be added, and the growth module 1502 may bring the temperature of the mixture up to 42° C. and hold for 15 minutes.

The cell stock 1512, after growth and induction, is transferred to the first filtration module 1504, in some implementations, for rendering the cells electrocompetent (1520a) and to reduce the volume of the cells for transformation. In one example, a robotic handling system moves the vial of the cell stock 1512 from the rotating growth vial of the first growth module 1502 to a vial holder of the first filtration module 1504. In another example, the robotic handling system pipettes cell stock 1512 from the rotating growth vial of the first growth module 1502 and delivers it to the first filtration module 1504. For example, the disposable pipetting tip used to transfer the cell stock 1512 to the first growth module 1502 may be used to transfer the cell stock 1512 from the first growth module 1502 to the first filtration module 1504. In some embodiments, prior to transferring the cell stock 1512 from the first growth module 1502 to the first filtration module 1504, the first growth module 1502 is cooled to 4° C. so that the cell stock 1512 is similarly reduced to this temperature. In a particular example, the temperature of the first growth module 1502 may be reduced to about 4° C. over the span of about 8 minutes, and the growth module 1502 may hold the temperature at 4° C. for about 15 minutes to ensure reduction in temperature of the cell stock 1512.

Prior to transferring the cell stock, in some implementations, a filter of the first filtration module 1504 is pre-washed using a wash solution. The wash solution, for example, may be supplied in a wash cartridge, such as the cartridge 1126 described in relation to FIG. 11C.

The first filtration module 1504, for example, may be part of a dual filtration module such as the filtration module 1250 described in relation to FIGS. 12B and 12C. In a particular example, the first filtration module 1504 may be maintained at 4° C. during the washing and eluting process while transferring cell materials between an elution vial and the first filtration module 1504.

In some implementations, upon rendering the cells electrocompetent at the filtration module 1504, the cell stock 1512 is transferred to a transformation module 1506 (e.g., flow-through electroporation module) for transformation. In one example, a robotic handling system moves the vial of the cell stock 1512 from the vial holder of the first filtration module 1504 to a reservoir of the flow-through electroporation module 1506. In another example, the robotic handling system pipettes cell stock 1512 from the first filtration module 1502 or a temporary reservoir and delivers it to the first filtration module 1504. In a particular example, 400 µl of the concentrated cell stock 1512 from the first filtration module 1504 is transferred to a mixing reservoir prior to transfer to the transformation module 1506. For example, the cell stock 1512 may be transferred to a reservoir in a cartridge for mixing with the assembled nucleic acids, then transferred by the robotic handling system using a pipette tip. In a particular example, the transformation module is maintained at 4° C.

While the cells are growing and/or rendered electrocompetent, in some implementations, a first oligo source 1514a and the vector backbone 1516a are assembled using a nucleic acid assembly process to create assembled nucleic acids, e.g., using a thermal cycler and ligation process or in an isothermal reaction within a nucleic acid assembly module (1522a). The assembled nucleic acids may be created at some point during the first processing steps 1518a, 1520a of the first stage of the workflow 1500. Alternatively, assembled nucleic acids may be created in advance of beginning the first processing step 1518.

In some embodiments, the nucleic acids are assembled using a nucleic acid assembly module of the automated instrument. For example, the robotic handling system may add the first oligo source 1514a and a vector backbone 1516a from a vessel in the reagent cartridge in the automated instrument to a nucleic acid assembly module (not illustrated), such as the nucleic acid assembly module 1710g described in relation to FIG. 17B. The nucleic acid assembly mix, for example, may include in a particular example 50 µl Gibson Assembly® Master Mix, 25 µl vector backbone 1516a, and 25 µl oligo 1514a. The nucleic acid assembly module may be held at room temperature or at another desired temperature.

In other embodiments, the nucleic acids are assembled externally to the instrument and added as a functioning source material. For example, a vial or tube of assembled nucleic acids may be added to a reagent cartridge prior to activating the first step 1518a of inoculation, growth and cell processing. In a particular example, 100 µl of assembled nucleic acids are provided.

In other embodiments, the nucleic acids are introduced to the cells in components, and the machinery of the transformed cells will perform the assembly within the cell, e.g., using gap repair mechanisms in yeast cells.

In some implementations, the assembled nucleic acids are purified (1524a). The assembled nucleic acids, for example, may be transferred by the robotic handling system from the nucleic acid assembly module to a purification module (not shown). In other embodiments, the nucleic acid assembly module may include purification features (e.g., a combination nucleic acid assembly and purification module). In further embodiments, the assembled or separate nucleic acids are purified externally to the instrument and added as a functional source material. For example, a vial or tube of purified assembled nucleic acids may be added to a reagent cartridge with the cell stock 1012 prior to activating the first step 1518a of cell processing.

In a particular example, 100 µl of assembled nucleic acids in nucleic acid assembly mix are assembled and subsequently purified. In some embodiments, magnetic beads are added to the nucleic acid assembly module, for example 180 µl of magnetic beads in a liquid suspension may be added to the nucleic acid assembly module by the robotic handling system. A magnet functionally coupled to the nucleic acid assembly module may be activated and the sample washed in 200 µl ethanol (e.g., the robotic handling system may transfer ethanol to the nucleic acid assembly module). Liquid waste from this operation, in some embodiments, is transferred to a waste receptacle of the cartridge (e.g., by the robotic handling system using a same pipette tip as used in transferring the ethanol). At this point, the de-salted assembled nucleic acids may be transferred to a holding container, such as a reservoir of the cartridge. The desalted assembled nucleic acids may be held, for example at a temperature of 4° C. until cells are ready for transformation. In a particular example, 100 µl of the assembled nucleic acids may be added to the 400 µl of the concentrated cell stock 1512 in the mixing reservoir prior to transfer to the transformation module 1506. In some embodiments, the purification process may take about 16 minutes.

In some implementations, the assembled nucleic acids and cell stock 1512 are added to the flow-through electroporation module 1506 and the cell stock 1512 is transformed (1526a). The robotic handling system, for example, may transfer the mixture of the cell stock 1512 and assembled nucleic acids to the flow-through electroporation module 1506 from a mixing reservoir, e.g., using a pipette tip or through transferring a vial or tube. In some embodiments, a built-in flow-through electroporation module such as the flow-through electroporation modules depicted in FIGS. 4A-4I, 5A-5H, 6, 8A-8U, and 9A-9C is used to transform the cell stock 1512. In other embodiments, a cartridge-based electroporation module such as shown in FIGS. 10A-10C and 10E is used to transform the cell stock 1512. The electroporation module 1506, for example, may be held at a temperature of 4° C. The electroporation process, in an illustrative example, may take about four minutes.

The transformed cell stock 1512 in some implementations is transferred to the second growth module 1508 for recovery (1528a). In a particular example, transformed cells undergo a recovery process in the second growth module 1508 at a temperature of 30° C. The transformed cells, for example, may be maintained in the second growth module 1508 for a predetermined period of time, e.g., about an hour for recovery.

In some implementations, a selective medium is transferred to the second growth vial (not illustrated), and the cells are left to incubate for a further period of time in a selection process. In an illustrative example, an antibiotic may be transferred to the second growth vial, and the cells may incubate for an additional two hours at a temperature of 30° C. to select for cells that have received the nucleic acids.

In some implementations, in preparation for further processing, the transformed cells are transferred to the second filtration module 1510 for media exchange and filtering (1530*a*). Prior to transferring the transformed cell stock, in some implementations, a filter of the second filtration module 1504 is pre-washed using a wash solution. The wash solution, for example, may be supplied in a wash cartridge, such as the cartridge 1126 described in relation to FIG. 11C. The second filtration module 1510, for example, may be fluidly connected to the wash solution of the wash cartridge, as described in relation to FIG. 12A.

The second filtration module 1510, for example, may be part of a dual filtration module such as the filtration module 1250 described in relation to FIGS. 12B and 12C. In a particular example, the second filtration module 1510 may be maintained at a predetermined temperature (e.g., 4° C.) during the washing and eluting process while transferring cell materials between an elution vial and the second filtration module 1510. The output of this filtration process, in a particular example, is deposited in a vial or tube to await further processing, e.g., transfer to a transformation module. The vial or tube may be maintained in a storage module at a temperature of 4° C.

In other implementations, turning to FIG. 15B, a workflow 1540 involves the same modules 1502, 1504, 1506, 1508, and 1510 as well as the same processing steps 1518, 1520, 1522, 1524, 1526, 1528, and 1530 for the first stage of process. However, unlike the workflow 1500 of FIG. 15A, the workflow 1540 of FIG. 15B includes the additional steps of induction and/or concentration of cells of interest (i.e. transformed cells) and storage of the cells once selected and/or concentrated. For example, the cells may undergo selection in a cell selection/concentration module 1532, followed by storage of the selected/concentrated cells in a storage module 1534. In certain implementations, the cell selection/concentration module and storage module are combined into a single, integrated module.

As with the workflow 1500, in some embodiments, the workflow 1540 is performed based upon a script executed by a processing system of the automated instrument, such as the processing system 1410 of FIG. 14. The script, in a first example, may be accessed via a machine-readable marker or tag added to the first cartridge. In some embodiments, each processing stage is performed using a separate script. For example, each cartridge may include an indication of a script or a script itself for processing the contents of the cartridge. The automated instrument in this implementation includes a n oligo source, the cells are inoculated, grown, and monitored in the first growth module 1502 (1518*d*). In a particular example, an aliquot of the cell stock 1542 may be transferred to a rotating growth vial containing, e.g., 20 mL of growth medium at a temperature of 30° C. to an OD of 0.50. The cell stock 1542 added to the first growth module 1502 may be monitored over time until 0.50 OD is sensed via the automated monitoring. Monitoring may be periodic or continuous. This may take, for example, around 900 minutes (estimated), although the exact time depends upon detection of the desired OD.

In some implementations, after growing to the desired OD, an inducer is added to the first growth module 1502 for inducing the cells. In a particular example, 100 µl of inducer may be added, and the growth module 1502 may bring the temperature of the mixture up to 42° C. and hold for 15 minutes.

The cell stock 1542, after growth and induction, is transferred to the first filtration module 1504, in some implementations, for rendering the cells electrocompetent (1520*d*). In one example, a robotic handling system moves the vial of the cell stock 1542 from the rotating growth vial of the first growth module 1502 to a vial holder of the first filtration module 1504. In another example, the robotic handling system pipettes cell stock 1542 from the rotating growth vial of the first growth module 1502 and delivers it to the first filtration module 1504. For example, the disposable pipetting tip used to transfer the cell stock 1542 to the first growth module 1502 may be used to transfer the cell stock 1542 from the first growth module 1502 to the first filtration module 1504. In some embodiments, prior to transferring the cell stock 1542 from the first growth module 1502 to the first filtration module 1504, the first growth module 1502 is cooled to 4° C. so that the cell stock 1542 is similarly reduced to this temperature. In a particular example, the temperature of the first growth module 1502 may be reduced to about 4° C. over the span of about 8 minutes, and the growth module 1502 may hold the temperature at 4° C. for about 15 minutes to ensure reduction in temperature of the cell stock 1512.

Prior to transferring the cell stock 1542 to the filtration module, in some implementations a filter of the first filtration module 1504 is pre-washed using a wash solution. The wash solution, for example, may be supplied in a wash cartridge, such as the cartridge 1126 described in relation to FIG. 11C. The first filtration module 1504, for example, may be fluidly connected to the wash solution of the wash cartridge.

The first filtration module 1504, for example, may be part of a dual filtration module such as the filtration module 1250 described in relation to FIGS. 12B and 12C. In a particular example, the first filtration module 1504 may be maintained at a predetermined temperature (e.g., 4° C.) during the washing and eluting process while transferring cell materials between an elution vial and the first filtration module 1504.

In some implementations, upon rendering the cells electrocompetent at the filtration module 1504 (1520*d*), the cell stock 1542 is transferred to a transformation module 1506 (e.g., FTEP module) for transformation. In one example, a robotic handling system moves the vial of the cell stock 1542 from the vial holder of the first filtration module 1504 to a reservoir of the flow-through electroporation module 1506. In another example, the robotic handling system pipettes cell stock 1542 from the first filtration module 1502 or a temporary reservoir and delivers it to the first filtration module 1504. In a particular example, 400 µl of the concentrated cell stock 1542 from the first filtration module 1504 is transferred to a mixing reservoir prior to transfer to the transformation module 1506. For example, the cell stock 1542 may be transferred to a reservoir in a cartridge, then mixed and transferred by the robotic handling system using a pipette tip. In a particular example, the transformation module 1506 is maintained at a predetermined temperature, e.g., 4° C. The cell stock 1542 may be transformed, in an illustrative example, in about four minutes.

The transformed cell stock 1542, in some implementations, is transferred to the second growth module 1508 for recovery (1528*d*). In a particular example, 20 ml of transformed cells undergo a recovery process in the second growth module 1508 at a temperature of 30° C. The transformed cells, for example, may be maintained in the second growth module 1508 for about an hour for recovery.

After recovery, the cells may be ready for further processing (e.g., induction of protein expression or cell sorting) or for storage to be used in further research outside the automated cell processing instrument. For example, a portion of the cells may be transferred to a storage module as cell library output, while another portion of the cells may be prepared for a protein expression and isolation.

In some implementations, in preparation for further processing or for cell concentration, the transformed cells are transferred to the second filtration module 1510 for media exchange and filtering (1530*d*) containing glycerol for rendering the cells electrocompetent. Prior to transferring the transformed cell stock, in some implementations, a filter of the second filtration module 1504 is pre-washed using a wash solution. The wash solution, for example, may be supplied in a wash cartridge. The second filtration module 1510, for example, may be fluidly connected to the wash solution of the wash cartridge, as described in relation to FIG. 12A.

The second filtration module 1510, for example, may be part of a dual filtration module such as the filtration module 1250 described in relation to FIGS. 12B and 12C. In a particular example, the second filtration module 1510 may be maintained at 4° C. during the washing and eluting process while transferring cell materials between an elution vial and the second filtration module 1510. The output of this filtration process, in a particular example, are electrocompetent cells deposited in a vial or tube to await further processing. The vial or tube may be maintained in a storage module at a temperature of 4° C.

Turning to FIG. 15C, a flow diagram illustrates another workflow 1560 involving an induction of protein expression from the introduced oligos and isolation of the produced proteins. The workflow 1560, in some embodiments, is performed based upon a script executed by a processing system of the automated instrument, such as the processing system 1410 of FIG. 14. The script, in a first example, may be accessed via a machine-readable marker or tag added to the first cartridge. In some embodiments, each processing stage is performed using a separate script. For example, each cartridge may include an indication of a script or a script itself for processing the contents of the cartridge.

In some implementations, the first stage begins with introducing the cell stock 1562 into the first growth module 1502 for inoculation, growth, and monitoring (1518*e*). In one example, a robotic handling system adds a vial of the cell stock 1562 to a rotating growth vial of the first growth module 1502. In another example, the robotic handling system pipettes cell stock 1562 from the first cartridge and adds the cell stock 1562 to the rotating growth vial. The cells may have been maintained at a temperature of 4° C. at this point. In a particular example, 20 ml of cell stock may be grown within a rotating growth vial of the first growth module 1502 at a temperature of 30° C. to an OD of 0.75. The cell stock 1512 added to the first growth module 1502 may be automatically monitored over time within the growth module 1502 until 0.75 OD is sensed via the automated monitoring. Monitoring may be periodic or continuous.

In some implementations, an inducible expression system may be used. Thus, after growing to the desired OD, an inducer is added to the first growth module 1502 for inducing protein production the cells. The inducer could be a small molecule or a media exchange to a medium with a different sugar like galactose.

The cell stock 1562, after growth and induction, is transferred to the first filtration module 1504, in some implementations, for exchanging media (1564*a*). In one example, a robotic handling system moves the vial of the cell stock 1562 from the rotating growth vial of the first growth module 1502 to a vial holder of the first filtration module 1504. In another example, the robotic handling system pipettes cell stock 1562 from the rotating growth vial of the first growth module 1502 and delivers it to the first filtration module 1504. For example, the disposable pipetting tip used to transfer the cell stock 1562*a* to the first growth module 1502 may be used to transfer the cell stock 1562 from the first growth module 1502 to the first filtration module 1504. In some embodiments, prior to transferring the cell stock 1562 from the first growth module 1502 to the first filtration module 1504, the first growth module 1502 is cooled to 4° C. so that the cell stock 1562 is similarly reduced to this temperature. In a particular example, the temperature of the first growth module 1502 may be reduced to about 4° C. over the span of about 8 minutes, and the growth module 1502 may hold the temperature at 4° C. for about 15 minutes to ensure reduction in temperature of the cell stock 1562. During media exchange, in an illustrative example, 0.4 ml of 1M sorbitol may be added to the cell stock 1562.

Prior to transferring the cell stock 1562, in some implementations, a filter of the first filtration module 1004 is pre-washed using a wash solution. The wash solution, for example, may be supplied in a wash cartridge. The first filtration module 1504, for example, may be fluidly connected to the wash solution of the wash cartridge, as described in relation to FIG. 12A.

The first filtration module 1504, for example, may be part of a dual filtration module such as the filtration module 1250 described in relation to FIGS. 12B and 12C. In a particular example, the first filtration module 1504 may be maintained at 4° C. during the washing and eluting process while transferring cell materials between an elution vial and the first filtration module 1504.

After the media exchange operation, in some implementations, the cell stock 1562 is transferred back to the first growth module 1502 for conditioning (1566*a*). In one example, a robotic handling system moves the vial of the cell stock 1562 from the first filtration module 1504 to the first growth module 1502. In another example, the robotic handling system pipettes cell stock 1562 from the first filtration module 1504 and delivers it to the rotating growth vial of the first growth module 1502. During conditioning, for example, 5 ml DTT/LIAc and 80 mM of Sorbitol may be added to the cell stock 1562. For example, the robotic handling system may transfer the DTT/LIAc and Sorbitol, individually or concurrently, to the first growth module 1502. The cell stock 1562 may be mixed with the DTT/LIAc and Sorbitol, for example, via the rotation of the rotating growth vial of the first growth module 1502. During conditioning, the cell stock 1562 may be maintained at a temperature of 4° C.

In some implementations, after conditioning, the cell stock 1562 is transferred to the first filtration module 1504 for washing and preparing the cells (1568). For example, the cells may be rendered electrocompetent at this step. In one example, a robotic handling system moves the vial of the cell stock 1562 from the rotating growth vial of the first growth module 1502 to a vial holder of the first filtration module 1504. In another example, the robotic handling system pipettes cell stock 1562 from the rotating growth vial of the first growth module 1502 and delivers it to the first filtration module.

Prior to transferring the cell stock, in some implementations, a filter of the first filtration module 1504 is pre-washed using a wash solution. The wash solution, for example, may be supplied in a wash cartridge. The first filtration module 1504, for example, may be fluidly connected to the wash solution of the wash cartridge, as described in relation to FIG. 12A. In other embodiments, the same filter is used for rendering electrocompetent as the filter used for media exchange at step 1564*a*. In some embodiments, 1M sorbitol is used to render the yeast cells electrocompetent.

In some implementations, upon rendering electrocompetent at the filtration module 1504, the cell stock 1562 is transferred to a transformation module 1506 (e.g., flow-through electroporation module) for transformation. In one example, a robotic handling system moves the vial of the cell stock 1562 from the vial holder of the first filtration module 1504 to a reservoir of the flow-through electroporation module 1506. In another example, the robotic handling system pipettes cell stock 1562 from the filtration module 1504 or a temporary reservoir and delivers it to the first filtration module 1504. In a particular example, 400 μl of the concentrated cell stock 1562 from the first filtration module 1504 is transferred to a mixing reservoir prior to transfer to the transformation module 1506. For example, the cell stock 1562 may be transferred to a reservoir in a cartridge for mixing with the nucleic acid components (vector backbone and oligonucleotide), then mixed and transferred by the robotic handling system using a pipette tip. Because the vector backbone and oligonucleotide are assembled in the cells (in vivo), a nucleic acid assembly module is not a necessary component. In a particular example, the transformation module is maintained at 4° C.

In some implementations, the nucleic acids to be assembled and the cell stock 1562 is added to the FTEP module 1506 and the cell stock 1562 is transformed (1526*e*). The robotic handling system, for example, may transfer the mixture of the cell stock 1562*e* and nucleic acid assembly to the flow-through electroporation module 1506 from a mixing reservoir, e.g., using a pipette tip or through transferring a vial or tube. In some embodiments, a built-in FTEP module such as the flow-through electroporation modules FIGS. 4A-4I, 5A-5G, 6, 8A-8U, 9A-9C, and 10A-10C (that is, single unit FTEPs) is used to transform the cell stock 1562*e*. In other embodiments, a cartridge-based electroporation module is used to transform the cell stock 1562*e*. The FTEP module 1506, for example, may be held at a temperature of 4° C.

The transformed cell stock 1562*e*, in some implementations, is transferred to the second growth module 1508 for recovery (1528*a*). In a particular example, 20 ml of transformed cells undergo a recovery process in the second growth module 1508.

In some implementations, a selective medium, e.g. an auxotrophic growth medium or a medium containing a drug, is transferred to the second growth vial (not illustrated), and the cells are left to incubate for a further period of time in a selection process. In an illustrative example, an antibiotic may be transferred to the second growth vial, and the cells may incubate for an additional two hours at a temperature of 30° C.

After recovery, the cells may be ready for further processing or for storage in a cell library. For example, a portion of the cells may be transferred to a storage module as cell library output (1576*a*), while another portion of the cells may be prepared for processing, e.g., induction of protein expression and isolation of produced proteins (1578*a*). The cells may be stored, for example, at a temperature of 4° C.

In some implementations, in preparation for processing, the transformed cells are transferred to the second filtration module 1510 for media exchange (1578*a*). Prior to transferring the transformed cell stock 1562*a*, in some implementations, a filter of the second filtration module 1504 is pre-washed using a wash solution. The wash solution, for example, may be supplied in a wash cartridge. The second filtration module 1510, for example, may be fluidly connected to the wash solution of the wash cartridge, as described in relation to FIG. 12A.

The second filtration module 1510, for example, may be part of a dual filtration module such as the filtration module 1250 described in relation to FIGS. 12B and 12C. In a particular example, the second filtration module 1510 may be maintained at 4° C. during the washing and eluting process while transferring cell materials between an elution vial and the second filtration module 1510.

In some implementations during the filtration process, an enzymatic preparation is added to lyse the cell walls of the cell stock 1562*a*. For example, a yeast lytic enzyme such as Zylomase® may be added to lyse the cell walls. The yeast lytic enzyme, in a particular example, may be incubated in the cell stock 1526*a* for between 5-60 minutes at a temperature of 30° C. The output of this filtration process, in a particular example, is deposited in a vial or tube to await further processing. The vial or tube may be maintained in a storage module at a temperature of 4° C.

The first stage of processing may take place during a single day. At this point of the workflow 1560, in some implementations, new materials are manually added to the automated instrument. For example, new cell stock 1562*b* and a new reagent cartridge may be added. Further, a new wash cartridge, replacement filters, and/or replacement pipette tips may be added to the automated instrument at this point. Further, in some embodiments, the filter module may undergo a cleaning process and/or the solid and liquid waste units may be emptied in preparation for the next round of processing.

FIGS. 17A and 17B illustrate embodiments of automated multi-module cell processing instruments for performing cell transformation, selection, gene analysis, or protein expression. The automated multi-module cell processing instruments, for example, may be desktop instruments designed for use within a laboratory environment. The automated multi-module cell processing instruments may incorporate both reusable and disposable elements for performing various staged operations in conducting automated genome cleavage and/or protein production in cells.

FIG. 17A is a block diagram of a first example instrument 1700 for performing automated cell processing. In some implementations, the instrument 1700 includes a deck, a reagent supply receptacle 1704 for introducing DNA sample components to the instrument 1700, a cell supply receptacle 1706 for introducing cells to the instrument 1700, and a robot handling system 1708 for moving materials between modules (for example, modules 1710*a*, 1710*b*, 1710*c*, 1710*d*) receptacles (for example, receptacles 1704, 1706, 1712*a-c*, 1722, 1724, and 1726), and storage units (e.g., units 1718, 1728, and 1714) of the instrument 1700 to perform the automated cell processing. Upon completion of transformation of the cell supply 1706, in some embodiments, cell output 1712 may be transferred by the robot handling system 1708 to a storage unit 1714 for temporary storage and later retrieval.

The robotic handling system 1708, for example, may include an air displacement pump to transfer liquids from the various material sources to the various modules 1710*a-d* and storage unit 1714. In other embodiments, the robotic handling system 1708 may include a pick and place head to transfer containers of source materials (e.g., tubes) from a supply cartridge (not illustrated, discussed in relation to FIG. 1A) to the various modules 1710*a-d*. In some embodiments, one or more cameras or other optical sensors (not shown), confirm proper gantry movement and position.

In some embodiments, the robotic handling system 1708 uses disposable transfer tips provided in a transfer tip supply 1716 to transfer source materials, reagents 1704 (e.g., for nucleic acid assembly), and cells 1706 within the instrument 1700. Used transfer tips, for example, may be discarded in a solid waste unit 1718. In some implementations, the solid waste unit 1718 contains a kicker to remove tubes from the pick and place head of robotic handling system 1708.

In some implementations, the instrument 1700 is controlled by a processing system 1720 such as the processing system 1410 of FIG. 14. The processing system 1720 may be configured to operate the instrument 1700 based on user input. The processing system 1720 may control the timing, duration, temperature and other operations of the various modules 1710 of the instrument 1700. The processing system 1720 may be connected to a power source (not shown) for the operation of the instrument 1700.

Instrument 1700 includes an FTEP device 1710c to introduce nucleic acid(s) into the cells 1706. For example, the robotic handling system 1708 may transfer the reagent 1704 and cells 1706 to the FTEP device 1710c. The FTEP device 1710 conducts cell transformation or transfection via electroporation. The processing system 1720 may control temperature and operation of the FTEP device 1710c. In some implementations, the processing system 1720 effects operation of the FTEP device 1710c according to one or more variable controls set by a user.

Following transformation, in some implementations, the cells may be transferred to a recovery module 1710d. In some embodiments, the recovery module 1710d is a combination recovery and induction of protein production module. In the recovery module 1710d, the cells are allowed to recover, express the nucleic acids and, in an inducible system, transcription of the introduced nucleic acids is induced in the cells, e.g., by means of temporally-controlled induction such as, in some examples, chemical, light, viral, or temperature induction or the introduction of an inducer molecule 1724 for expression of the protein.

Following protein production, in some implementations the cells are transferred to the storage unit 1714, where the cells can be stored as cell output 1712a-d until the cells are removed for further study or retrieval of a transformed cell population, e.g., a transformed cell library.

A portion of a cell output 1712a, in some embodiments, is transferred to an automated cell growth module 1710a. For example, all of the cell output 1712a may be transferred, or only an aliquot may be transferred such that the instrument retains incrementally modified samples. The cell growth module 1710a, in some implementations, measures the OD of the cells during growth to ensure they are at a desired concentration prior to induction of transcription and, in some aspects, translation. Other measures of cell density and physiological state that can be used include but are not limited to, pH, dissolved oxygen, released enzymes, acoustic properties, and electrical properties.

To reduce the background of cells that have not been transformed, in some embodiments the growth module 1710a performs a selection process to enrich for the transformed cells using a selective growth medium 1726. For example, the introduced nucleic acid can include a gene that confers antibiotic resistance or some other selectable marker. In some implementations, multiple selective genes or markers 1726 may be introduced into the cells during processing. Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, and chloramphenicol-resistance gene.

From the growth module 1710a, the cells may be transferred to a filtration module 1710b. The filtration module 1710b or, alternatively, a cell wash and concentration module, may enable media exchange. In some embodiments, removing dead cell background is aided using lytic enhancers such as detergents, osmotic stress, temperature, enzymes, proteases, bacteriophage, reducing agents, or chaotropes. In other embodiments, cell removal and/or media exchange is used to reduce dead cell background. Waste product from the filtration module 1710b, in some embodiments, is collected in a liquid waste unit 1728.

After filtration, the cells may be presented to the FTEP device (transformation module) 1710c, and then to the recovery module 1710d and finally to the storage unit 1714 as detailed above.

Turning to FIG. 17B, similar to FIG. 17A, a second exemplary instrument 1740 for performing automated genome cleavage and/or protein production in cells, the reagent supply receptacle 1704 for introducing one or more nucleic acid components to the instrument 1740, the cell supply receptacle 1706 for introducing cells to the instrument 1740, and the robot handling system 1708 for moving materials between modules (for example, modules 1710a, 1710b, 1710c, 1710f, 1710g, 1710m, and 1710h), receptacles (for example, receptacles 1704 1706, 1712a-c, 1724, 1742, 1744, and 1746), and storage units (e.g., units 1714, 1718, and 1728) of the instrument 1740 to perform the automated cell processing. Upon completion of processing of the cell supply 1706, in some embodiments, cell output 1712a-c may be transferred by the robot handling system 1708 to the storage unit 1714 for temporary storage and later retrieval.

In some embodiments, the robotic handling system 1708 uses disposable transfer tips provided in the transfer tip supply 1716 to transfer source materials, a vector backbone 1742, an expression cassette or oligos 1744, reagents 1704 (e.g., for nucleic acid assembly, nucleic acid purification, to render cells electrocompetent, etc.), and cells 1706 within the instrument 1740, as described in relation to FIG. 17A.

As described in relation to FIG. 17A, in some implementations, the instrument 1740 is controlled by the processing system 1720 such as the processing system 1410 of FIG. 14.

The instrument 1740, in some embodiments, includes a nucleic acid assembly module 1710g, and in certain exemplary automated multi-module cell processing instruments, the nucleic acid assembly module 1710g may perform in some embodiments nucleic acid assembly.

In some embodiments, after assembly of the nucleic acids, the nucleic acids (e.g., in the example of a nucleic acid assembly, the nucleic acid assembly mix (nucleic acids+ nucleic acid assembly reagents)) are transferred to a purification module 1710h. Here, unwanted components of the nucleic acid assembly mixture are removed (e.g., salts) and, in certain embodiments, the assembled nucleic acids are concentrated. For example, in an illustrative embodiment, in the purification module 1710h, the nucleic acid assembly mix may be combined with a no-salt buffer and magnetic beads, such as Solid Phase Reversible Immobilization (SPRI) magnetic beads or AMPure™ beads. The nucleic acid assembly mix may be incubated for sufficient time (e.g., 30 seconds to 10 minutes) for the assembled nucleic acids to bind to the magnetic beads. In some embodiments, the purification module includes a magnet configured to engage the magnetic beads. The magnet may be engaged so that the supernatant may be removed from the bound assembled nucleic acids and so that the bound assembled nucleic acids can be washed with, e.g., 80% ethanol. Again, the magnet may be engaged and the 80% ethanol wash solution removed. The magnetic bead/assembled nucleic acids may be allowed to dry, then the assembled nucleic acids may be eluted and the magnet may again be engaged, this time to sequester the beads and to remove the supernatant that contains the eluted assembled nucleic acids. The assembled nucleic acids may then be transferred to the transformation module (e.g., electroporator in a preferred embodiment). The transformation module may already contain the electrocompetent cells upon transfer.

Instrument 1740 includes an FTEP device 1710c for introduction of the nucleic acid(s) into the cells 1706, as described in relation to FIG. 17A. However, in this circumstance, the assembled nucleic acids 1704, output from the purification module 1710h, are transferred to the FTEP device 1710c to combine with the cells 1706.

Following transformation in the FTEP device 1710c, in some implementations, the cells may be transferred to a recovery module 1710m. In the recovery module 1710e, the cells are allowed to recover, express the exogenous nucleic acids electroporated into the cells and, in an inducible system, transcription and translation of a protein is induced, e.g., by means of temporally-controlled induction such as, in some examples, chemical, light, viral, or temperature induction or the introduction of the inducer molecule for expression of the protein.

Following recovery, in some implementations the cells are transferred to an expression module 1710f. The expression module 1710f provides appropriate conditions to induce production of a protein, e.g., through expression of the introduced nucleic acids and the induction of an inducible protein. The protein may be, in some examples, chemically induced, biologically induced (e.g., via inducible promoter) virally induced, light induced, temperature induced, and/or heat induced within the expression module 1710f.

Following transformation (and, e.g., protein production), in some implementations, the cells are transferred to the storage unit 1714 as described in relation to FIG. 17A.

A portion of a cell output 1712a, in some embodiments, is transferred to the automated cell growth module 1710a, as discussed in relation to FIG. 17A.

To reduce background of cells that have not been transformed, in some embodiments, the growth module 1710a performs a selection process to enrich for the transformed cells using a selective growth medium 1726, as discussed in relation to FIG. 17A.

From the growth module 1710a, the cells may be transferred to the filtration module 1710b, as discussed in relation to FIG. 17A. As illustrated, eluant from an eluting supply 1746 (e.g. buffer, glycerol) may be transferred into the filtration module 1710b for media exchange.

After filtration, the cells may be transferred to the FTEP device 1710c for transformation, and then to the recovery module 1710m, and the protein expression module 1710f and finally to the storage unit 1714 as detailed above.

In some embodiments, the automated multi-module cell processing instruments of FIGS. 17A and/or 17B contain one or more replaceable supply cartridges and a robotic handling system. Each cartridge may contain one or more of a nucleic acid assembly mix, oligonucleotides, vector, growth media, selection agent (e.g., antibiotics), inducing agent, nucleic acid purification reagents such as Solid Phase Reversible Immobilization (SPRI) beads, ethanol, and 10% glycerol.

Although the exemplary instruments 1700, 1740 are illustrated as including a particular arrangement of modules 1710, these arrangements are for illustrative purposes only.

For example, in other embodiments, more or fewer modules 1710 may be included within each of the instruments 1700, 1740. Also, different modules may be included in the instrument, such as, e.g., a module that facilitates cell fusion for providing, e.g., hybridomas, a module that amplifies nucleic acids before assembly, and/or a module that facilitates protein production. Further, certain modules 1710 may be replicated within certain embodiments, such as the duplicate cell growth modules. Each of the instruments 1700 and 1740, in another example, may be designed to accept a media cartridge such as the cartridges of FIGS. 11A and 11C. Further modifications are possible.

Protein Expression Module

Alternatively, or in addition, the instrument may include a protein expression module where cells are allowed to express the nucleic acids introduced by transformation of the cells in the system. Traditional strategies for recombinant protein expression involve culturing the transformed cells so that they transcribe and translate the desired protein. Typically, the cells are then lysed to extract the expressed protein for subsequent purification, and such lysis can be performed on the instrument or following collection of the cells from the system. Both prokaryotic and eukaryotic in vivo protein expression systems may be used in the instruments of the disclosure.

The selection of the system depends on the type of protein, the requirements for functional activity and the desired yield. The expression systems that can be used with the instruments of the disclosure include any expression system known to a person skilled in the art amenable to automated transformation or transfection, including as eukaryotic expression systems such as yeasts (*S. cerevisiae* or *P. pastoris*), bacterial expression systems, insect cells (sf9) or mammalian expression systems such as CHO, 293 or HEK cells. In one embodiment, it is preferred to transform the vector in an *E. coli* expression system, wherein *E. coli* BL21(DE3) is particularly preferred. Each system has advantages and challenges, and the particular system that can be used in the inventions of the disclosure can be selected for the particular application, as will be apparent to one of ordinary skill in the art upon reading the present disclosure.

Cell Sorting Module

Alternatively, or in addition, the instrument may include a sorting module where cells expressing different cell surface markers are sorted from those cells that do not express such cell surface markers. For example, fluorescence-activated cell sorting ("FACS") e.g., different fluorophores or other optically-distinguishable markers that bind to the cell surface markers of interest are used to sort cells. Fluorophores of use in this aspect include TagBFP, TagCFP, TagGFP2, TagYFP, TagRFP, FusionRed, mKate2, TurboGFP, TurboYFP, TurboRFP, TurboFP602, TurboFP635, TurboFP650, AmCyan1, AcvGFP1, ZsGreen1, ZsYellow1, mBanana, mOrange, mOrange2, DsRed-Express 2, EsRed-Express, tdTomato, DsRed-Monomer, DsRed2, AsRed2, mStrawberry, mCherry, HcRed1, mRaspberry, E2-Crimson, mPlum, Dendra 2, Timer, and PAmCherry, HALO-tags, or infrared-shifted fluorescent proteins. Alternatively, chemiluminescent markers may be employed.

Control System for an Automated Instrument

Figure 16:
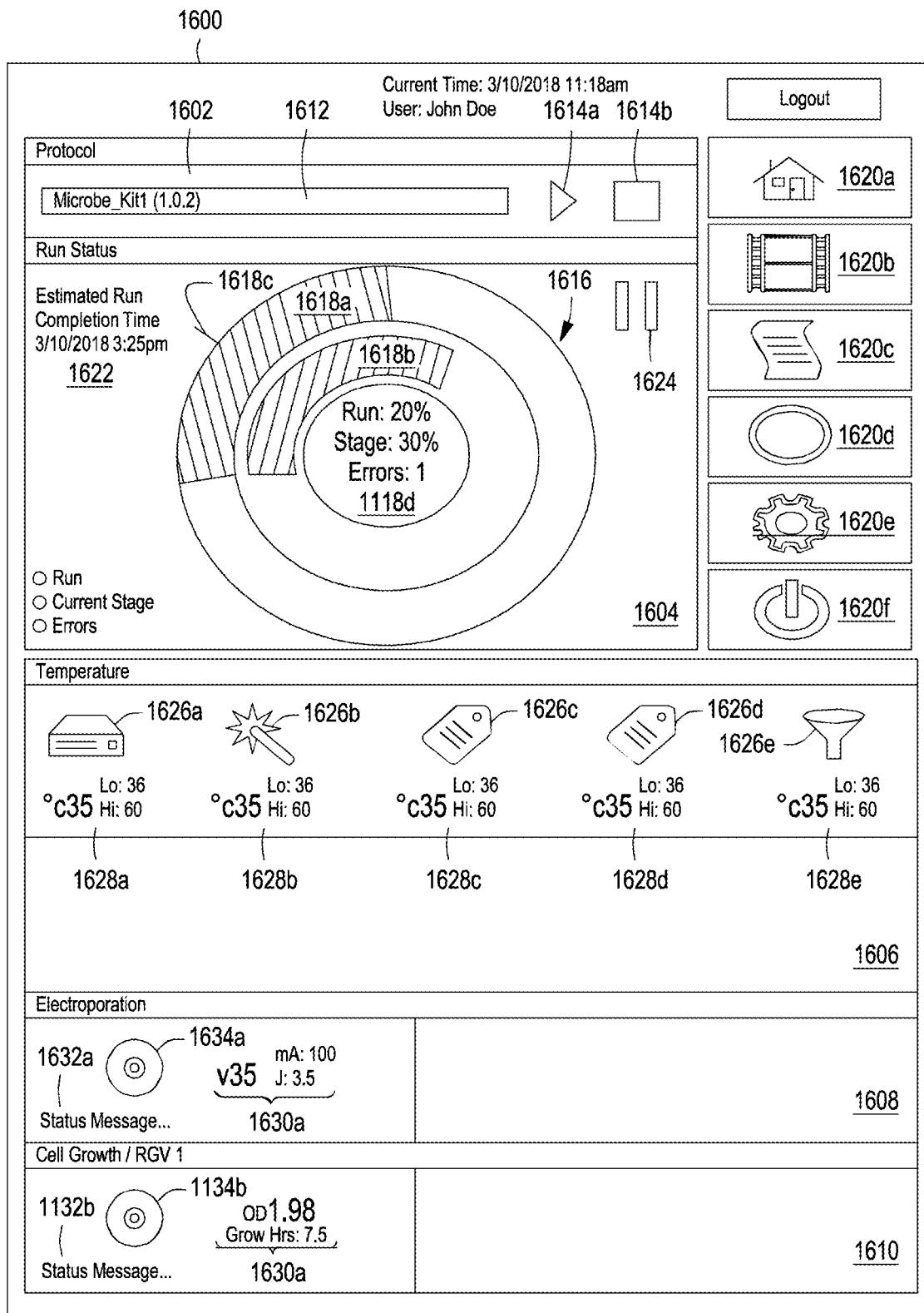
FIG. 16 illustrates an example graphical user interface for providing instructions to and receiving feedback from an instrument for automated introduction of nucleic acids instrument.

Turning to FIG. 16, a screen shot illustrates an example graphical user interface (GUI) 1600 for interfacing with an automated instrument. The interface, for example, may be presented on the display 236 of FIGS. 2C and 2D. In one example, the GUI 1600 may be presented by the processing system 1410 of FIG. 14 on the touch screen 1416.

In some implementations, the GUI 1600 is divided into a number of information and data entry panes, such as a protocol pane 1602, a temperature pane 1606, an electroporation pane 1608, and a cell growth pane 1610. Further panes are possible. For example, in some embodiments the GUI 1600 includes a pane for each module, such as, in some examples, one or more of each of a nucleic acid assembly module, a purification module, a cell growth module, a filtration module, a transformation module, and a recovery module. The lower panes of the GUI 1600, in some embodiments, represent modules applicable to the present work flow (e.g., as selected in the protocol pane 1602 or as designated within a script loaded through a script interface (not illustrated)). In some embodiments, a scroll or paging feature may allow the user to access additional panes not illustrated within the screen shot of FIG. 16.

The GUI 1600, in some embodiments, includes a series of controls 1620 for accessing various screens such as the illustrated screen shot (e.g., through using a home control 1620*a*). The user in some embodiments, may select a help control 1620*d* to obtain further information regarding the features of the GUI 1600 and the automated instrument. In some implementations, the user selects a settings control 1620*e* to access settings options for desired processes and/or the GUI 1600 such as, in some examples, time zone, language, units, network access options. A power control 1620*f*, when selected, allows the user to power down the automated instrument.

Turning to the protocol pane 1602, in some implementations, a user selects a protocol (e.g., script or work flow) for execution by the automated instrument by entering the protocol in a protocol entry field 1612 (or, alternatively, drop-down menu). In other embodiments, the protocol may be selected through a separate user interface screen, accessed for example by selecting the script control 1620*b*. In another example, the automated instrument may select the protocol and present it in the protocol entry field 1612. For example, the processing system of the automated instrument may scan machine-readable indicia positioned on one or more cartridges loaded into the automated instrument to determine the appropriate protocol. As illustrated, the "Microbe_Kit1 (1.0.2)" protocol has been selected, which may correspond to a kit of cartridges and other disposable supplies purchased for use with the automated instrument.

In some implementations, the protocol pane 1602 further includes a start control 1614*a* and a stop control 1614*b* to control execution of the protocol presented in the protocol entry field 1612. The GUI 1600 may be provided on a touch screen interface, for example, where touch selection of the start control 1614*a* starts cell processing, and selection of the stop control 1614*b* stops cell processing.

Turning to the run status pane 1604, in some implementations a chart 1616 illustrates stages of the processing of the protocol identified in the protocol pane 1602. For example, a portion of run completion 1618*a* is illustrated in blue, while a portion of current stage 1618*b* is illustrated in green, and any errors 1618*c* are flagged with markers extending from the point in time along the course of the portion of the run completion 1618*a* where the error occurred. A message region 1618*d* presents a percentage of run completed, a percentage of stage completed, and a total number of errors. In some embodiments, upon selection of the chart 1616, the user may be presented with greater details regarding the run status such as, in some examples, identification of the type of error, a name of the current processing stage (e.g., nucleic acid assembly, purification, cell growth, filtration, transformation, recovery, etc.), and a listing of processing stages within the run. Further, in some embodiments a run completion time message indicates a date and time at which the run is estimated to complete. In some embodiments (not shown), the run status pane 1604 additionally illustrates an estimated time at which user intervention will be required (e.g., cartridge replacement, solid waste disposal, liquid waste disposal, etc.).

In some implementations, the run status pane 1604 includes a pause control 1624 for pausing cell processing. The user may select to pause the current run, for example, to correct for an identified error or to conduct manual intervention such as waste removal.

The temperature pane 1606, in some embodiments, illustrates a series of icons 1126 with corresponding messages 1628 indicating temperature settings for various apparatus of the automated instrument. The icons, from left to right, may represent an FTEP module 1626*a* (e.g., FTEP device associated with the reagent cartridge 1122 of FIG. 11E), a purification module 1626*b*, a first growth module 1626*c*, a second growth module 1626*d*, and a filtration module 1626*e*. The corresponding messages 1628*a-e* identify a present temperature, low temperature, and high temperature of the corresponding module (e.g., for this stage or this run). In selecting one of the icons 1626, in some embodiments, a graphic display of temperature of time may be reviewed.

Beneath the temperature pane, in some implementations, a series of panes identify present status of a number of modules. For example, the electroporation pane 1608 represents status of a transformation module, while the cell growth pane 1610 represents the status of a growth module. In some embodiments, the panes presented here identify status of a presently operational module (e.g., the module involved in cell processing in the current stage) as well as the status of any modules which have already been utilized during the current run (as illustrated, for example, in the run status pane 1604). Past status information, for example, may present to the user information regarding the parameters used in the prior stage(s) of cell processing.

Turning to the electroporation pane 1608, in some implementations, operational parameters 1630*a* of volts, milliamps, and joules are presented. Additionally, a status message 1632*a* may identify additional information regarding the functioning of the transformation module such as, in some examples, an error status, a time remaining for processing, or contents of the module (e.g., materials added to the module). In some implementations, an icon 1634*a* above the status message 1632*a* will be presented in an active mode (e.g., colorful, "lit up", in bold, etc.) when the corresponding module is actively processing. Selection of the icon 1634*a*, in some embodiments, causes presentation of a graphic display of detailed information regarding the operational parameters 1630*a*.

Turning to the cell growth pane 1610, in some implementations, operational parameters 1630*b* of OD and hours of growth are presented. Additionally, a status message 1632*b* may identify additional information regarding the functioning of the growth module such as, in some examples, an error status, a time remaining for processing, or contents of the module (e.g., materials added to the module). In some implementations, an icon 1634*b* above the status message 1632*b* will be presented in an active mode (e.g., colorful, "lit up", in bold, etc.) when the corresponding module is actively processing. Selection of the icon 1634*b*, in some embodiments, causes presentation of a graphic display of detailed information regarding the operational parameters 1630*b*.

A hardware description of an example processing system and processing environment according to exemplary embodiments is described with reference to FIG. 14. In FIG. 14, the processing system 1410 includes a CPU 1408 which performs a portion of the processes described above. For example, the CPU 1408 may manage the processing stages of the method 1400 of FIG. 14 and/or the workflows of FIGS. 15A-C. The process data and, scripts, instructions, and/or user settings may be stored in memory 1402. These process data and, scripts, instructions, and/or user settings may also be stored on a storage medium disk 1404 such as a portable storage medium (e.g., USB drive, optical disk drive, etc.) or may be stored remotely. For example, the process data and, scripts, instructions, and/or user settings may be stored in a location accessible to the processing system 1410 via a network 1428. Further, the claimed advancements are not limited by the form of the computer-readable media on which the instructions of the inventive process are stored. For example, the instructions may be stored in FLASH memory, RAM, ROM, or any other information processing device with which the processing system 1410 communicates, such as a server, computer, smart phone, or other hand-held computing device.

Further, components of the claimed advancements may be provided as a utility application, background daemon, or component of an operating system, or combination thereof, executing in conjunction with CPU 1408 and an operating system such as with other computing systems known to those skilled in the art.

CPU 1408 may be an ARM processor, system-on-a-chip (SOC), microprocessor, microcontroller, digital signal processor (DSP), or may be other processor types that would be recognized by one of ordinary skill in the art. Further, CPU 1408 may be implemented as multiple processors cooperatively working in parallel to perform the instructions of the inventive processes described above.

The processing system 1410 is part of a processing environment 1400. The processing system 1410 in FIG. 14 also includes a network controller 1406 for interfacing with the network 1428 to access additional elements within the processing environment 1400. As can be appreciated, the network 1428 can be a public network, such as the Internet, or a private network such as an LAN or WAN network, or any combination thereof and can also include PSTN or ISDN sub-networks. The network 1428 can be wireless such as a cellular network including EDGE, 3G and 4G wireless cellular systems. The wireless network can also be Wi-Fi, Bluetooth, or any other wireless form of communication that is known.

The processing system 1410 further includes a general purpose I/O interface 1412 interfacing with a user interface (e.g., touch screen) 1416, one or more sensors 1414, and one or more peripheral devices 1418. The peripheral I/O devices 1418 may include, in some examples, a video recording system, an audio recording system, microphone, external storage devices, and/or external speaker systems. The one or more sensors 1414 may include one or more of a gyroscope, an accelerometer, a gravity sensor, a linear accelerometer, a global positioning system, a bar code scanner, a QR code scanner, an RFID scanner, a temperature monitor, and a lighting system or lighting element.

The general purpose storage controller 1424 connects the storage medium disk 1404 with communication bus 1440, such as a parallel bus or a serial bus such as a Universal Serial Bus (USB), or similar, for interconnecting all of the components of the processing system. A description of the general features and functionality of the storage controller 1424, network controller 1406, and general purpose I/O interface 1412 is omitted herein for brevity as these features are known.

The processing system 1410, in some embodiments, includes one or more onboard and/or peripheral sensors 1414. The sensors 1414, for example, can be incorporated directly into the internal electronics and/or a housing of the automated multi-module processing instrument. A portion of the sensors 1414 can be in direct physical contact with the I/O interface 1412, e.g., via a wire; or in wireless contact e.g., via a Bluetooth, Wi-Fi or NFC connection. For example, a wireless communications controller 1426 may enable communications between one or more wireless sensors 1414 and the I/O interface 1412. Furthermore, one or more sensors 1414 may be in indirect contact e.g., via intermediary servers or storage devices that are based in the network 1428; or in (wired, wireless or indirect) contact with a signal accumulator somewhere within the automated instrument, which in turn is in (wired or wireless or indirect) contact with the I/O interface 1412.

A group of sensors 1414 communicating with the I/O interface 1412 may be used in combination to gather a given signal type from multiple places in order to generate a more complete map of signals. One or more sensors 1414 communicating with the I/O interface 1412 can be used as a comparator or verification element, for example to filter, cancel, or reject other signals.

In some embodiments, the processing environment 1800 includes a computing device 1438 communicating with the processing system 1410 via the wireless communications controller 1426. For example, the wireless communications controller 1426 may enable the exchange of email messages, text messages, and/or software application alerts designated to a smart phone or other personal computing device of a user.

The processing environment 1400, in some implementations, includes a robotic material handling system 1422. The processing system 1410 may include a robotics controller 1420 for issuing control signals to actuate elements of the robotic material handling system, such as manipulating a position of a gantry, lowering or raising a sipper or pipettor element, and/or actuating pumps and valves to cause liquid transfer between a sipper/pipettor and various vessels (e.g., chambers, vials, etc.) in the automated instrument. The robotics controller 1420, in some examples, may include a hardware driver, firmware element, and/or one or more algorithms or software packages for interfacing the processing system 1410 with the robotics material handling system 1422.

In some implementations, the processing environment 1410 includes one or more module interfaces 1432, such as, in some examples, one or more sensor interfaces, power control interfaces, valve and pump interfaces, and/or actuator interfaces for activating and controlling processing of each module of the automated multi-module processing system. For example, the module interfaces 1432 may include an actuator interface for the drive motor of rotating cell growth device 1350 (FIGS. 13C and 13D) and a sensor interface for the detector board 1372 that senses optical density of cell growth within rotating growth vial 1300. A module controller 1430, in some embodiments, is configured to interface with the module interfaces 1432. The module controller 1430 may include one or many controllers (e.g., possibly one controller per module, although some modules may share a single controller). The module controller 1430, in some examples, may include a hardware driver, firmware element, and/or one or more algorithms or software packages for interfacing the processing system 1410 with the module interfaces 1432.

The processing environment 1410, in some implementations, includes a thermal management system 1436 for controlling climate conditions within the housing of the automated multi-module processing system. The thermal management system 1436 may additional control climate conditions within one or more modules of the automated instrument. The processing system 1410, in some embodiments, includes a temperature controller 1434 for interfacing with the thermal management system 1436. The temperature controller 1434, in some examples, may include a hardware driver, firmware element, and/or one or more algorithms or software packages for interfacing the processing system 1410 with the thermal management system 1436.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Production and Transformation of Electrocompetent *E. coli*

For testing transformation of the FTEP device, such as the FTEP device configured as shown in FIGS. 10B-10D (vi), electrocompetent *E. coli* cells were created. To create a starter culture, 6 ml volumes of LB chlor-25 (LB with 25 µg/ml chloramphenicol) were transferred to 14 ml culture tubes. A 25 µl aliquot of *E. coli* was used to inoculate the LB chlor-25 tubes. Following inoculation, the tubes were placed at a 45° angle in the shaking incubator set to 250 RPM and 30° C. for overnight growth, between 12-16 hrs. The OD600 value should be between 2.0 and 4.0. A 1:100 inoculum volume of the 250 ml LB chlor-25 tubes were transferred to four sterile 500 ml baffled shake flasks, i.e., 2.5 ml per 250 ml volume shake flask. The flasks were placed in a shaking incubator set to 250 RPM and 30° C. The growth was monitored by measuring OD600 every 1 to 2 hr. When the OD600 of the culture was between 0.5-0.6 (approx. 3-4 hrs), the flasks were removed from the incubator. The cells were centrifuged at 4300 RPM, 10 min, 4° C. The supernatant was removed, and 100 ml of ice-cold 10% glycerol was transferred to each sample. The cells were gently resuspended, and the wash procedure performed three times, each time with the cells resuspended in 10% glycerol. After the fourth centrifugation, the cell resuspension was transferred to a 50 ml conical Falcon tube and additional ice-cold 10% glycerol added to bring the volume up to 30 ml. The cells were again centrifuged at 4300 RPM, 10 min, 4° C., the supernatant removed, and the cell pellet resuspended in 10 ml ice-cold glycerol. The cells are aliquoted in 1:100 dilutions of cell suspension and ice-cold glycerol.

The comparative electroporation experiment was performed to determine the efficiency of transformation of the electrocompetent *E. coli* using the embodiment of the FTEP device shown at (ii), (iii), and (vi) of FIGS. 10B and 10C and (ii) and (vi) of FIG. 10D. The flow rate was controlled with a pressure control system. The suspension of cells with DNA was loaded into the FTEP inlet reservoir. The transformed cells flowed directly from the inlet and inlet channel, through the flow channel, through the outlet channel, and into the outlet containing recovery medium. The cells were transferred into a tube containing additional recovery medium, placed in an incubator shaker at 30° C. shaking at 250 rpm for 3 hours. The cells were plated to determine the colony forming units (CFUs) that survived electroporation and failed to take up a plasmid and the CFUs that survived electroporation and took up a plasmid. Plates were incubated at 30° C.; *E. coli* colonies were counted after 24 hrs.

Figure 19:
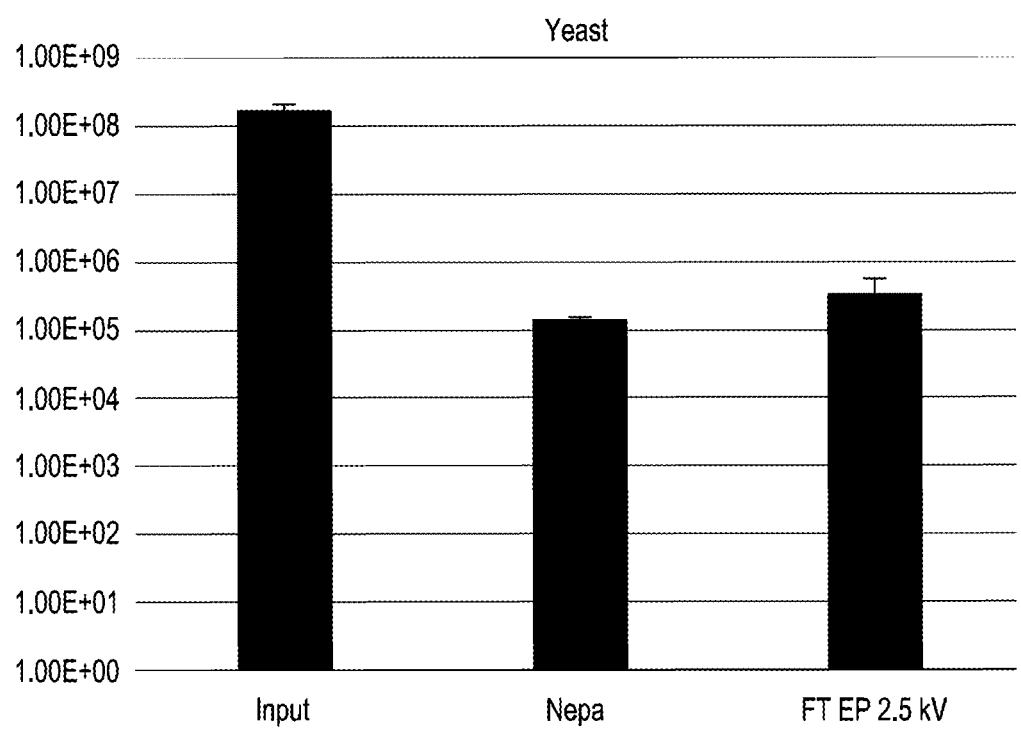
FIG. 19 is a bar graph showing the results of electroporation of *S. cerevisiae* using an FTEP device of the disclosure and a comparator electroporation method.

The flow-through electroporation experiments were benchmarked against 2 mm electroporation cuvettes (Bulldog Bio, Portsmouth, N.H.) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 19A. In FIG. 19A, the left-most bars hatched /// denote cell input, the bars to the left bars hatched \\\ denote the number of cells that survived transformation, and the right bars hatched /// denote the number of cells that were actually transformed. The FTEP device showed equivalent transformation of electrocompetent *E. coli* cells at various voltages as compared to the NEPAGENE™ electroporator. As can be seen, the transformation survival rate is at least 90% and in some embodiments is at least 95%, 96%, 97%, 98%, or 99%. The recovery ratio (the fraction of introduced cells which are successfully transformed and recovered) is in certain embodiments at least 0.001 and preferably between 0.00001 and 0.01. In FIG. 19A the recovery ratio is approximately 0.0001.

Additionally, a comparison of the NEPAGENE™ ELEPO21 and the FTEP device was made for efficiencies of transformation (uptake), cutting, and editing. In FIG. 19B, triplicate experiments were performed where the bars hatched /// denote the number of cells input for transformation, and the bars hatched \\\ denote the number of cells that were transformed (uptake), the number of cells where the genome of the cells was cut by a nuclease transcribed and translated from a vector transformed into the cells (cutting), and the number of cells where editing was effected (cutting and repair using a nuclease transcribed and translated from a vector transformed into the cells, and using a guide RNA and a donor DNA sequence both of which were transcribed from a vector transformed into the cells). In addition, note that in non-editing cell lines, the number of colonies for both the NEPAGENE™ electroporator and the FTEP showed equivalent transformation efficiencies. Moreover, it can be seen that the FTEP showed equivalent transformation, cutting, and editing efficiencies as the NEPAGENE™ electroporator.

Example 2: Production and Transformation of Electrocompetent *S. cerevisiae*

For further testing transformation of the FTEP device, such as the FTEP device configured as shown in FIGS. 10B-10D (vi), *S. cerevisiae* cells were prepared using the methods as generally set forth in Bergkessel and Guthrie, Methods Enzymol., 529:311-20 (2013). Briefly, YFAP media was inoculated for overnight growth, with 3 ml inoculate to produce 100 ml of cells. Every 100 ml of culture processed resulted in approximately 1 ml of competent cells.

Cells were incubated at 30° C. in a shaking incubator until they reached an OD600 of 1.5+/−0.1.

A conditioning buffer was prepared using 100 mM lithium acetate, 10 mM dithiothreitol, and 50 mL of buffer for every 100 mL of cells grown and kept at room temperature. Cells were harvested in 250 ml bottles at 4300 rpm for 3 minutes, and the supernatant removed. The cell pellets were suspended in 100 ml of cold 1 M sorbitol, spun at 4300 rpm for 3 minutes and the supernatant once again removed. The cells were suspended in conditioning buffer, then the suspension transferred into an appropriate flask and shaken at 200 RPM and 30° C. for 30 minutes. The suspensions were transferred to 50 ml conical vials and spun at 4300 rpm for 3 minutes. The supernatant was removed and the pellet resuspended in cold 1 M sorbitol. These steps were repeated three times for a total of three wash-spin-decant steps. The pellet was suspended in sorbitol to a final OD of 150+/−20.

A comparative electroporation experiment was performed to determine the efficiency of transformation of the electrocompetent S. cerevisiae using the FTEP device. The flow rate was controlled with a syringe pump (Harvard apparatus PHD ULTRA™ 4400). The suspension of cells with DNA was loaded into a 1 mL glass syringe (Hamilton 81320 Syringe, PTFE Luer Lock) before mounting on the pump. The output from the function generator was turned on immediately after starting the flow. The processed cells flowed directly into a tube with 1M sorbitol with carbenicillin. Cells were collected until the same volume electroporated in the NEPAGENE™ had been processed, at which point the flow and the output from the function generator were stopped. After a 3-hour recovery in an incubator shaker at 30° C. and 250 rpm, cells were plated to determine the colony forming units (CFUs) that survived electroporation and failed to take up a plasmid and the CFUs that survived electroporation and took up a plasmid. Plates were incubated at 30° C. Yeast colonies are counted after 48-76 hrs.

Figure 20:
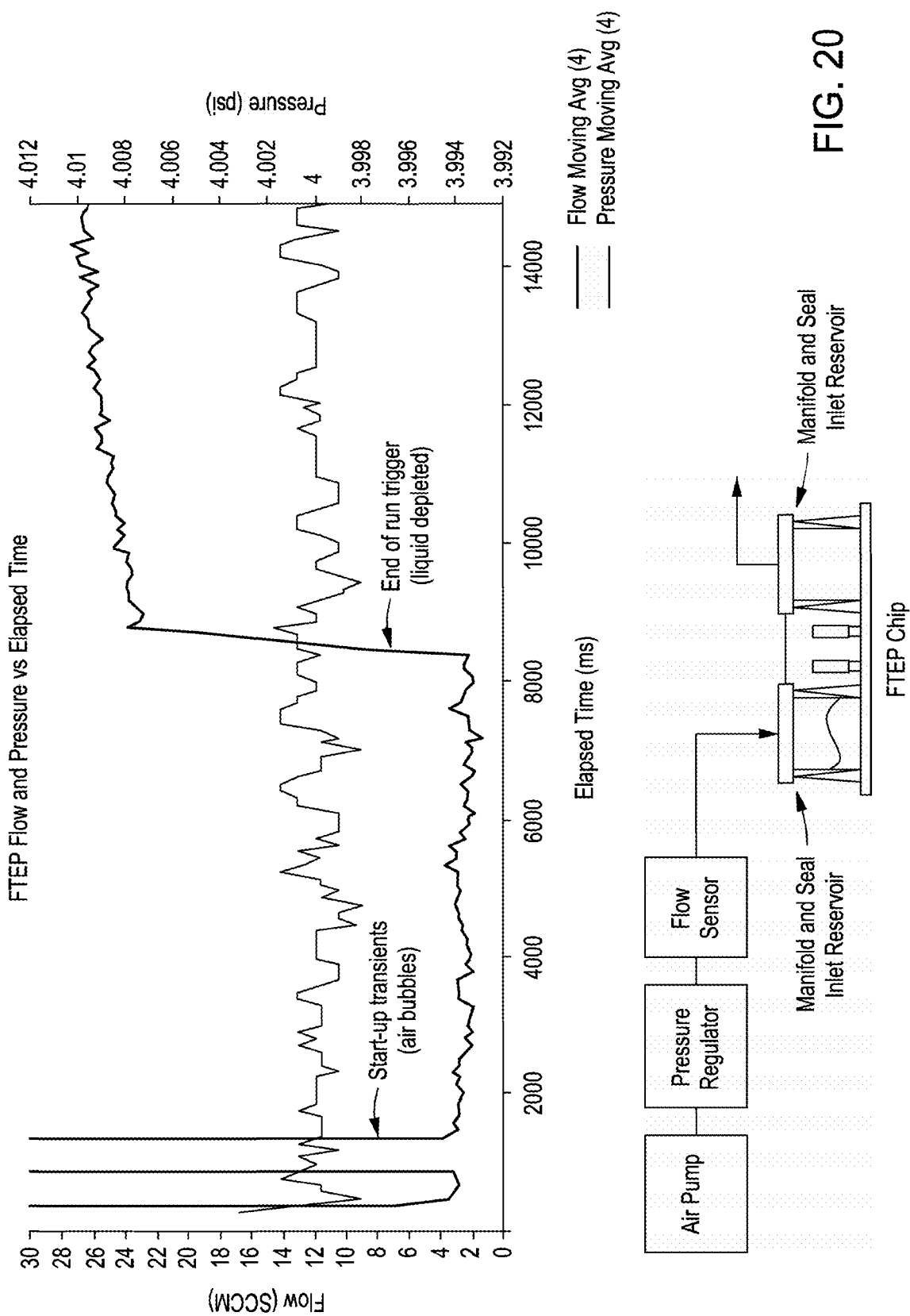
FIG. 20 shows a graph of FTEP flow and pressure versus elapsed time (top), as well as a simple depiction of the pressure system and FTEP (bottom).

The flow-through electroporation experiments were benchmarked against 2 mm electroporation cuvettes (Bulldog Bio, Portsmouth, N.H.) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 20. The device showed better transformation and survival of electrocompetent S. cerevisiae at 2.5 kV voltages as compared to the NEPAGENE™ method. Input is total number of cells that were processed.

Example 3: FTEP Pressure Sensing and Flow Rates

The pressure and sensing was also tested using an FTEP device substantially as shown in FIG. 10B-10D(vi) as part of a cartridge device as illustrated in FIG. 11E. An inline flow sensor measurement was used to indicate when, after the liquid containing the cells and DNA flowed through the FTEP chip, where the inlet reservoir was emptied. Approximately 65 μL of liquid was loaded into the input reservoir and the automated FTEP module was powered on. Looking at the graph at the top of FIG. 20, it can be seen that after a few short startup transients, the flow rate shows about ~3 standard cubic centimeters per minute (SCCM) of flow for almost 8 seconds (8000 ms) until it jumps to 24 SCCM. This transition occurs at an end of run trigger, which is an indicator that the liquid containing the cells and DNA has been processed through the FTEP device and that air is not flowing through the FTEP device. That trigger may constitute detection of an increase flow rate or a sudden fluctuation (increase or decrease) in the pressure of the air (such as at a conduit leading from a syringe pump). In one preferred embodiment, the flow sensor in FIG. 20 detects an increase in air flow indicative of the fluid being completely drained from the input reservoir. At this point, pressure may be reversed to allow a multi-pass electroporation procedure; that is, cells to electroporated may be "pulled" from the inlet toward the outlet for one pass of electroporation, and once the inlet reservoir is emptied, the sensor may reverse the pressure where the liquid and cells/DNA is "pushed" from the outlet end of the flow-through FTEP device toward the inlet end to pass between the electrodes again for another pass of electroporation. This process may be repeated one to many times. Alternatively, the pressure may be stopped entirely and the transformed cells in the outlet retrieved.

The multi-cycle approach may be particularly advantageous in that it limits the dwell time of the cells and nucleic acids in the electric filed which may in turn prevent cell damage and increase survival rates. The back-and-forth process may be repeated 1, 2, 3, 4, 5, 6, 7, 8, 9, or 10 times. FIG. 20 at bottom shows a simple depiction of the pressure system and FTEP. The pressure manifold is mated to the upwardly-extending reservoirs via one or more complementary seals or gaskets disposed on the manifold or the reservoirs.

While certain embodiments have been described, these embodiments have been presented by way of example only and are not intended to limit the scope of the present disclosures. Indeed, the novel methods, apparatuses, modules, instruments and systems described herein can be embodied in a variety of other forms; furthermore, various omissions, substitutions and changes in the form of the methods, apparatuses, modules, instruments and systems described herein can be made without departing from the spirit of the present disclosures. The accompanying claims and their equivalents are intended to cover such forms or modifications as would fall within the scope and spirit of the present disclosures.

The invention claimed is:

1. A method of transforming cells in a multi-module automated cell processing instrument comprising:
   providing cells to a receptacle configured to receive cells;
   providing nucleic acids to a receptacle configured to receive nucleic acids;
   transferring the cells to a growth module in which to grow the cells;
   growing the cells in the growth module;
   rendering the grown cells electrocompetent in a filtration module;
   transferring the electrocompetent cells to a flow-through electroporation (FTEP) module; and
   transforming the electrocompetent cells in the FTEP module, wherein the FTEP module is configured to introduce the nucleic acids into the electrocompetent cells thereby producing transformed cells, and wherein the FTEP module comprises:
   a. an inlet and an inlet channel for introducing a fluid comprising the electrocompetent cells and the nucleic acids into the FTEP module;
   b. an outlet and an outlet channel for removing a fluid comprising transformed cells from the FTEP module;
   c. a flow channel intersecting and positioned between a first inlet channel and the outlet channel, wherein the flow channel decreases in width between the first inlet channel and the outlet channel to form a constriction; and d. two or more electrodes positioned in the flow channel between the intersection of the flow channel with the inlet channel and the intersection of the flow channel with the outlet channel; wherein the electrodes are in fluid communication with fluid in the flow channel but are not in the direct flow path of the cells in the flow channel; and wherein the electrodes apply one or more electric pulses to the cells in the fluid as they pass through the flow channel, thereby introducing the nucleic acid into the electrocompetent cells;

wherein the automated multi-module cell processing instrument comprises a processor configured to operate the automated multi-module cell processing instrument based on user input and/or selection of a pre-programmed script, and wherein the automated multi-module cell processing instrument comprises an automated liquid handling system configured to move liquids from the receptacle configured to receive cells to the growth module, from the growth module to the filtration module, from the filtration module to the FTEP module, and from the receptacle configured to receive nucleic acids to the FTEP module.

2. The method of claim 1 wherein the FTEP module further comprises a reservoir connected to the inlet for introducing the cells in fluid into the FTEP module and a reservoir connected to the outlet for removing transformed cells from the FTEP module.

3. The method of claim 2 further comprising a pressure manifold mated to the reservoirs.

4. The method of claim 3 further comprising gaskets positioned where the pressure manifold mates to the reservoirs.

5. The method of claim 1 wherein the electrodes of the FTEP module are from 5 mm to 50 cm in diameter.

6. The method of claim 1 wherein the constriction is from 10 μM to 5 mm.

7. The method of claim 1 wherein the FTEP module further comprises a filter between the inlet channel and the electrodes.

8. The method of claim 7 wherein the filter is positioned between the inlet channel and the constriction and is of substantially uniform density.

9. The method of claim 7 wherein the filter is positioned between the inlet channel and the constriction increases in density from the inlet channel to the constriction.

10. The method of claim 1 wherein one electrode is positioned before the constriction and one electrode is positioned after the constriction.

11. The method of claim 1 wherein the device is configured for use with bacterial, yeast and mammalian cells.

12. The method of claim 1 wherein the automated multi-module cell processing instrument further comprises a reagent cartridge.

13. The method of claim 12 wherein the FTEP module is located on the reagent cartridge.

14. The method of claim 12 wherein the reservoirs are disposed in the reagent cartridge.

15. The method of claim 1 wherein the growth module measures OD of the growing cells.

16. The method of claim 15 wherein OD is measured continuously.

17. The method of claim 15 wherein OD is measured at intervals selected by a user.

18. The method of claim 15 wherein the processor is configured to alert a user when the growing cells have reached a desired OD.

19. The method of claim 1 wherein the automated cell processing instrument further comprises a protein production module and the automated handling system moves the transformed cells to the protein production module.

20. The method of claim 1 wherein the electrodes of the FTEP module are from 5 mm to 50 cm in diameter.

21. The method of claim 1 wherein the FTEP module further comprises a filter between the inlet channel and the electrodes.

22. The method of claim 21 wherein the filter is of substantially uniform density.

23. The method of claim 21 wherein the filter increases in density from the inlet channel to the outlet channel.

24. The method of claim 22 wherein protein production is induced by an inducer molecule.

25. A method of transforming cells in a multi-module automated cell processing instrument comprising:
providing cells to a receptacle configured to receive cells;
providing nucleic acids to a receptacle configured to receive nucleic acids;
transferring the cells to a growth module in which to grow the cells;
growing the cells in the growth module;
rendering the grown cells electrocompetent in a filtration module;
transferring the electrocompetent cells to a flow-through electroporation (FTEP) module; and
transforming the electrocompetent cells in the FTEP module, wherein the FTEP module is configured to introduce the nucleic acids into the electrocompetent cells thereby producing transformed cells, and wherein the FTEP module comprises:
a. an inlet and an inlet channel for introducing a fluid comprising the electrocompetent cells and the nucleic acids into the FTEP module;
b. an outlet and an outlet channel for removing a fluid comprising transformed cells from the FTEP module;
c. a flow channel intersecting and positioned between a first inlet channel and the outlet channel; and
d. two or more electrodes positioned in the flow channel between the intersection of the flow channel with the inlet channel and the intersection of the flow channel with the outlet channel; wherein the electrodes are in fluid communication with fluid in the flow channel but are not in the direct flow path of the cells in the flow channel; and wherein the electrodes apply one or more electric pulses to the cells in the fluid as they pass through the flow channel, thereby introducing the nucleic acid into the electrocompetent cells;

wherein the automated multi-module cell processing instrument comprises a processor configured to operate the automated multi-module cell processing instrument based on user input and/or selection of a pre-programmed script, and wherein the automated multi-module cell processing instrument comprises an automated liquid handling system configured to move liquids from the receptacle configured to receive cells to the growth module, from the growth module to the filtration module, from the filtration module to the FTEP module, and from the receptacle configured to receive nucleic acids to the FTEP module.

26. The method of claim 25 wherein the FTEP module further comprises a reservoir connected to the inlet for introducing the cells in fluid into the FTEP module and a reservoir connected to the outlet for removing transformed cells from the FTEP module.

27. The method of claim 26 further comprising a pressure manifold mated to the reservoirs.

28. The method of claim 27 further comprising gaskets positioned where the pressure manifold mates to the reservoirs.

29. The method of claim 25 wherein device is configured for use with bacterial, yeast and mammalian cells.

30. The method of claim 25 wherein the growth module measures OD of the growing cells.

31. The method of claim 30 wherein OD is measured continuously.

32. The method of claim 30 wherein OD is measured at intervals selected by as user.

33. The method of claim 30 wherein the processor is configured to alert a user when the growing cells have reached a desired OD.

34. The method of claim 25 wherein the automated cell processing instrument further comprises a protein production module and the automated handling system moves the transformed cells to the protein production module.

35. The method of claim 34 wherein protein production takes place in the growth module.

36. The method of claim 34 wherein the protein production module and the growth module are separate modules.

37. The method of claim 34 wherein protein production is induced.

38. The method of claim 37 wherein protein production is induced by temperature.

39. The method of claim 25 further comprising a reagent cartridge.

40. The method of claim 39 wherein the FTEP is located in the reagent cartridge.

\* \* \* \* \*